(12) United States Patent
Hashihayata et al.

(10) Patent No.: US 9,428,483 B2
(45) Date of Patent: Aug. 30, 2016

(54) PRODRUG OF FLUORINE-CONTAINING AMINO ACID

(71) Applicant: TAISHO PHARMACEUTICAL CO., LTD., Toshima-ku, Tokyo (JP)

(72) Inventors: Takashi Hashihayata, Toshima-ku (JP); Norikazu Otake, Toshima-ku (JP); Naoki Miyakoshi, Toshima-ku (JP); Kazunari Sakagami, Toshima-ku (JP)

(73) Assignee: TAISHO PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/403,790

(22) PCT Filed: May 31, 2013

(86) PCT No.: PCT/JP2013/065202
§ 371 (c)(1),
(2) Date: Nov. 25, 2014

(87) PCT Pub. No.: WO2013/180271
PCT Pub. Date: Dec. 5, 2013

(65) Prior Publication Data
US 2015/0141669 A1 May 21, 2015

(30) Foreign Application Priority Data

Jun. 1, 2012 (JP) .................................. 2012-126162
Mar. 15, 2013 (JP) .................................. 2013-052574

(51) Int. Cl.
| C07D 207/08 | (2006.01) |
| C07D 307/88 | (2006.01) |
| C07C 323/60 | (2006.01) |
| A61K 31/357 | (2006.01) |
| C07C 237/04 | (2006.01) |
| C07C 271/24 | (2006.01) |
| C07C 237/20 | (2006.01) |
| A61K 31/265 | (2006.01) |
| C07D 317/50 | (2006.01) |
| C07D 317/40 | (2006.01) |
| C07C 229/50 | (2006.01) |

(52) U.S. Cl.
CPC ........... *C07D 317/50* (2013.01); *A61K 31/265* (2013.01); *A61K 31/357* (2013.01); *C07C 229/50* (2013.01); *C07C 237/04* (2013.01); *C07C 237/20* (2013.01); *C07C 271/24* (2013.01); *C07C 323/60* (2013.01); *C07D 207/08* (2013.01); *C07D 307/88* (2013.01); *C07D 317/40* (2013.01); *C07C 2101/14* (2013.01); *C07C 2101/18* (2013.01); *C07C 2102/18* (2013.01); *C07C 2103/74* (2013.01)

(58) Field of Classification Search
CPC  C07D 207/08; C07D 307/88; C07C 323/60; C07C 237/04; C07C 271/24; C07C 237/20; C07C 2101/14; C07C 2101/18; A61K 31/357; A61K 31/265
See application file for complete search history.

(56) References Cited

U.S. PATENT DOCUMENTS

2011/0207672 A1\* 8/2011 Moher et al. ................ 514/18.3

FOREIGN PATENT DOCUMENTS

| CN | 1356971 A | 7/2002 |
| CN | 101084236 A | 12/2007 |
| EP | 1052246 | 11/2000 |

(Continued)

OTHER PUBLICATIONS

Nakazato, A., "Fluorinated Conformationally Restricted Glutamate Analogues for CNS Drug Discovery and Development." Fluorine in Medicinal Chemistry and Chemical Biology (2009): 67-97.\*

(Continued)

*Primary Examiner* — Samantha Shterengarts
*Assistant Examiner* — Matt Mauro
(74) *Attorney, Agent, or Firm* — Sughrue Mion, PLLC

(57) ABSTRACT

Provided are a fluorine-containing amino acid prodrug represented by general formula (I) that makes a fluorine-containing amino acid which is a group 2 metabotropic glutamate receptor agonist into a prodrug, or a pharmaceutically acceptable salt thereof. More specifically, provided is a prodrug that increases the in vivo exposure and enhances the oral absorbability and other mucosal absorbability of a parent compound that acts on group 2 metabotropic glutamate receptors as an agent for the treatment or prevention of diseases in which group 2 metabotropic glutamate receptors are said to be involved, such as: schizophrenia, anxiety disorder and its related diseases, depression, bipolar disorder, epilepsy, developmental disorders, sleep disorders, and other neuropsychiatric diseases; and drug dependence, cognitive disorders, Alzheimer's disease, Huntington's chorea, Parkinson's disease, movement disorders associated with muscular rigidity, cerebral ischemia, cerebral insufficiency, spinal cord disorders, cephalopathy, and other neurological diseases.

[Formula 1]

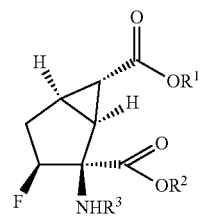

(I)

16 Claims, No Drawings

(56) References Cited

FOREIGN PATENT DOCUMENTS

| EP | 1142860 A1 | 10/2001 |
|---|---|---|
| JP | 11279129 | 10/1999 |
| JP | 2001089367 | 4/2001 |
| WO | 03104217 A2 | 12/2003 |

OTHER PUBLICATIONS

Bueno, A.B., "Dipeptides as effective prodrugs of the unnatural amino acid (+)-2-aminobicyclo [3.1. 0] hexane-2, 6-dicarboxylic acid (LY354740), a selective group II metabotropic glutamate receptor agonist." Journal of medicinal chemistry 48.16 (2005): 5305-5320.*

Takamori et al., "Antipsychotic action of selective group II metabotropic glutamate receptor agonist MGS0008 and MGS0028 on conditioned avoidance responses in the rat", Life Sciences, 73:1721-1728 (2003).

Nakazato et al., "Synthesis, SARs, and Pharmacological Characterization of 2-Amino-3 or 6-fluorobicyclo[3.1.0]hexane-2,6-dicarboxylic acid derivatives as potent, selective, and orally active group II metabotropic glutamate receptor agonists", J. Med. Chem., 43:4893-4909 (2000).

Pedragal et al., "Stereoselective Synthesis of 2-amino-3-fluoro bicyclo[3.1.0]hexane-2,6-dicarboxylic acid", Bioorganic & Medicinal Chemistry, 10:433-436 (2002).

Communication dated Jan. 27, 2016, from the State Intellectual Property Office of People's Republic of China in counterpart Application No. 201380028764.5.

Ana B. Bueno, et al., "Dipeptides as Effective Prodrugs of the Unnatural Amino Acid (+)-2-Aminobicyclo[3.1.0]hexane-2, 6-dicarboxylic Acid (LY354740), a Selective Group II Metabotropic Glutamate Receptor Agonist"; J. Med. Chem., 48, p. 5305-5320, 2005.

* cited by examiner

PRODRUG OF FLUORINE-CONTAINING AMINO ACID

This application is a National Stage of International Application No. PCT/JP2013/065202, filed on May 13, 2013, which claims priority from Japanese Patent Application Nos. 2012-126162, filed on Jun. 1, 2012, and 2013-052574, filed on Mar. 15, 2013, the contents of all of which are incorporated herein by reference in their entirety.

TECHNICAL FIELD

The present invention relates to prodrugs of (1S,2S,3S,5R,6S)-2-amino-3-fluorobicyclo[3.1.0]hexane-2,6-dicarboxylic acid, which is a metabotropic glutamate receptor agonist (hereinafter also referred to as parent compound or Compound (IV)). More specifically, the invention relates to prodrugs of the metabotropic glutamate receptor agonist (1S,2S,3S,5R,6S)-2-amino-3-fluorobicyclo[3.1.0]hexane-2,6-dicarboxylic acid that are expected to be useful as agents for treatment or prevention of diseases in which group 2 metabotropic glutamate receptors are said to be involved, such as schizophrenia, anxiety disorder and its related diseases, depression, bipolar disorder, epilepsy, developmental disorders, sleep disorders and other neuropsychiatric diseases, and drug dependence, cognitive disorders, Alzheimer's disease, Huntington's chorea, Parkinson's disease, movement disorders associated with muscular rigidity, cerebral ischemia, cerebral insufficiency, spinal cord disorders, cephalopathy and other neurological diseases.

The present invention also relates to prodrugs that are formed from the parent compound acting on metabotropic glutamate receptors and that, as a result of the formation, enhance mucosal absorbability such as oral absorbability and increase the in vivo exposure of the parent compound.

BACKGROUND ART

In recent years, successive cloning studies of the glutamate receptor gene have been conducted, with the finding that glutamate receptors have many subtypes. At present, glutamate receptors are generally divided into two categories: "ionotropic receptors having an ionic channel structure" and "metabotropic receptors coupled to G-protein". Further, ionotropic glutamate receptors are divided into three groups: NMDA, α-amino-3-hydroxy-5-methylisoxazole-4-propionate (AMPA) and kainate receptors (Non-Patent Document 1), while metabotropic glutamate receptors are divided into eight groups, mGluR1 to mGluR8 (Non-Patent Documents 2 and 3). Group 2 metabotropic glutamate receptors exist in the presynapses of the glutamatergic nervous system and function as autoreceptors, thus suppressing excessive release of glutamic acid (Non-Patent Documents 4 and 5). Since the glutamatergic nervous system is involved in various neuropsychiatric functions, it is inferred that compounds acting on group 2 metabotropic glutamate receptors may be effective for treatment or prevention of acute and chronic neuropsychiatric diseases and neurological diseases.

As a group 2 metabotropic glutamate receptor agonist, (1S,2S,3S,5R,6S)-2-amino-3-fluorobicyclo[3.1.0]hexane-2,6-dicarboxylic acid is disclosed (Patent Document 1). The $EC_{50}$ values for the agonistic activity are 29.4 nM and 45.4 nM for mGluR2 and mGluR3, respectively, and it has been confirmed that the agonist has the effect of suppressing phencyclidine-elicited hyperactivity in schizophrenia model rat, with a reported $ED_{50}$ value of 5.1 mg/kg. It also has been confirmed that the agonist has the effect of suppressing phencyclidine-elicited head-weaving behavior and conditioned avoidance response, which are schizophrenia models (Non-Patent Documents 6 and 7).

However, the oral absorbability of (1S,2S,3S,5R,6S)-2-amino-3-fluorobicyclo[3.1.0]hexane-2,6-dicarboxylic acid is poor in monkeys. This suggests the possibility that the oral absorbability may also be poor in humans.

There are mainly two approaches to improvement of the mucosal absorbability (e.g., oral absorbability) of compounds. One is a method of changing their chemical structures themselves and the other is a method of devising a means of formulation without changing their chemical structures. The former method encompasses attaching a small modifying group such as an alkyl group or an acyl group to a reactive substituent such as a hydroxyl group or amino group of compounds to form them into prodrugs.

Compounds preferred as the aforementioned prodrugs are compounds that exist stably in prodrug forms before absorption, exhibit improved absorption after being formed into prodrugs and are converted to parent compound chemically or enzymatically and rapidly in the small intestine, the liver and/or plasma during and/or after absorption.

However, it is difficult to develop ideal prodrugs that satisfy all of the aforementioned conditions. For example, prodrug derivatives having an ester bond can be more likely to be hydrolyzed, which may have a great influence on chemical stability before absorption. As for prodrug derivatives having an amide bond, a great change of the physical properties of compounds may have a great influence on mucosal absorbability such as oral absorbability. Further, an amide bond is less likely to be hydrolyzed, which may have a great influence on biotransformation of compounds to parent compounds and plasma concentrations. Furthermore, it is difficult to predict the Pharmacokinetic profiles of prodrugs because enzymes that control biotransformation of prodrugs to parent compounds are substrate-specific and particularly, for example, the steric hindrance of a substituent inserted for formation of prodrugs prevents reaction of the enzymes. For these reasons, it is by no means easy to enhance the plasma concentrations of parent compounds by estimating possible improvements in the mucosal absorbability (e.g., oral absorbability) of prodrugs and their transformation to the parent compounds.

In fact, Patent Document 1 provides general descriptions on prodrugs of (1S,2S,3S,5R,6S)-2-amino-3-fluorobicyclo[3.1.0]hexane-2,6-dicarboxylic acid, but no concrete disclosures on the prodrugs. There have been no successful examples of formation of prodrugs so far since 1999, when the application according to the patent document was filed.

CITATION LIST

Patent Document

Patent Document 1: JP H11-279129 A

Non-Patent Documents

Non-Patent Document 1: Science, 258, 59, 7-603, 1992

Non-Patent Document 2: J. Neurosci., 13, 1372-1378, 1993

Non-Patent Document 3: Neuropharmacol., 34, 1-26, 1995

Non-Patent Document 4: Neuropharmacol., 40, 20-27, 2001

Non-Patent Document 5: Eur. J. Pharmacol., 356, 149-157, 1998

Non-Patent Document 6: J. Med. Chem., 43, 4893-4909, 2000

Non-Patent Document 7: Life Science, 73, 1721-1728, 2003

SUMMARY OF INVENTION

Technical Problem

An objective of the present invention is to provide prodrugs that enhance the mucosal absorbability (e.g., oral absorbability) of the parent compound acting on group 2 metabotropic glutamate receptors and which increase the in vivo exposure of the parent compound, serving as agents for treatment or prevention of conditions in which group 2 metabotropic glutamate receptors are said to be involved, such as schizophrenia, anxiety disorder and its related conditions, depression, bipolar disorder, epilepsy, developmental disorders, sleep disorders and other neuropsychiatric conditions, and drug dependence, cognitive disorders, Alzheimer's disease, Huntington's chorea, Parkinson's disease, movement disorders associated with muscular rigidity, cerebral ischemia, cerebral insufficiency, spinal cord disorders, cephalopathy and other neurological conditions.

Solution to Problem

The inventors of the present invention conducted extensive and intensive studies on prodrugs of (1S,2S,3S,5R,6S)-2-amino-3-fluorobicyclo[3.1.0]hexane-2,6-dicarboxylic acid which is the parent compound acting on group 2 metabotropic glutamate receptors and, as a result, the inventors have found that some kinds of derivatives serving as prodrugs enhance mucosal absorbability such as oral absorbability and increase the in vivo exposure of the parent compound. This finding has led to the completion of the present invention.

The present invention is described below in detail. Embodiments of the present invention (hereinafter, the compounds of the embodiments are referred to as "Inventive Compounds") are described below.

(1) A compound represented by formula (I):

[Formula 1]

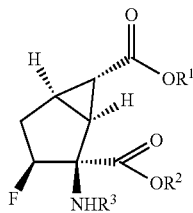

(I)

[wherein $R^1$ and $R^2$, which may be the same or different, are each a hydrogen atom, formula —$(CR^4R^{4'})$—O—CO—$R^5$ or —$(CR^6R^{6'})$—O—CO—O—$R^7$, or the following formula (IIa) or (IIb):

[Formula 2]

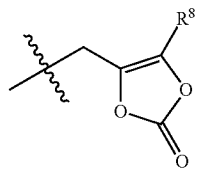

(IIa)

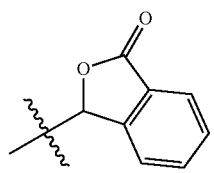

(IIb)

$R^3$ is a hydrogen atom, formula -(AA)n-H, —CO—O—$(CR^9R^{9'})$—O—CO—$R^{10}$ or —CO—O—$(CR^9R^{9'})$—O—CO—O—$R^{11}$, or the following formula (III):

[Formula 3]

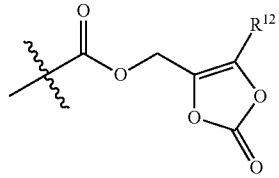

(III)

wherein $R^4$ and $R^{4'}$, which may be the same or different, are each a hydrogen atom or a $C_{1-6}$ alkyl group;

$R^5$ is a $C_{1-10}$ alkyl group, a $C_{3-8}$ cycloalkyl group (the $C_{3-8}$ cycloalkyl group being optionally substituted with one to three $C_{1-6}$ alkyl groups), an adamantyl group (the adamantyl group being optionally substituted with one to three $C_{1-6}$ alkyl groups), or a phenyl group (the phenyl group being optionally substituted with one to three groups selected from a halogen atom and a $C_{1-6}$ alkyl group);

$R^6$ and $R^{6'}$, which may be the same or different, are each a hydrogen atom or a $C_{1-6}$ alkyl group;

$R^7$ is a $C_{1-10}$ alkyl group, a $C_{3-8}$ cycloalkyl group (the $C_{3-8}$ cycloalkyl group being optionally substituted with one to three $C_{1-6}$ alkyl groups), an adamantyl group (the adamantyl group being optionally substituted with one to three $C_{1-6}$ alkyl groups), or an aryl group (the aryl group being optionally substituted with one to three groups selected from a halogen atom and a $C_{1-6}$ alkyl group);

$R^8$ is a $C_{1-6}$ alkyl group or a phenyl group;

$R^9$ and $R^{9'}$, which may be the same or different, are each a hydrogen atom or a $C_{1-6}$ alkyl group;

$R^{10}$ is a $C_{1-10}$ alkyl group, a $C_{3-8}$ cycloalkyl group (the $C_{3-8}$ cycloalkyl group being optionally substituted with one to three $C_{1-6}$ alkyl groups), an adamantyl group (the adamantyl group being optionally substituted with one to three $C_{1-6}$ alkyl groups), or a phenyl group (the phenyl group being optionally substituted with one to three groups selected from a halogen atom and a $C_{1-6}$ alkyl group);

$R^{11}$ is a $C_{1-10}$ alkyl group, a $C_{3-8}$ cycloalkyl group (the $C_{3-8}$ cycloalkyl group being optionally substituted with one to three $C_{1-6}$ alkyl groups), an adamantyl group (the adamantyl group being optionally substituted with one to three $C_{1-6}$ alkyl groups), or an aryl group (the aryl group being optionally substituted with one to three groups selected from a halogen atom and a $C_{1-6}$ alkyl group);

$R^{12}$ is a $C_{1-6}$ alkyl group or a phenyl group;

AA is an aminoacyl group; and n is an integer of 1 to 3, provided that compounds in which $R^1$, $R^2$ and $R^3$ are each a hydrogen atom are excluded] or a pharmaceutically acceptable salt thereof.

(2) The compound according to (1), wherein, in formula (I), $R^3$ is a hydrogen atom, or a pharmaceutically acceptable salt thereof.

(3) The compound according to (2), wherein, in formula (I), $R^1$ is formula —$(CR^4R^{4'})$—O—CO—$R^5$ (wherein $R^4$, $R^{4'}$ and $R^5$ are as defined in (1)) or —$(CR^6R^{6'})$—O—CO—O—$R^7$ (wherein $R^6$, $R^{6'}$ and $R^7$ are as defined in (1)) or the following formula (IIa) or (IIb):

[Formula 4]

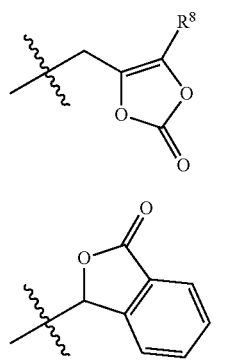

(IIa)

(IIb)

wherein $R^8$ is as defined in (1), or a pharmaceutically acceptable salt thereof.

(4) The compound according to (3), wherein, in formula (I), $R^1$ is formula —$(CR^4R^{4'})$—O—CO—$R^5$ (wherein $R^4$, $R^{4'}$ and $R^5$ are as defined in (1)) or —$(CR^6R^{6'})$—O—CO—O—$R^7$ (wherein $R^6$, $R^{6'}$ and $R^7$ are as defined in (1)), or a pharmaceutically acceptable salt thereof.

(5) The compound according to (4), wherein, in formula (I), $R^1$ is formula —$(CR^4R^{4'})$—O—CO—$R^5$ or —$(CR^6R^{6'})$—O—CO—O—$R^7$, wherein $R^5$ is an adamantyl group (the adamantyl group being optionally substituted with one to three methyl groups); $R^7$ is a $C_{3-8}$ cycloalkyl group substituted with one to three $C_{1-6}$ alkyl groups or is an adamantyl group (the adamantyl group being optionally substituted with one to three $C_{1-6}$ alkyl groups); and $R^4$, $R^{4'}$, $R^6$ and $R^{6'}$ are as defined in (1), or a pharmaceutically acceptable salt thereof.

(6) The compound according to any one of (2) to (5), wherein, in formula (I), $R^2$ is a hydrogen atom, or a pharmaceutically acceptable salt thereof.

(7) The compound according to (1), wherein, in formula (I), $R^1$ and $R^2$ are each a hydrogen atom; $R^3$ is formula -(AA)n-H, wherein AA is an aminoacyl group and n is 1 or 2, or a pharmaceutically acceptable salt thereof.

(8) The compound according to (7), wherein, in formula (I), $R^3$ is formula -(AA)n-H, wherein AA is a natural amino acid-derived aminoacyl group and n is 1, or a pharmaceutically acceptable salt thereof.

(9) A drug comprising the compound according to any one of (1) to (8) or a pharmaceutically acceptable salt thereof

(10) A drug comprising the compound according to any one of (1) to (8) or a pharmaceutically acceptable salt thereof, for prevention or treatment of a condition selected from the group consisting of schizophrenia, anxiety disorder and its related conditions, depression, bipolar disorder, epilepsy, developmental disorders, sleep disorders and other neuropsychiatric conditions, and drug dependence, cognitive disorders, Alzheimer's disease, Huntington's chorea, Parkinson's disease, movement disorders associated with muscular rigidity, cerebral ischemia, cerebral insufficiency, spinal cord disorders, cephalopathy and other neurological conditions.

Advantageous Effects of Invention

A fluorine-containing amino acid prodrug of the present invention enhances mucosal absorbability such as oral absorbability and is converted to (1S,2S,3S,5R,6S)-2-amino-3-fluorobicyclo[3.1.0]hexane-2,6-dicarboxylic acid, which is the parent compound, rapidly after absorption. The parent compound exhibits affinity for metabotropic glutamate receptors and has an agonistic effect.

DESCRIPTION OF EMBODIMENTS

Embodiments for carrying out the present invention are described specifically below.

The meanings of the terms and phrases used herein are as follows:

The "halogen atom" means a fluorine atom, a chlorine atom, a bromine atom, or an iodine atom.

The "$C_{1-6}$ alkyl group" means a linear or branched alkyl group having one to six carbon atoms, and examples include groups such as methyl, ethyl, n-propyl, isopropyl, n-butyl, isobutyl, sec-butyl, tert-butyl, n-pentyl, isopentyl, neopentyl, tert-pentyl, 1-ethylpropyl, n-hexyl, isohexyl, and neohexyl.

The "$C_{1-10}$ alkyl group" means a linear or branched alkyl group having one to ten carbon atoms, and examples include groups such as methyl, ethyl, n-propyl, isopropyl, n-butyl, isobutyl, sec-butyl, tert-butyl, n-pentyl, isopentyl, neopentyl, tert-pentyl, 1-ethylpropyl, n-hexyl, isohexyl, neohexyl, n-heptyl, n-octyl, n-nonyl, and n-decyl.

The "$C_{3-8}$ cycloalkyl group" means a group such as cyclopropyl, cyclobutyl, cyclopentyl, cyclohexyl, cycloheptyl, or cyclooctyl.

The "aryl group" means a monocyclic or bicyclic aromatic hydrocarbon, and examples include groups such as phenyl, 1-naphthyl, and 2-naphthyl.

The "aminoacyl group" means a natural or unnatural amino acid-derived aminoacyl group. The "natural amino acid" may be alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine, and each of these natural amino acids except glycine has an L-stereoisomer. The "unnatural amino acid" may be a D-stereoisomer of the aforementioned "natural amino acids" and other examples include β-alanine, aminobutyric acid, β-aminobutyric acid, γ-aminobutyric acid, hydroxyproline, sarcosine, and phenylglycine.

The "pharmaceutically acceptable salt" as referred to herein encompasses salts with inorganic acids such as sulfuric acid, hydrochloric acid, hydrobromic acid, phosphoric acid, and nitric acid; salts with organic acids such as acetic acid, benzoic acid, oxalic acid, lactic acid, malic acid, tartaric acid, fumaric acid, maleic acid, citric acid, malonic acid, mandelic acid, gluconic acid, galactaric acid, glucoheptonic acid, glycolic acid, glutamic acid, trifluoroacetic acid, methanesulfonic acid, ethanesulfonic acid, benzenesulfonic acid, p-toluenesulfonic acid, camphorsulfonic acid, and naphthalene-2-sulfonic acid; salts with one or more metal ions such as lithium ion, sodium ion, potassium ion, calcium ion, magnesium ion, zinc ion, and aluminum ion; and salts with ammonia or amines such as arginine, lysine, piperazine, choline, diethylamine, 4-phenylcyclohexylamine, 2-aminoethanol, and benzathine. These salts can be obtained by conversion from free forms in a conventional manner.

Preferred embodiments of Inventive Compounds are as follows:

In the compounds, when $R^3$ is a hydrogen atom, $R^1$ is preferably formula —$(CR^4R^{4\prime})$—O—CO—$R^5$ or —$(CR^6R^{6\prime})$—O—CO—O—$R^7$ or formula (IIa), more preferably formula —$(CR^6R^{6\prime})$—O—CO—O—$R^7$ or formula (IIa). When $R^3$ is a hydrogen atom, $R^2$ is preferably formula —$(CR^6R^{6\prime})$—O—CO—O—$R^7$ or formula (IIa).

When $R^2$ and $R^3$ are each a hydrogen atom, $R^1$ is preferably formula —$(CR^4R^{4\prime})$—O—CO—$R^5$ or —$(CR^6R^{6\prime})$—O—CO—O—$R^7$ or formula (IIa) or (IIb), more preferably formula —$(CR^4R^{4\prime})$—O—CO—$R^5$ or —$(CR^6R^{6\prime})$—O—CO—O—$R^7$.

When $R^1$ and $R^3$ are each a hydrogen atom, $R^2$ is preferably formula —$(CR^6R^{6\prime})$—O—CO—O—$R^7$ or formula (IIa).

$R^4$ is preferably a hydrogen atom.

$R^{4\prime}$ is preferably a hydrogen atom or a $C_{1-6}$ alkyl group, more preferably a hydrogen atom or a methyl group.

$R^5$ is preferably a $C_{1-10}$ alkyl group, a $C_{3-8}$ cycloalkyl group (the $C_{3-8}$ cycloalkyl group being optionally substituted with one to three $C_{1-6}$ alkyl groups), an adamantyl group (the adamantyl group being optionally substituted with one to three $C_{1-6}$ alkyl groups) or a phenyl group (the phenyl group being optionally substituted with one to three groups selected from a halogen atom and a $C_{1-6}$ alkyl group), more preferably a $C_{1-10}$ alkyl group, an adamantyl group (the adamantyl group being optionally substituted with one to three $C_{1-6}$ alkyl groups) or a phenyl group, still more preferably an adamantyl group (the adamantyl group being optionally substituted with one to three methyl groups).

$R^6$ is preferably a hydrogen atom.

$R^{6\prime}$ is preferably a hydrogen atom or a $C_{1-6}$ alkyl group, more preferably a hydrogen atom or a methyl group.

$R^7$ is preferably a $C_{1-6}$ alkyl group, a $C_{3-8}$ cycloalkyl group (the $C_{3-8}$ cycloalkyl group being optionally substituted with one to three $C_{1-6}$ alkyl groups) or an adamantyl group (the adamantyl group being optionally substituted with one to three $C_{1-6}$ alkyl groups), more preferably a $C_{3-8}$ cycloalkyl group substituted with one to three $C_{1-6}$ alkyl groups, or an adamantyl group (the adamantyl group being optionally substituted with one to three $C_{1-6}$ alkyl groups).

$R^8$ is preferably a $C_{1-6}$ alkyl group.

When $R^1$ and $R^2$ are each a hydrogen atom, $R^3$ is preferably formula -(AA)n-H.

AA is preferably a natural amino acid-derived aminoacyl group.

n is preferably 1 or 2, more preferably 1.

Preferred examples of Inventive Compounds include the following compounds or pharmaceutically acceptable salts thereof:

(1S,2S,3S,5R,6S)-6-(((adamantane-1-carbonyl)oxy)methoxy)carbonyl-2-amino-3-fluorobicyclo[3.1.0]hexane-2-carboxylic acid, (1S,2S,3S,5R,6S)-6-(1-((adamantane-1-carbonyl)oxy)ethoxy)carbonyl-2-amino-3-fluorobicyclo[3.1.0]hexane-2-carboxylic acid, (1S,2S,3S,5R,6S)-2-amino-3-fluoro-6-((1-(((((1R,2S,5R)-2-isopropyl-5-methylcyclohexyl)oxy)carbonyl)oxy)ethoxy)carbonyl)bicyclo[3.1.0]hexane-2-carboxylic acid, (1S,2S,3S,5R,6S)-2-amino-3-fluoro-6-(((((((1R,2S,5R)-2-isopropyl-5-methylcyclohexyl)oxy)carbonyl)oxy)methoxy)carbonyl)bicyclo[3.1.0]hexane-2-carboxylic acid, (1S,2S,3S,5R,6S)-2-amino-6-(1-((3,5-dimethyladamantane-1-carbonyl)oxy)ethoxy)carbonyl-3-fluorobicyclo[3.1.0]hexane-2-carboxylic acid, (1S,2S,3S,5R,6S)-2-amino-3-fluoro-6-(((octanoyloxy)methoxy)carbonyl)bicyclo[3.1.0]hexane-2-carboxylic acid, (1S,2S,3S,5R,6S)-2-amino-6-(((benzoyloxy)methoxy)carbonyl)-3-fluorobicyclo[3.1.0]hexane-2-carboxylic acid, (1S,2S,3S,5R,6S)-2-amino-6-((1-(((cyclohexyloxy)carbonyl)oxy)ethoxy)carbonyl)-3-fluorobicyclo[3.1.0]hexane-2-carboxylic acid, (1S,2S,3S,5R,6S)-2-amino-6-(1-(((cyclooctyloxy)carbonyl)oxy)ethoxy)carbonyl)-3-fluorobicyclo[3.1.0]hexane-2-carboxylic acid, (1S,2S,3S,5R,6S)-2-amino-6-((1-((((4,4-dimethylcyclohexyl)oxy)carbonyl)oxy)ethoxy)carbonyl)-3-fluorobicyclo[3.1.0]hexane-2-carboxylic acid, (1S,2S,3S,5R,6S)-6-(((((adamantan-1-yloxy)carbonyl)oxy)methoxy)carbonyl)-2-amino-3-fluorobicyclo[3.1.0]hexane-2-carboxylic acid, (1S,2S,3S,5R,6S)-6-((1-(((adamantan-1-yloxy)carbonyl)oxy)ethoxy)carbonyl)-2-amino-3-fluorobicyclo[3.1.0]hexane-2-carboxylic acid, (1S,2S,3S,5R,6S)-2-amino-3-fluoro-6-(((5-methyl-2-oxo-1,3-dioxol-4-yl)methoxy)carbonyl)bicyclo[3.1.0]hexane-2-carboxylic acid, (1S,2S,3S,5R,6S)-2-amino-3-fluorobicyclo[3.1.0]hexane-2,6-dicarboxylic acid 6-(3-phthalidyl) ester, (1S,2S,3S,5R,6S)-2-((S)-2-amino-4-(methylthio)butanamide)-3-fluorobicyclo[3.1.0]hexane-2,6-dicarboxylic acid, (1S,2S,3S,5R,6S)-2-((S)-2-aminopropanamide)-3-fluorobicyclo[3.1.0]hexane-2,6-dicarboxylic acid, (1S,2S,3S,5R,6S)-2-(2-aminoacetamide)-3-fluorobicyclo[3.1.0]hexane-2,6-dicarboxylic acid, (1S,2S,3S,5R,6S)-2-((S)-2-amino-4-methylbutanamide)-3-fluorobicyclo[3.1.0]hexane-2,6-dicarboxylic acid, (1S,2S,3S,5R,6S)-2-((S)-2,6-diaminohexanamide)-3-fluorobicyclo[3.1.0]hexane-2,6-dicarboxylic acid, (1S,2S,3S,5R,6S)-2-((S)-2-amino-4-methylpentanamide)-3-fluorobicyclo[3.1.0]hexane-2,6-dicarboxylic acid, (1S,2S,3S,5R,6S)-2-((S)-2-((S)-2-aminopropanamide)propanamide)-3-fluorobicyclo[3.1.0]hexane-2,6-dicarboxylic acid, (1S,2S,3S,5R,6S)-2-((S)-2-amino-3-phenylpropanamide)-3-fluorobicyclo[3.1.0]hexane-2,6-dicarboxylic acid, (1S,2S,3S,5R,6S)-2-amino-3-fluoro-6-(((S)-1-(((((1R,2S,5R)-2-isopropyl-5-methylcyclohexyl)oxy)carbonyl)oxy)ethoxy)carbonyl)bicyclo[3.1.0]hexane-2-carboxylic acid, (1S,2S,3S,5R,6S)-2-amino-3-fluoro-6-(((R)-1-(((((1R,2S,5R)-2-isopropyl-5-methylcyclohexyl)oxy)carbonyl)oxy)ethoxy)carbonyl)bicyclo[3.1.0]hexane-2-carboxylic acid, (1S,2S,3S,5R,6S)-6-(((S)-1-((adamantane-1-carbonyl)oxy)ethoxy)carbonyl)-2-amino-3-fluorobicyclo[3.1.0]hexane-2-carboxylic acid, and (1S,2S,3S,5R,6S)-6-(((R)-1-((adamantane-1-carbonyl)oxy)
ethoxy)carbonyl)-2-amino-3-fluorobicyclo[3.1.0]hexane-
2-carboxylic acid.

When Inventive Compounds form hydrates or solvates, such hydrates and solvates are also included in the scope of the present invention. Pharmaceutically acceptable salts of hydrates or solvates of Inventive Compounds are also included in the scope of the invention.

Inventive Compounds encompass all of forms such as enantiomers, diastereomers, equilibrium compounds, mixtures thereof in any proportions, and racemates.

Inventive Compounds also encompass those in which one or more hydrogen atoms, carbon atoms, nitrogen atoms, oxygen atoms, or fluorine atoms have been replaced by their radioisotopes or stable isotopes. These labeled compounds are useful in, for example, studies of metabolism and pharmacokinetics, or biological analyses in which they are used as receptor ligands.

Inventive Compounds may be combined with one or more pharmaceutically acceptable carriers, excipients or diluents to formulate pharmaceutical preparations. Examples of the carriers, excipients and diluents include water, lactose, dextrose, fructose, sucrose, sorbitol, mannitol, polyethylene glycol, propylene glycol, starch, gum, gelatin, alginate, calcium silicate, calcium phosphate, cellulose, water syrup, methylcellulose, polyvinylpyrrolidone, alkyl parahydroxybenzoates, talc, magnesium stearate, stearic acid, glycerin, and various oils such as sesame oil, olive oil and soybean oil.

After being mixed with such carriers, excipients or diluents and, as needed, common additives such as extenders, binders, disintegrants, pH regulators or solubilizers, Inventive Compounds may be formulated by common pharmaceutical techniques into oral or parenteral drugs, such as tablets, pills, capsules, granules, powders, solutions, emulsions, suspensions, ointments, injections or skin patches, and especially formulated as prodrugs of group 2 metabotropic glutamate receptor agonist.

Inventive Compounds may be orally or parenterally administered to adult patients in an amount of 0.01 to 500 mg as a single dose or in divided doses per day, but oral administration is preferred in terms of easy medication and drug efficacy. This dosage may be increased or decreased as appropriate for the type of disease to be treated, the age, body weight and symptom of the patients, etc.

Inventive Compounds (I) do not influence group 2 metabotropic glutamate receptors. However, Inventive Compounds (I) are each hydrolyzed in vivo enzymatically or chemically into Compound (IV) which has a strong action on group 2 metabotropic glutamate receptors. Accordingly, Inventive Compounds perform functions as drugs that act on group 2 metabotropic glutamate receptors.

[Formula 5]

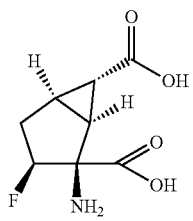

(IV)

That is, Inventive Compounds act as prodrugs that enhance the mucosal absorbability (e.g., oral absorbability) of parent compound (IV) acting on group 2 metabotropic glutamate receptors and which increase the in vivo exposure of the parent compound, serving as agents for treatment or prevention of conditions in which group 2 metabotropic glutamate receptors are said to be involved, such as schizophrenia, anxiety disorder and its related conditions, depression, bipolar disorder, epilepsy, developmental disorders, sleep disorders and other neuropsychiatric conditions, and drug dependence, cognitive disorders, Alzheimer's disease, Huntington's chorea, Parkinson's disease, movement disorders associated with muscular rigidity, cerebral ischemia, cerebral insufficiency, spinal cord disorders, cephalopathy and other neurological conditions.

Representative production processes for Inventive Compounds (I) are depicted by Schemes 1 to 7 shown below. The following processes are examples of production processes for Inventive Compounds and are by no means intended to limit the scope of the present invention. In the following examples of processes, the compounds may form salts that do not interfere with reaction.

An Inventive Compound represented by formula (I-1) may be produced by the synthetic process depicted by Scheme 1.

Scheme 1

<Scheme 1>

[Formula 6]

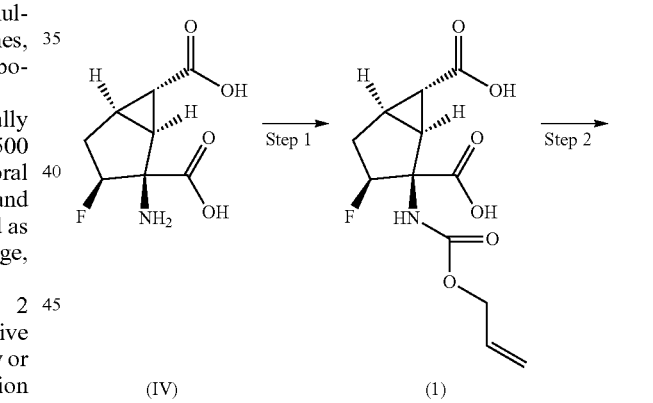

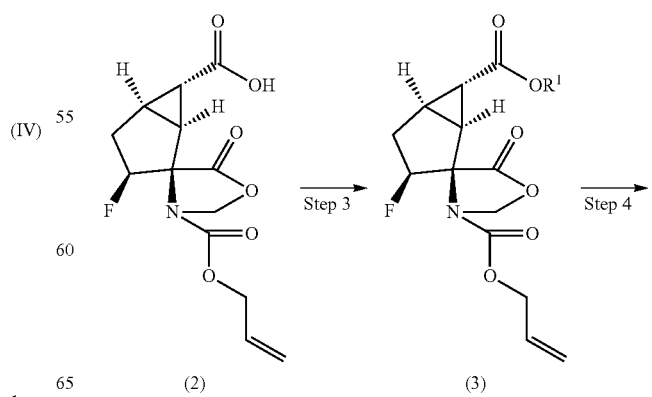

-continued

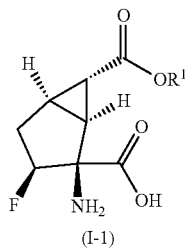

(I-1)

wherein R[1] is as defined above.

Step 1: Compound (IV) may be converted to Compound (1) through common protection of the amino group of Compound (IV) with an allyloxycarbonyl group (see Protective Groups in Organic Synthesis, fourth edition, John Wiley & Sons, Inc.). This conversion may be accomplished, for example, through reaction with allyl chloroformate in an inert solvent such as a hydrocarbon solvent (e.g., benzene, toluene, hexane), a halogenated solvent (e.g., dichloromethane, chloroform, carbon tetrachloride), an ether solvent (e.g., tetrahydrofuran, diethyl ether, 1,2-dimethoxyethane), an amide (e.g., N,N-dimethylformamide, N-methyl-2-pyrrolidinone), dimethyl sulfoxide, water or any mixture thereof, in the presence or absence of an organic base (e.g., triethylamine, pyridine, N-methylmorpholine, diisopropylethylamine, 4-(N,N-dimethylamino)pyridine, 2,6-di-t-butylpyridine) or an inorganic base (e.g., potassium carbonate, sodium carbonate, sodium bicarbonate).

Step 2: Compound (1) may be converted to Compound (2), for example, through reaction using an acid catalyst such as p-toluenesulfonic acid or oxalic acid with or without a dehydrator such as a Dean-Stark water separator, in an inert solvent such as a hydrocarbon solvent (e.g., benzene, toluene, hexane), a halogenated solvent (e.g., dichloromethane, chloroform, carbon tetrachloride), an ether solvent (e.g., tetrahydrofuran, diethyl ether, 1,2-dimethoxyethane) or any mixture thereof, in the presence of an aldehyde such as paraformaldehyde.

Step 3: Compound (2) may be converted to Compound (3) through reaction with a compound of formula L-R[1] (wherein L is a leaving group such as a halogen atom, a p-toluenesulfonyloxy group, a methanesulfonyloxy group, or a trifluoromethanesulfonyloxy group) in the presence or absence of a suitable activator such as sodium iodide, in an inert solvent such as a hydrocarbon solvent (e.g., benzene, toluene, hexane, cyclohexane), a halogenated solvent (e.g., dichloromethane, chloroform, carbon tetrachloride), an ether solvent (e.g., tetrahydrofuran, diethyl ether, 1,2-dimethoxyethane), an amide (e.g., N,N-dimethylformamide, N-methyl-2-pyrrolidinone), dimethyl sulfoxide or any mixture thereof, in the presence of an inorganic base (e.g., sodium hydride, potassium hydride, potassium carbonate, sodium carbonate, sodium bicarbonate, cesium carbonate, cesium bicarbonate, sodium hydroxide, potassium hydroxide), a metal amide (e.g., lithium bis(trimethylsilyl)amide, lithium diisopropylamide, sodium amide), an organic base (e.g., triethylamine, pyridine, diisopropylethylamine, 4-(N,N-dimethylamino)pyridine, 2,6-di-t-butylpyridine) or a base (e.g., potassium t-butoxide). Preferably, Compound (2) may be converted to Compound (3) through reaction with a compound of formula Cl—R[1] or Br—R[1] in N,N-dimethylformamide in the presence of potassium carbonate and sodium iodide at room temperature to 80° C. for 2 hours to 1 day. Alternatively, Compound (2) may be converted to Compound (3) through reaction with a compound of formula Cl—R[1] or Br—R[1] in N,N-dimethylformamide in the presence of cesium carbonate at room temperature to 80° C. for 2 hours to 1 day.

Step 4: Compound (3) may be converted to Compound (I-1), an Inventive Compound, through common deprotection of the amino group of Compound (3) (see Protective Groups in Organic Synthesis, fourth edition, John Wiley & Sons, Inc.). This conversion may be accomplished, for example, through deprotection of the α-amino acid moiety in the presence of a zero-valent palladium catalyst such as tetrakis(triphenylphosphine)palladium(0) and a regeneration reagent for metal catalyst, such as 1,3-dimethylbarbituric acid, for example, in an inert solvent such as a hydrocarbon solvent (e.g., benzene, toluene, hexane), a halogenated solvent (e.g., dichloromethane, chloroform, carbon tetrachloride), an ether solvent (e.g., tetrahydrofuran, diethyl ether, 1,2-dimethoxyethane) or any mixture thereof. Preferably, Compound (3) may be converted to Inventive Compound (I-1) through reaction performed in chloroform in the presence of tetrakis(triphenylphosphine)palladium(0) and 1,3-dimethylbarbituric acid at room temperature to 50° C. for 2 to 8 hours.

An Inventive Compound represented by formula (I-2) may be produced by the synthetic process depicted by Scheme 2.

Scheme 2

<Scheme 2>

[Formula 7]

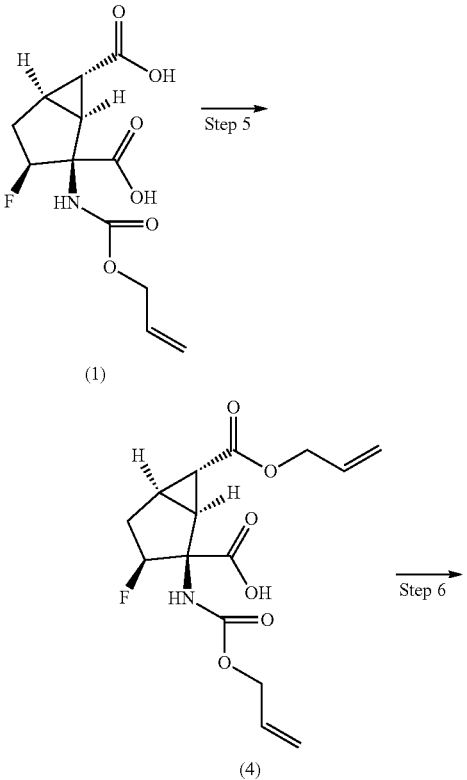

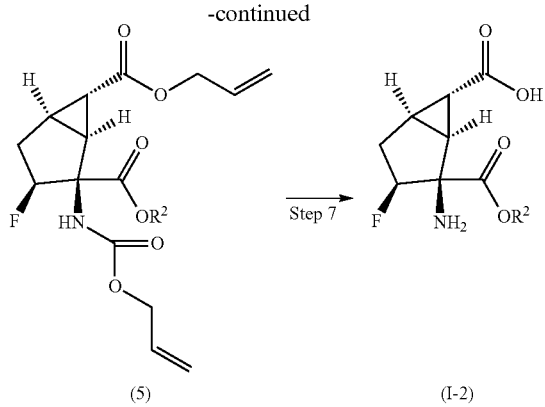

(5)    (I-2)

wherein $R^2$ is as defined above.

Step 5: Compound (1) may be converted to Compound (4) through common esterification of a carboxyl group of Compound (1) with allyl alcohol in control of time and/or reaction temperature (see Comprehensive Organic Transformations, Second Edition, 1999, John Wiley & Sons, Inc.). This esterification is, for example, a reaction performed in an inert solvent in the presence or absence of a base, such as condensation using a condensing agent such as O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU), N,N'-dicyclohexylcarbodiimide (DCC), 1-ethyl-3-(3-dimethylaminopropyl)carbodiimide hydrochloride (EDC.HCl), diphenylphosphoryl azide (DPPA) or carbonyldiimidazole (CDI), condensation with a mixed acid anhydride using ethyl chloroformate, isobutyl chloroformate, trimethylacetyl chloride, etc., or condensation with an acid halide using thionyl chloride, oxalyl chloride, 1-chloro-N,N,2-trimethyl-1-propenylamine, etc. In the esterification using a condensing agent, an additive such as 1-hydroxybenzotriazole (HOBt) or hydroxysuccinimide (HOSu) may be used as needed. Preferably, Compound (1) may be converted to Compound (4) through reaction with 1 to 1.5 equivalents of allyl alcohol in chloroform in the presence of diisopropylethylamine, 4-(N,N-dimethylamino)pyridine and 1-ethyl-3-(3-dimethylaminopropyl)carbodiimide hydrochloride (EDC.HCl) at room temperature for 1 to 4 days.

Step 6: Compound (4) may be converted to Compound (5) in the same manner as in Step 3. Preferably, Compound (4) may be converted to Compound (5) through reaction with a compound of formula Cl—$R^2$ or Br—$R^2$ in N,N-dimethylformamide in the presence of potassium carbonate and sodium iodide at room temperature to 80° C. for 2 hours to 1 day. Alternatively, Compound (4) may be converted to Compound (5) through reaction with a compound of formula Cl—$R^2$ or Br—$R^2$ in N,N-dimethylformamide in the presence of cesium carbonate at room temperature to 80° C. for 2 hours to 1 day.

Step 7: Compound (5) may be converted to Compound (I-2), an Inventive Compound, through deprotection of the protecting groups for the amino group and the carboxyl group at the 6-position, respectively, in the same manner as in Step 4. Preferably, Compound (5) may be converted to Inventive Compound (I-2) through reaction performed in chloroform in the presence of tetrakis(triphenylphosphine)palladium(0) and 1,3-dimethylbarbituric acid at room temperature to 50° C. for 2 to 8 hours.

An Inventive Compound represented by formula (I-3) may be produced by the synthetic process depicted by Scheme 3.

Scheme 3

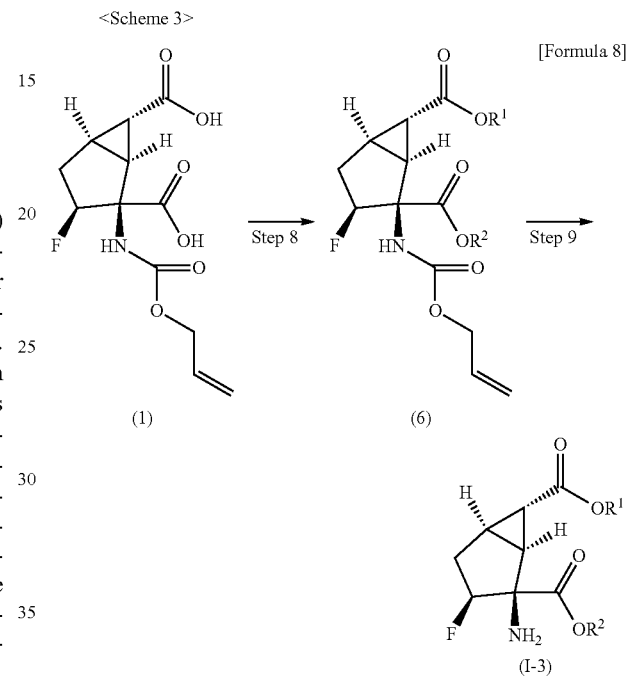

wherein $R^1=R^2$ and $R^1$ and $R^2$ are as defined above.

Step 8: Compound (1) may be converted to Compound (6) in the same manner as in Step 3. Preferably, Compound (1) may be converted to Compound (6) through reaction with a compound of formula Cl—$R^1$ or Br—$R^1$ in N,N-dimethylformamide in the presence of potassium carbonate and sodium iodide at room temperature to 80° C. for 2 hours to 1 day. Alternatively, Compound (1) may be converted to Compound (6) through reaction with a compound of formula Cl—$R^1$ or Br—$R^1$ in N,N-dimethylformamide in the presence of cesium carbonate at room temperature to 80° C. for 2 hours to 1 day.

Step 9: Compound (6) may be converted to Compound (I-3), an Inventive Compound, through deprotection of the protecting group for the amino group in the same manner as in Step 4. Preferably, Compound (6) may be converted to Inventive Compound (I-3) through reaction performed in chloroform in the presence of tetrakis(triphenylphosphine)palladium(0) and 1,3-dimethylbarbituric acid at room temperature to 50° C. for 2 to 8 hours.

An Inventive Compound represented by formula (1-4) may be produced by the synthetic process depicted by Scheme 4.

Scheme 4

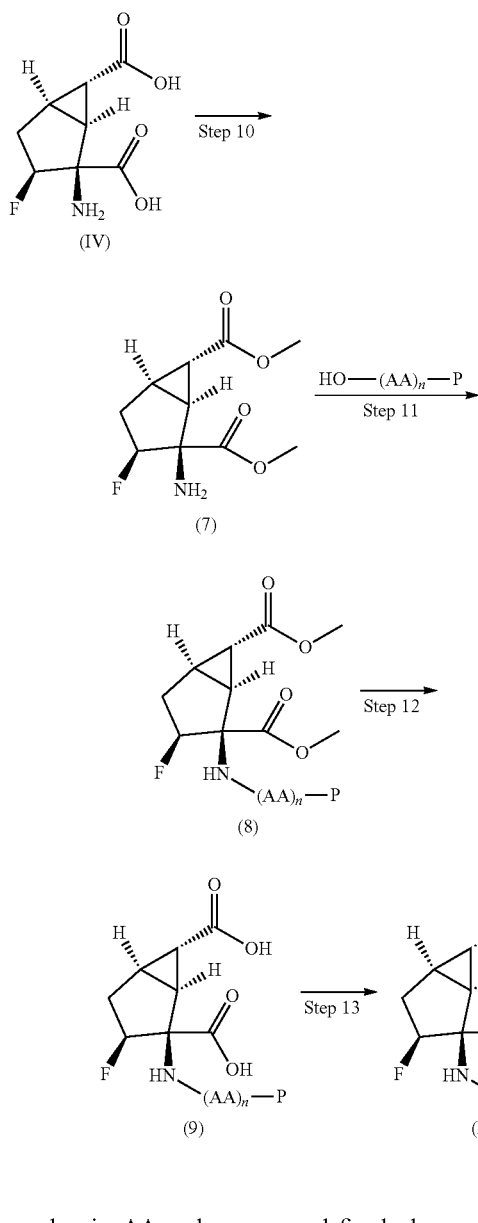

[Formula 9]

wherein AA and n are as defined above and P is a protecting group for the amino group.

Step 10: Compound (IV) may be converted to Compound (7) through common esterification of the carboxyl groups of Compound (IV) (see Protective Groups in Organic Synthesis, fourth edition, John Wiley & Sons, Inc.). Preferably, Compound (IV) may be converted to Compound (7) through reaction performed in a methanol solution containing 5 to 10% hydrogen chloride at room temperature to 80° C. for 2 hours to 3 days.

Step 11: Compound (7) may be converted to Compound (8) through common amidation of the amino group of Compound (7). This amidation is, for example, a reaction performed in an inert solvent in the presence or absence of a base, such as condensation using a condensing agent such as O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU), N,N'-dicyclohexylcarbodiimide (DCC), 1-ethyl-3-(3-dimethylaminopropyl)carbodiimide hydrochloride (ED-C.HCl), diphenylphosphoryl azide (DPPA) or carbonyldiimidazole (CDI), condensation with a mixed acid anhydride using ethyl chloroformate, isobutyl chloroformate, trimethylacetyl chloride, etc., or condensation with an acid halide using thionyl chloride, oxalyl chloride, 1-chloro-N,N,2-trimethyl-1-propenylamine, etc. In the amidation using a condensing agent, an additive such as 1-hydroxybenzotriazole (HOBt) or hydroxysuccinimide (HOSu) may be used as needed. Preferably, Compound (7) may be converted to Compound (8) through reaction performed in chloroform in the presence of N-methylmorpholine, isobutyl chloroformate and the compound HO-(AA)-P at −40° C. to 60° C. for 20 minutes to 1 day.

Step 12: Compound (8) may be converted to Compound (9) through common hydrolysis of the methylesters of Compound (8) into carboxylic acids (see T. W. Greene, P. G. M. Wuts, "Protective Groups in Organic Synthesis"). Preferably, Compound (8) may be converted to Compound (9) through reaction performed in tetrahydrofuran and a 0.1 to 10 mol/L aqueous sodium hydroxide solution at −10° C. to 40° C. for 2 hours to 2 days.

Step 13: Compound (9) may be converted to Compound (I-4), an Inventive Compound, through common deprotection of the protecting group for the amino group of Compound (9) to remove the protecting group (see Protective Groups in Organic Synthesis, fourth edition, John Wiley & Sons, Inc.).

An Inventive Compound represented by formula (I-5) may be produced by the synthetic process depicted by Scheme 5.

Scheme 5

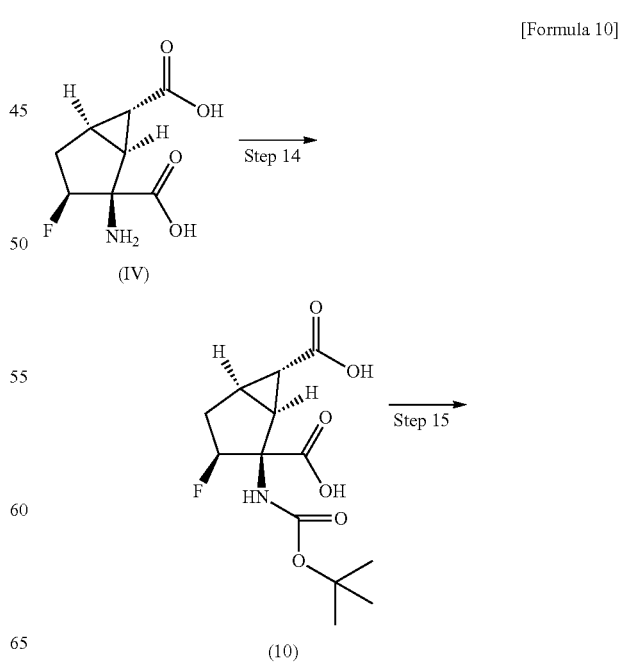

[Formula 10]

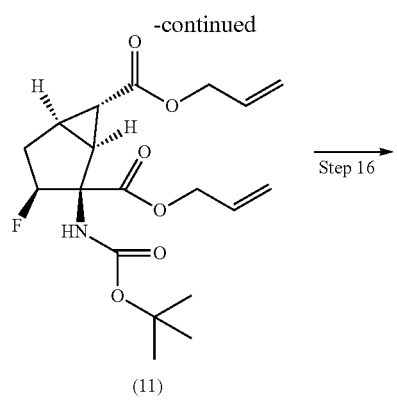

(11)

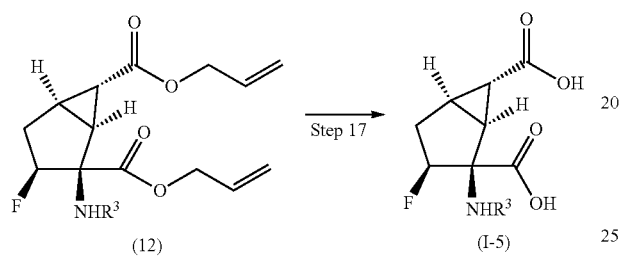

(12)     (I-5)

wherein $R^3$ is a structure of formula —CO—O—$(CR^9R^{9'})$—O—CO—$R^{10}$ or —CO—O—$(CR^9R^{9'})$—O—CO—O—$R^{11}$ or formula (III), and $R^9$, $R^{9'}$, $R^{10}$, $R^{11}$ and formula (III) are as defined above.

Step 14: Compound (IV) may be converted to Compound (10) in the same manner as in Step 1. Preferably, Compound (IV) may be converted to Compound (10) through reaction with 1 to 5 equivalents of di-tert-butoxycarbonyl (Boc$_2$O) in 1,4-dioxane in the presence of a 1 mol/L aqueous sodium hydroxide solution at room temperature for 6 hours to 5 days.

Step 15: Compound (10) may be converted to Compound (11) through reaction of the carboxyl groups of Compound (10) in the same manner as in Step 5. Preferably, Compound (10) may be converted to Compound (11) through reaction with 2 to 5 equivalents of allyl bromide in N,N-dimethylformamide in the presence of potassium carbonate and allyl bromide at 0 to 80° C. for 2 hours to 2 days.

Step 16: Compound (11) may be converted to Compound (12) through deprotection of the amino group of Compound (11) and subsequent protection with an acyl group in the same manner as in Step 14 (see Protective Groups in Organic Synthesis, fourth edition, John Wiley & Sons, Inc.). Preferably, Compound (11) may be converted to Compound (12) through reaction performed in a 1 to 4 mol/L hydrogen chloride-ethyl acetate solution at −20° C. to 40° C. for 30 minutes to 1 day to remove the tert-butoxycarbonyl group and subsequent reaction with carbon dioxide and the compound L-$R^3$ in N,N-dimethylformamide in the presence of cesium carbonate at −20° C. to 60° C. for 1 hour to 1 day. Alternatively, Compound (11) may be converted to Compound (12) through reaction performed in a 1 to 4 mol/L hydrogen chloride-ethyl acetate solution at −20° C. to 40° C. for 30 minutes to 1 day to remove the tert-butoxycarbonyl group and subsequent reaction with the compound HO-(IIa) in chloroform in the presence of N,N-diisopropylethylamine and triphosgene at −10° C. to 40° C. for 1 hour to 1 day.

Step 17: Compound (12) may be converted to Compound (I-5), an Inventive Compound, through deprotection of the protecting groups for the carboxyl groups at the 2- and 6-positions, respectively, in the same manner as in Step 4. Preferably, Compound (12) may be converted to Inventive Compound (I-5) through reaction performed in chloroform in the presence of tetrakis(triphenylphosphine)palladium(0) and 1,3-dimethylbarbituric acid at room temperature to 50° C. for 2 to 8 hours.

An Inventive Compound represented by formula (I-6) may be produced by the synthetic process depicted by Scheme 6.

Scheme 6

<Scheme 6>

[Formula 11]

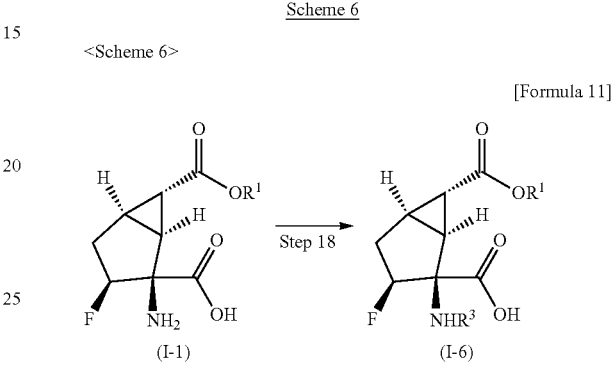

(I-1)     (I-6)

wherein $R^1$ is as defined above; $R^3$ is a structure of formula —CO—O—$(CR^9R^{9'})$—O—CO—$R^{10}$ or —CO—O—$(CR^9R^{9'})$—O—CO—O—$R^{11}$ or formula (III); and $R^9$, $R^{9'}$, $R^{10}$, $R^{11}$ and formula (III) are as defined above.

Step 18: Compound (I-1) may be converted to Inventive Compound (I-6) in the same manner as in Step 14. Preferably, Compound (I-1) may be converted to Inventive Compound (I-6) through reaction with carbon dioxide and a compound of formula L-$(CR^9R^{9'})$—O—CO—$R^{10}$ or L-$(CR^9R^{9'})$—O—CO—O—$R^{11}$ (in each formula, L is the aforementioned leaving group) in N,N-dimethylformamide in the presence of cesium carbonate at −20° C. to 60° C. for 1 hour to 1 day. Alternatively, Compound (I-1) may be converted to Inventive Compound (I-6) through reaction with the compound HO-(IIa) in chloroform in the presence of N,N-diisopropylethylamine and triphosgene at −10° C. to 40° C. for 1 hour to 1 day.

Scheme 7

<Scheme 7>

[Formula 12]

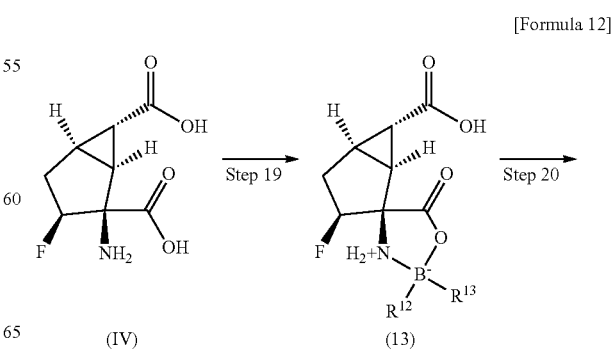

(IV)     (13)

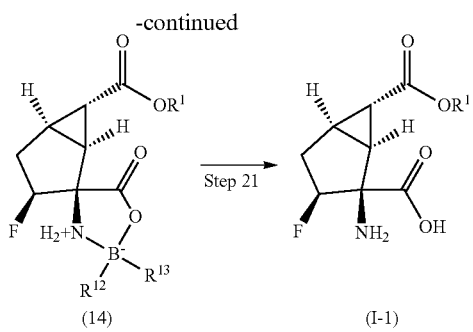

wherein $R^1$ is as defined above and $R^{12}$ and $R^{13}$, which may be the same or different, are each a hydrogen atom, a halogen atom, a $C_{1-6}$ alkyl group, a $C_{3-8}$ cycloalkyl group, an aryl group, or a heteroaryl group (the aryl group or the heteroaryl group being optionally substituted with one to three groups selected from a halogen atom and a $C_{1-6}$ alkyl group), or $R^{12}$ and $R^{13}$ may be bonded together with the adjacent boron atom to form a 5- to 8-membered saturated heterocyclic ring (the 5- to 8-membered saturated heterocyclic ring being optionally crosslinked via $C_{1-6}$ alkylene between two different carbon atoms in the ring).

Step 19: Compound (IV) may be converted to Compound (13) through common protection of the α-amino acid moiety of Compound (IV) with a boron group (see Protective Groups in Organic Synthesis, fourth edition, John Wiley & Sons, Inc.). This conversion may be accomplished, for example, through reaction with a boron reagent such as triethylborane, sodium tetraphenylborate, 9-borabicyclo[3.3.1]nonane dimer or boron trifluoride, in an inert solvent such as a hydrocarbon solvent (e.g., benzene, toluene, hexane), a halogenated solvent (e.g., dichloromethane, chloroform, carbon tetrachloride), an ether solvent (e.g., tetrahydrofuran, diethyl ether, 1,2-dimethoxyethane), an amide (e.g., N,N-dimethylformamide, N-methyl-2-pyrrolidinone), dimethyl sulfoxide or any mixture thereof at −20° C. to 100° C. for 1 hour to 2 days. Preferably, Compound (IV) may be converted to Compound (13) through reaction with triethylborane in tetrahydrofuran at 0 to 80° C. for 2 hours to 1 day.

Step 20: Compound (13) may be converted to Compound (14) through reaction with a compound of formula L-$R^1$ (wherein L is a leaving group such as a halogen atom, a p-toluenesulfonyloxy group, a methanesulfonyloxy group, or a trifluoromethanesulfonyloxy group) in the presence or absence of a suitable activator such as sodium iodide or 18-crown-6, in an inert solvent such as a hydrocarbon solvent (e.g., benzene, toluene, hexane, cyclohexane), a halogenated solvent (e.g., dichloromethane, chloroform, carbon tetrachloride), an ether solvent (e.g., tetrahydrofuran, diethyl ether, 1,2-dimethoxyethane), an amide (e.g., N,N-dimethylformamide, N-methyl-2-pyrrolidinone), dimethyl sulfoxide or any mixture thereof, in the presence of an inorganic base (e.g., sodium hydride, potassium hydride, potassium carbonate, sodium carbonate, sodium bicarbonate, cesium carbonate, cesium bicarbonate, sodium hydroxide, potassium hydroxide), a metal amide (e.g., lithium bis(trimethylsilyl)amide, lithium diisopropylamide, sodium amide), an organic base (e.g., triethylamine, pyridine, diisopropylethylamine, 4-(N,N-dimethylamino)pyridine, 2,6-di-t-butylpyridine) or a base (e.g., potassium t-butoxide). Preferably, Compound (13) may be converted to Compound (14) through reaction with a compound of formula Cl—$R^1$ or Br—$R^1$ in dimethyl sulfoxide in the presence of potassium carbonate and 18-crown-6 at room temperature to 80° C. for 2 hours to 1 day.

Step 21: Compound (14) may be converted to Inventive Compound (I-1) through common deprotection of the α-amino acid moiety of Compound (14) (see Protective Groups in Organic Synthesis, fourth edition, John Wiley & Sons, Inc.). This conversion may be accomplished, for example, through deprotection of the α-amino acid moiety in the presence of an acidic regent such as hydrogen chloride, para-toluenesulfonic acid or benzenesulfonic acid, for example, in an inert solvent such as a hydrocarbon solvent (e.g., benzene, toluene, hexane), a halogenated solvent (e.g., dichloromethane, chloroform, carbon tetrachloride), an ether solvent (e.g., tetrahydrofuran, diethyl ether, 1,2-dimethoxyethane), an ester (e.g., ethyl acetate, isopropyl acetate), an amide (e.g., N,N-dimethylformamide, N-methyl-2-pyrrolidinone), dimethyl sulfoxide, water or any mixture thereof. Preferably, Compound (14) may be converted to Inventive Compound (I-1) through reaction performed in ethyl acetate in the presence of benzenesulfonic acid or hydrogen chloride at room temperature to 50° C. for 2 hours to 1 day.

EXAMPLES

The present invention is described below in more detail by means of reference examples, examples and tests which are not intended to limit the scope of the invention and may be modified unless they depart from the scope of the invention.

The "silica gel cartridges" used in the purification by column chromatography in the reference examples and the examples are Biotage (registered trademark) SNAPCartridge KP-Sil and SNAPCartridge HP-Sil, which are products of Biotage. For the "reverse-phase column chromatography" in the purification carried out by reverse-phase column chromatography, YMC-Actus Triart C18, 5.0 μm, ϕ30×50 mm was used. The TLC silica gel plates used in the purification by TLC are Silica gel 60F254 plates (Merck).

The instrument data shown in the examples were obtained by measurement with the following instruments.

LCMS spectrum: Shimadzu LCMS-IT-TOF, Shimadzu LCMS-2010EV, Micromass Platform LC, Micromass GCT, Agilent 6150, Agilent 1290 Infinity, and Agilent 1100

NMR spectrum: [$^1$H-NMR] 600 MHz: JNM-ECA600 (JEOL Ltd.), 500 MHz: JNM-ECA500 (JEOL Ltd.)

X-ray structure analysis: R-AXIS RAPID II (Rigaku Corp.)

Melting point: Thermo plus EVO TG 8120 (Rigaku Corp.), which is a differential thermal analyzer (TG-DTA)

In the examples, compounds were named using ACD/Name (ACD/Labs 12.0, Advanced Chemistry Development Inc.).

The abbreviations shown in nuclear magnetic resonance (NMR) spectra used in the examples are as follows:

s: singlet, d: doublet, t: triplet, q: quartet, dd: double doublet, qd: quartet doublet, ddd: double double doublet, ddt: double double triplet, dddd: double double double doublet, m: multiplet, br: broad, J: coupling constant, Hz: hertz, DMSO-d6: deuterated dimethyl sulfoxide All of δ values are expressed in ppm.

Reference Example 1

Synthesis of (1S,2S,3S,5R,6S)-2-amino-6-(ethoxycarbonyl)-3-fluorobicyclo[3.1.0]hexane-2-carboxylic acid (Reference Example 1)

(1) (1S,2S,3S,5R,6S)-3'-Allyl 6-ethyl 3-fluoro-5'-oxospiro[bicyclo[3.1.0]hexan-2,4'-oxazolidine]-3',6-dicarboxylate (Reference Example 1-1)

To a suspension of (1S,2S,3S,5R,6S)-3'-((allyloxy)carbonyl)-3-fluoro-5'-oxospiro[bicyclo[3.1.0]hexan-2,4'-oxazolidine]-6-carboxylic acid obtained below in Example A-1 (A-1-2, 200 mg) in N,N-dimethylformamide (6 mL), cesium carbonate (261 mg) was added, and the mixture was stirred at room temperature for 30 minutes. Ethyl tosylate (201 mg) was added and the mixture was stirred at room temperature for 1 hour. To the reaction mixture, water was added, and the mixture was extracted twice with ethyl acetate. The combined organic layer was washed once with water and once with brine, sequentially, and then the ethyl acetate layer was dried over anhydrous sodium sulfate. The insoluble was filtered off, the filtrate was concentrated under reduced pressure, and the resulting residue was purified by silica gel column chromatography (silica gel cartridge, hexane:ethyl acetate=100:0-50:50) to give (1S,2S,3S,5R,6S)-3'-allyl 6-ethyl 3-fluoro-5'-oxospiro[bicyclo[3.1.0]hexan-2,4'-oxazolidine]-3',6-dicarboxylate (Reference Example 1-1, 68 mg) as a colorless amorphous.

$^1$H NMR (600 MHz, CHLOROFORM-d) δ=6.01-5.92(m, 1H), 5.60(d, J=4.5 Hz, 1H), 5.37-5.30(m, 1H), 5.29-5.21(m, 2H), 4.77-4.62(m, 3H), 4.20-4.12(m, 2H), 2.62-2.46(m, 2H), 2.37-2.25(m, 1H), 2.22-2.17(m, 1H), 1.27(t, J=1.0 Hz, 3H).

MS m/z; 350([M+Na]$^+$)

(2) (1S,2S,3S,5R,6S)-2-Amino-6-(ethoxycarbonyl)-3-fluorobicyclo[3.1.0]hexane-2-carboxylic acid (Reference Example 1)

(1S,2S,3S,5R,6S)-3'-Allyl 6-ethyl 3-fluoro-5'-oxospiro[bicyclo[3.1.0]hexan-2,4'-oxazolidine]-3',6-dicarboxylate (Reference Example 1-1, 68 mg) was treated in the same manner as in Example A-1 (4) below to give the title compound (Reference Example 1, 28 mg) as a colorless solid.

$^1$H NMR (600 MHz, DMSO-d6) δ=4.90-4.72(m, 1H), 4.12-3.95(m, 2H), 2.65-2.51(m, 1H), 2.15-1.82(m, 4H), 1.19 (t, J=7.2 Hz, 3H).

MS m/z; 232([M+H]$^+$)

Reference Example 2

Synthesis of (1S,2S,3S,5R,6S)-2-amino-3-fluorobicyclo[3.1.0]hexane-2,6-dicarboxylic acid (IV)

(1) (1S,2S,3S,5R,6S)-Ethyl 2-amino-2-cyano-3-fluorobicyclo[3.1.0]hexane-6-carboxylate (Reference Example 2-1)

To a solution of (1S,3S,5R,6S)-ethyl 3-fluoro-2-oxobicyclo[3.1.0]hexane-6-carboxylate (WO 2000/37410 pamphlet, 37.17 g) in 8 mol/L ammonia-methanol (250 mL), tetraisopropyl orthotitanate (68.09 g) and trimethylsilyl cyanide (23.03 g) were added dropwise sequentially while cooling on ice. The mixture was stirred on ice for 3.5 hours and then a 12.4% aqueous disodium citrate solution (848 g) was added dropwise to the reaction solution. The mixture was extracted twice with toluene (743 ml) and then the combined organic layer was dried over anhydrous sodium sulfate. The insoluble was collected by filtration and then washed with toluene (186 mL), and the solution containing (1S,2S,3S,5R,6S)-ethyl 2-amino-2-cyano-3-fluorobicyclo[3.1.0]hexane-6-carboxylate (Reference Example 2-1) was used for the next reaction without concentration and purification of the filtrate.

$^1$H NMR (600 MHz, CHLOROFORM-d) δ=4.84(dd, J=5.6, 48.0 Hz, 1H), 4.13(qd, J=7.4, 2.5 Hz, 2H), 2.59-2.49 (m, 1H), 2.46-2.45(m, 1H), 2.36(dd, J=7.6, 15.9 Hz, 1H), 2.09(br s, 1H), 2.02-2.01(m, 1H), 1.81(br s, 2H), 1.27(t, J=7.4 Hz, 1H).

MS m/z; 213([M+H]$^+$)

(2) (1S,2S,3S,5R,6S)-2-Amino-3-fluorobicyclo[3.1.0]hexane-2,6-dicarboxylic acid (IV)

The obtained solution containing (1S,2S,3S,5R,6S)-ethyl 2-amino-2-cyano-3-fluorobicyclo[3.1.0]hexane-6-carboxylate (Reference Example 2-1) was concentrated under reduced pressure. Water (30 ml), acetic acid (30 ml) and 35% hydrochloric acid (60 ml) were added and the mixture was stirred at an ambient temperature of 105° C. for 22 hours. To the reaction solution, activated carbon (3.0 g) was added at room temperature, and the mixture was stirred for 1 hour. The insoluble was filtered off and then the filtrate was concentrated under reduced pressure. The resulting residue was purified by anion-exchange column chromatography (Dowex 1X8, 0.5 mol/L acetic acid-water) to give (1S,2S,3S,5R,6S)-2-amino-3-fluorobicyclo[3.1.0]hexane-2,6-dicarboxylic acid (IV, 25.48 g) as a colorless solid.

$^1$H NMR (500 MHz, D2O) δ=5.06(dd, J=5.8, 53.2 Hz, 1H), 2.65(ddt, J=15.5, 42.0, 4.5 Hz, 1H), 2.36(dd, J=16.0, 29.0 Hz, 1H), 2.21-2.17(m, 1H), 2.10(br s, 1H), 1.91-1.89 (m, 1H).

MS m/z; 202([M−H]$^−$)

Example A-1

Synthesis of (1S,2S,3S,5R,6S)-6-(((adamantane-1-carbonyl)oxy)methoxy)carbonyl-2-amino-3-fluorobicyclo[3.1.0]hexane-2-carboxylic acid (A-1)

(1) (1S,2S,3S,5R,6S)-2-(((Allyloxy)carbonyl) amino)-3-fluorobicyclo[3.1.0]hexane-2,6-dicarboxylic acid (A-1-1)

To a suspension of (1S,2S,3S,5R,6S)-2-amino-3-fluorobicyclo[3.1.0]hexane-2,6-dicarboxylic acid (IV) (4.00 g) in dioxane (24 mL) and a saturated aqueous sodium bicarbonate solution (48 mL), allyl chloroformate (0.42 mL) was added dropwise over 15 minutes, and the mixture was stirred at room temperature for 20 hours. After addition of 1 mol/L hydrochloric acid to the reaction solution to adjust it to pH 1, the mixture was extracted three times with ethyl acetate. The combined ethyl acetate layer was dried over anhydrous sodium sulfate, the drying agent was filtered off and then the filtrate was concentrated under reduced pressure to give (1S,2S,3S,5R,6S)-2-(((allyloxy)carbonyl)amino)-3-fluorobicyclo[3.1.0]hexane-2,6-dicarboxylic acid (A-1-1, 6.23 g) as a colorless amorphous.

¹H NMR (600 MHz, DMSO-d6) δ=8.27(s, 1H), 5.98-5.81 (m, 1H), 5.43-5.03(m, 3H), 4.59-4.36(m, 2H), 2.48-2.36(m, 1H), 2.22-1.93(m, 3H), 1.79(br s, 1H), 1.71(t, J=3.1 Hz, 1H).
MS m/z; 310([M+Na]$^+$)

(2) (1S,2S,3S,5R,6S)-3'-((Allyloxy)carbonyl)-3-fluoro-5'-oxospiro[bicyclo[3.1.0]hexan-2,4'-oxazolidine]-6-carboxylic acid (A-1-2)

A suspension of (1S,2S,3S,5R,6S)-2-(((allyloxy)carbonyl)amino)-3-fluorobicyclo[3.1.0]hexane-2,6-dicarboxylic acid obtained above (A-1-1, 6.23 g), paraformaldehyde (3.00 g) and p-toluenesulfonic acid monohydrate (45 mg) in toluene (150 mL) was heated at reflux under a Dean-Stark water separator for 34 hours. The suspension was allowed to cool and then diluted with ethyl acetate, and the organic layer was washed twice with brine. After the organic layer was dried over anhydrous sodium sulfate, the insoluble was filtered and the filtrate was concentrated under reduced pressure to give (1S,2S,3S,5R,6S)-3'-((allyloxy)carbonyl)-3-fluoro-5'-oxospiro[bicyclo[3.1.0]hexan-2,4'-oxazolidine]-6-carboxylic acid (A-1-2, 5.65 g) as a colorless solid.
¹H NMR (600 MHz, CHLOROFORM-d) δ=5.89-5.78(m, 1H), 5.49(d, J=4.5 Hz, 1H), 5.25-5.10(m, 3H), 4.65-4.48(m, 3H), 2.54-2.35(m, 2H), 2.27-2.11(m, 2H), 1.96(dd, J=3.3, 6.6 Hz, 1H).
MS m/z; 300([M+H]$^+$)

(3) (1S,2S,3S,5R,6S)-6-(((Adamantane-1-carbonyl)oxy)methyl) 3'-allyl 3-fluoro-5'-oxospiro[bicyclo[3.1.0]hexan-2,4'-oxazolidine]-3',6-dicarboxylate (A-1-3)

To a solution of (1S,2S,3S,5R,6S)-3'-((allyloxy)carbonyl)-3-fluoro-5'-oxospiro[bicyclo[3.1.0]hexan-2,4'-oxazolidine]-6-carboxylic acid obtained above (A-1-2, 1.05 g) in N,N-dimethylformamide (30 mL), cesium carbonate (1.37 g) was added, and the mixture was stirred at 60° C. for 10 minutes. After cooling of the reaction mixture to room temperature, chloromethyl adamantane-1-carboxylate (1.70 g) (see J. Med. Chem., 23, 474 (1980)) was added and the mixture was stirred at 60° C. for 1 hour. The mixture was allowed to cool and then a saturated aqueous ammonium chloride solution was added. The aqueous layer was extracted twice with ethyl acetate, and the combined organic layer was washed once with water and twice with brine and then dried over anhydrous sodium sulfate. The insoluble was filtered off and the filtrate was concentrated under reduced pressure. The resulting residue was purified by silica gel column chromatography (silica gel cartridge, hexane:ethyl acetate=90:10-50:50) to give (1S,2S,3S,5R,6S)-6-(((adamantane-1-carbonyl)oxy)methyl) 3'-allyl 3-fluoro-5'-oxospiro[bicyclo[3.1.0]hexan-2,4'-oxazolidine]-3',6-dicarboxylate (A-1-3, 894 mg) as a colorless amorphous.
¹H NMR (600 MHz, CHLOROFORM-d) δ=5.95(s, 1H), 5.79-5.71(m, 2H), 5.61(d, J=5.0 Hz, 1H), 5.37-5.30(m, 1H), 5.30-5.24(m, 2H), 4.77-4.60(m, 3H), 2.68-2.61(m, 1H), 2.61-2.48(m, 1H), 2.38-2.28(m, 1H), 2.27-2.21(m, 1H), 2.12-2.07(m, 1H), 2.02(br s, 3H), 1.93-1.84(m, 6H), 1.77-1.65(m, 6H).
MS m/z; 514([M+Na]$^+$)

(4) (1S,2S,3S,5R,6S)-6-(((Adamantane-1-carbonyl)oxy)methoxy)carbonyl-2-amino-3-fluorobicyclo[3.1.0]hexane-2-carboxylic acid (A-1)

To a solution of (1S,2S,3S,5R,6S)-6-(((adamantane-1-carbonyl)oxy)methyl) 3'-allyl 3-fluoro-5'-oxospiro[bicyclo[3.1.0]hexan-2,4'-oxazolidine]-3',6-dicarboxylate obtained above (A-1-3, 894 mg) in chloroform (30 mL), 1,3-dimethylbarbituric acid (828 mg) and tetrakis(triphenylphosphine)palladium (102 mg) were added under a nitrogen atmosphere, and the mixture was stirred at room temperature for 1 hour. After the reaction mixture was concentrated under reduced pressure, acetonitrile was added to the resulting residue and the mixture was stirred at room temperature for 20 minutes. The resulting solid was collected by filtration and washed with water to give the title compound (A-1, 588 mg) as a colorless solid.
¹H NMR (600 MHz, DMSO-d6) δ=5.59(m, 2H), 4.82-4.65(m, 1H), 2.58-2.45(m, 1H), 2.07-1.96(m, 1H), 1.95-1.92(m, 1H), 1.90(br s, 3H), 1.86(br s, 2H), 1.76-1.69(m, 6H), 1.65-1.51(m, 6H).
MS m/z; 396([M+H]$^+$)
$[\alpha]_D^{25}$ 37.6 (c 0.25, EtOH)

Example A-2

Synthesis of (1S,2S,3S,5R,6S)-6-(1-((adamantane-1-carbonyl)oxy)ethoxy)carbonyl-2-amino-3-fluorobicyclo[3.1.0]hexane-2-carboxylic acid (A-2)

(1) 1-Chloroethyl adamantane-1-carboxylate (A-2-1)

To a suspension of 1-adamantanecarboxylic acid (1.50 g) in water (22 mL), sodium carbonate (3.53 g) was added, and the mixture was stirred at 100° C. for 20 minutes. After cooling to 0° C., tetrabutylammonium hydrogen sulfate (1.00 g), chloroform (30 mL) and 1-chloroethyl sulfochloridate (1.94 g) were added to the reaction mixture, and the mixture was stirred at 0° C. for 1 hour and at room temperature for 12 hours. To the reaction solution, water was added, and the mixture was extracted twice with chloroform. The combined organic layer was washed with brine and then dried over anhydrous sodium sulfate. The insoluble was filtered off and the filtrate was concentrated under reduced pressure. The resulting residue was purified by silica gel column chromatography (silica gel cartridge, hexane:ethyl acetate=100:0-50:50) to give 1-chloroethyl adamantane-1-carboxylate (A-2-1, 1.10 g) as a colorless oil.
¹H NMR (600 MHz, CHLOROFORM-d) δ=6.54(q, J=5.8 Hz, 1H), 2.03(br s, 4H), 1.97-1.63(m, 14H).

(2) 1-Bromoethyl adamantane-1-carboxylate (A-2-2)

To a solution of 1-chloroethyl adamantane-1-carboxylate obtained above (A-2-1, 500 mg) in benzene (5 mL), tetrabutylammonium bromide (25.2 mg) and trimethylsilyl bromide (0.80 mL) were added, and the mixture was stirred at 80° C. for 18 hours. The reaction solution was concentrated under reduced pressure and then diluted with chloroform. The organic layer was washed with water and brine and then dried over anhydrous sodium sulfate. The drying agent was filtered off and then the filtrate was concentrated under reduced pressure to give 1-bromoethyl adamantane-1-carboxylate (A-2-2, 498 mg) as a pale yellow oil.
¹H NMR (600 MHz, CHLOROFORM-d) δ=6.72(q, J=5.8 Hz, 1H), 2.08-1.96(m, 6H), 1.96-1.84(m, 6H), 1.81-1.67(m, 6H).

(3) (1S,2S,3S,5R,6S)-1-(((Adamantane-1-carbonyl)oxy)ethyl) 3'-allyl 3-fluoro-5'-oxospiro[bicyclo[3.1.0]hexan-2,4'-oxazolidine]-3',6-dicarboxylate (A-2-3)

(1S,2S,3S,5R,6S)-3'-((Allyloxy)carbonyl)-3-fluoro-5'-oxospiro[bicyclo[3.1.0]hexan-2,4'-oxazolidine]-6-carboxylic acid (A-1-2, 800 mg) and 1-chloroethyl adamantane-1-carboxylate (A-2-1, 1.62 g) were treated in the same manner as in Example A-1 (3) to give (1S,2S,3S,5R,6S)-1-(((adamantane-1-carbonyl)oxy)ethyl) 3'-allyl 3-fluoro-5'-oxospiro[bicyclo[3.1.0]hexan-2,4'-oxazolidine]-3',6-dicarboxylate (A-2-3, 500 mg) as a colorless amorphous.

$^1$H NMR (600 MHz, CHLOROFORM-d) δ=6.87-6.76(m, 1H), 6.03-5.92(m, 1H), 5.64-5.57 (m, 1H), 5.39-5.22(m, 3H), 4.79-4.58(m, 3H), 2.62-2.47(m, 2H), 2.39-2.27(m, 1H), 2.26-2.18(m, 1H), 2.11-2.05(m, 1H), 2.04-1.97(m, 3H), 1.92-1.80(m, 6H), 1.77-1.64(m, 6H), 1.49-1.41(m, 3H).

MS m/z; 528([M+Na]$^+$)

(4) (1S,2S,3S,5R,6S)-6-(((Adamantane-1-carbonyl)oxy)ethoxy)carbonyl-2-amino-3-fluorobicyclo[3.1.0]hexane-2-carboxylic acid (A-2)

(1S,2S,3S,5R,6S)-1-(((Adamantane-1-carbonyl)oxy)ethyl) 3'-allyl 3-fluoro-5'-oxospiro[bicyclo[3.1.0]hexan-2,4'-oxazolidine]-3',6-dicarboxylate (A-2-3, 700 mg) was treated in the same manner as in Example A-1 (4) to give the title compound (A-2, 330 mg) as a colorless solid.

$^1$H NMR (600 MHz, DMSO-d6) δ=6.70-6.65(m, 1H), 4.89-4.75(m, 1H), 2.66-2.51(m, 1H), 2.14-2.04(m, 1H), 1.97 (m, 4H), 1.93(m, 2H), 1.78(br s, 6H), 1.72-1.61(m, 6H), 1.42-1.37(m, 3H).

MS m/z; 410([M+H]$^+$)

Example A-3

Synthesis of (1S,2S,3S,5R,6S)-2-amino-3-fluoro-6-((1-(((((1R,2S,5R)-2-isopropyl-5-methylcyclohexyl)oxy)carbonyl)oxy)ethoxy)carbonyl)bicyclo[3.1.0]hexane-2-carboxylic acid (A-3)

(1) (1S,2S,3S,5R,6S)-3'-Allyl 6-((((((1R,2S,5R)-2-isopropyl-5-methylcyclohexyl)oxy)carbonyl)oxy)ethyl) 3-fluoro-5'-oxospiro[bicyclo[3.1.0]hexan-2,4'-oxazolidine]-3',6-dicarboxylate (A-3-1)

(1S,2S,3S,5R,6S)-3'-((Allyloxy)carbonyl)-3-fluoro-5'-oxospiro[bicyclo[3.1.0]hexan-2,4'-oxazolidine]-6-carboxylic acid (A-1-2, 350 mg) and 1-chloroethyl((1R,2S,5R)-2-isopropyl-5-methylcyclohexyl)carbonate (768 mg) were treated in the same manner as in Example A-1 (3) to give (1S,2S,3S,5R,6S)-3'-allyl 6-((((((1R,2S,5R)-2-isopropyl-5-methylcyclohexyl)oxy)carbonyl)oxy)ethyl) 3-fluoro-5'-oxospiro[bicyclo[3.1.0]hexan-2,4'-oxazolidine]-3',6-dicarboxylate (A-3-1, 260 mg) as a colorless oil.

$^1$H NMR (600 MHz, CHLOROFORM-d) δ=6.79-6.69(m, 1H), 6.01-5.91(m, 1H), 5.63-5.57 (m, 1H), 5.38-5.30(m, 1H), 5.30-5.22(m, 2H), 4.78-4.59(m, 3H), 4.58-4.49(m, 1H), 2.64-2.47(m, 2H), 2.37-2.20(m, 2H), 2.13-2.05(m, 2H), 1.97-1.88(m, 1H), 1.73-1.64(m, 2H), 1.54-1.36(m, 5H), 1.05 (dd, J=2.1, 11.1 Hz, 2H), 0.96-0.82(m, 7H), 0.82-0.73(m, 3H).

MS m/z; 548([M+Na]$^+$)

(2) (1S,2S,3S,5R,6S)-2-Amino-3-fluoro-6-((1-(((((1R,2S,5R)-2-isopropyl-5-methylcyclohexyl)oxy)carbonyl)oxy)ethoxy)carbonyl)bicyclo[3.1.0]hexane-2-carboxylic acid (A-3)

(1S,2S,3S,5R,6S)-3'-Allyl 6-((((((1R,2S,5R)-2-isopropyl-5-methylcyclohexyl)oxy)carbonyl)oxy)ethyl) 3-fluoro-5'-oxospiro[bicyclo[3.1.0]hexan-2,4'-oxazolidine]-3',6-dicarboxylate (A-3-1, 260 mg) was treated in the same manner as in Example A-1 (4) to give the title compound (A-3, 133 mg) as a colorless solid.

$^1$H NMR (600 MHz, DMSO-d6) δ=6.65-6.51(m, 1H), 4.91-4.74(m, 1H), 4.53-4.37(m, 1H), 2.69-2.53(m, 1H), 2.15-1.99(m, 2H), 1.98-1.87(m, 3H), 1.86-1.75(m, 1H), 1.68-1.57(m, 2H), 1.52-1.39(m, 4H), 1.39-1.29(m, 1H), 1.11-0.95(m, 2H), 0.93-0.80(m, 7H), 0.78-0.68(m, 3H).

MS m/z; 430([M+H]$^+$)

Example A-4

Synthesis of (1S,2S,3S,5R,6S)-2-amino-3-fluoro-6-(((((((1R,2S,5R)-2-isopropyl-5-methylcyclohexyl)oxy)carbonyl)oxy)methoxy)carbonyl)bicyclo[3.1.0]hexane-2-carboxylic acid (A-4)

(1S,2S,3S,5R,6S)-3'-((Allyloxy)carbonyl)-3-fluoro-5'-oxospiro[bicyclo[3.1.0]hexan-2,4'-oxazolidine]-6-carboxylic acid (A-1-2, 350 mg) and 1-chloromethyl((1R,2S,5R)-2-isopropyl-5-methylcyclohexyl)carbonate (727 mg) were treated in the same manner as in Example A-1 (3) and (4) to give the title compound (A-4, 140 mg) as a colorless solid.

$^1$H NMR (600 MHz, DMSO-d6) δ=5.74-5.64(m, 2H), 4.91-4.74(m, 1H), 4.53-4.42(m, 1H), 2.67-2.53(m, 1H), 2.15-2.02(m, 2H), 2.00-1.93(m, 3H), 1.86-1.77(m, 1H), 1.68-1.59(m, 2H), 1.53-1.42(m, 1H), 1.41-1.33(m, 1H), 1.04 (s, 2H), 0.94-0.80(m, 7H), 0.75(d, J=7.0 Hz, 3H).

MS m/z; 416([M+H]$^+$)

Example A-5

Synthesis of (1S,2S,3S,5R,6S)-2-amino-6-(1-((3,5-dimethyladamantane-1-carbonyl)oxy)ethoxy)carbonyl-3-fluorobicyclo[3.1.0]hexane-2-carboxylic acid (A-5)

(1) 1-Chloroethyl 3,5-dimethyladamantane-1-carboxylate (A-5-1)

3,5-Dimethyladamantane-1-carboxylic acid (2.00 g) and 1-chloroethyl sulfochloridate (2.58 g) were treated in the same manner as in Example A-2 (1) to give 1-chloroethyl 3,5-dimethyladamantane-1-carboxylate (A-5-1, 1.48 g) as a colorless oil.

$^1$H NMR (600 MHz, CHLOROFORM-d) δ=6.59-6.48(m, 1H), 2.17-2.08(m, 4H), 1.79(d, J=5.8 Hz, 3H), 1.76-1.69(m, 1H), 1.60-1.43(m, 5H), 1.40-1.29(m, 4H), 1.21-1.11(m, 2H), 0.90-0.82(m, 6H).

(2) (1S,2S,3S,5R,6S)-2-Amino-6-(((3,5-dimethyladamantane-1-carbonyl)oxy)ethoxy)carbonyl-3-fluorobicyclo[3.1.0]hexane-2-carboxylic acid (A-5)

(1S,2S,3S,5R,6S)-3'-((Allyloxy)carbonyl)-3-fluoro-5'-oxospiro[bicyclo[3.1.0]hexan-2,4'-oxazolidine]-6-carboxylic acid (A-1-2, 500 mg) and 1-chloroethyl 3,5-dimethyladamantane-1-carboxylate (A-5-1, 1.13 g) were treated in the same manner as in Example A-1 (3) and (4) to give the title compound (A-5, 70 mg) as a colorless solid.

$^1$H NMR (600 MHz, DMSO-d6) δ=6.69-6.58(m, 1H), 4.91-4.70(m, 1H), 2.65-2.50(m, 1H), 2.16-1.94(m, 2H), 1.94-1.75(m, 1H), 1.57(br s, 2H), 1.47-1.19(m, 7H), 1.16-1.03(m, 2H), 0.84-0.69(m, 6H).

MS m/z; 438([M+H]$^+$)

Example A-6

Synthesis of (1S,2S,3S,5R,6S)-2-amino-3-fluoro-6-(((octanoyloxy)methoxy)carbonyl)bicyclo[3.1.0]hexane-2-carboxylic acid (A-6)

(1S,2S,3S,5R,6S)-3'-((Allyloxy)carbonyl)-3-fluoro-5'-oxospiro[bicyclo[3.1.0]hexan-2,4'-oxazolidine]-6-carboxylic acid (A-1-2, 300 mg) and chloromethyl octanoate (483 mg) were treated in the same manner as in Example A-1 (3) and (4) to give the title compound (A-6, 95 mg) as a colorless solid.

$^1$H NMR (600 MHz, DMSO-d6) δ=5.72-5.63(m, 2H), 4.90-4.75(m, 1H), 2.67-2.51(m, 1H), 2.35(t, J=7.4 Hz, 2H), 2.14-2.00(m, 2H), 1.98-1.91(m, 2H), 1.56-1.47(m, 2H), 1.32-1.18(m, 8H), 0.89-0.82(m, 3H).

MS m/z; 360([M+H]$^+$)

Example A-7

Synthesis of (1S,2S,3S,5R,6S)-2-amino-3-fluoro-6-(((pivaloyloxy)methoxy)carbonyl)bicyclo[3.1.0]hexane-2-carboxylic acid (A-7)

(1S,2S,3S,5R,6S)-3'-((Allyloxy)carbonyl)-3-fluoro-5'-oxospiro[bicyclo[3.1.0]hexan-2,4'-oxazolidine]-6-carboxylic acid (A-1-2, 400 mg) and chloromethyl pivalate (193 mg) were treated in the same manner as in Example A-1 (3) and (4) to give the title compound (A-7, 60 mg) as a colorless solid.

$^1$H NMR (600 MHz, DMSO-d6) δ=5.72-5.66(m, 2H), 4.89-4.74(m, 1H), 2.67-2.53(m, 1H), 2.14-2.04(m, 1H), 2.04-1.99(m, 1H), 1.97-1.92(m, 2H), 1.15(s, 9H).

MS m/z; 318([M+H]$^+$)

Example A-8

Synthesis of (1S,2S,3S,5R,6S)-2-amino-3-fluoro-6-((1-(isobutyloxy)ethoxy)carbonyl)bicyclo[3.1.0]hexane-2-carboxylic acid hydrochloride (A-8)

(1) (1S,2S,3S,5R,6S)-3'-Allyl 6-(1-(isobutyryloxy)ethyl) 3-fluoro-5'-oxospiro[bicyclo[3.1.0]hexan-2,4'-oxazolidine]-3',6-dicarboxylate (A-8-1)

(1S,2S,3S,5R,6S)-3'-((Allyloxy)carbonyl)-3-fluoro-5'-oxospiro[bicyclo[3.1.0]hexan-2,4'-oxazolidine]-6-carboxylic acid (A-1-2, 1.43 g) and 1-chloroethyl isobutyrate (1.80 g) were treated in the same manner as in Example A-1 (3) to give (1S,2S,3S,5R,6S)-3'-allyl 6-(1-(isobutyryloxy)ethyl) 3-fluoro-5'-oxospiro[bicyclo[3.1.0]hexan-2,4'-oxazolidine]-3',6-dicarboxylate (A-8-1, 307 mg) as a pale yellow oil.

$^1$H NMR (600 MHz, CHLOROFORM-d) δ=6.84(dd, J=5.4, 11.1 Hz, 1H), 6.03-5.87(m, 1H), 5.47-5.43(m, 1H), 5.43-5.29(m, 1H), 5.29-5.22(m, 2H), 4.79-4.58(m, 3H), 2.66-2.42(m, 3H), 2.39-2.27(m, 1H), 2.26-2.18(m, 1H), 2.05 (s, 1H), 1.48(d, J=5.4 Hz, 3H), 1.24-1.12(m, 13H).

MS m/z; 436([M+Na]$^+$)

(2) (1S,2S,3S,5R,6S)-2-Amino-3-fluoro-6-((1-(isobutyloxy)ethoxy)carbonyl)bicyclo[3.1.0]hexane-2-carboxylic acid hydrochloride (A-8)

(1S,2S,3S,5R,6S)-3'-Allyl 6-(1-(isobutyryloxy)ethyl) 3-fluoro-5'-oxospiro[bicyclo[3.1.0]hexan-2,4'-oxazolidine]-3',6-dicarboxylate (A-8-1, 403 mg) was treated in the same manner as in Example A-1 (4) to give a pale yellow oil (278 mg) containing (1S,2S,3S,5R,6S)-2-amino-3-fluoro-6-((1-(isobutyloxy)ethoxy)carbonyl)bicyclo[3.1.0]hexane-2-carboxylic acid. To the obtained oil, ethyl acetate (3 mL) was added, the mixture was stirred and then a 4 mol/L hydrogen chloride-ethyl acetate solution (3 mL) was added while cooling on ice. The mixture was stirred at room temperature for 30 minutes, then concentrated under reduced pressure and dried to give the title compound (A-8, 200 mg) as a pale yellow solid.

$^1$H NMR (600 MHz, DMSO-d6) δ=8.82-8.64(m, 1H), 6.80-6.63(m, 1H), 5.19-4.99(m, 1H), 3.49-3.30(m, 2H), 2.68-2.43(m, 1H), 2.37-2.18(m, 2H), 2.18-2.01(m, 2H), 1.49-1.38(m, 3H), 1.16-1.01(m, 6H).

MS m/z; 318([M+H]$^+$)

Example A-9

Synthesis of (1S,2S,3S,5R,6S)-2-amino-6-(((benzoyloxy)methoxy)carbonyl)-3-fluorobicyclo[3.1.0]hexane-2-carboxylic acid (A-9)

(1S,2S,3S,5R,6S)-3'-((Allyloxy)carbonyl)-3-fluoro-5'-oxospiro[bicyclo[3.1.0]hexan-2,4'-oxazolidine]-6-carboxylic acid (A-1-2, 500 mg) and chloromethyl benzoate (712 mg) were treated in the same manner as in Example A-1 (3) and (4) to give the title compound (A-9, 198 mg) as a colorless solid.

$^1$H NMR (600 MHz, DMSO-d6) δ=8.03-7.94(m, 2H), 7.77-7.68(m, 1H), 7.62-7.51(m, 2H), 6.00-5.89(m, 2H), 4.97-4.77(m, 1H), 2.67-2.53(m, 1H), 2.17-2.06(m, 2H), 2.05-1.95(m, 2H).

MS m/z; 338([M+H]$^+$)

Example A-10

Synthesis of (1S,2S,3S,5R,6S)-2-amino-6-((1-(((cyclohexyloxy)carbonyl)oxy)ethoxy)carbonyl)-3-fluorobicyclo[3.1.0]hexane-2-carboxylic acid (A-10)

(1S,2S,3S,5R,6S)-3'-((Allyloxy)carbonyl)-3-fluoro-5'-oxospiro[bicyclo[3.1.0]hexan-2,4'-oxazolidine]-6-carboxylic acid (A-1-2, 1.35 g) and 1-chloroethyl cyclohexyl carbonate (2.06 mL) were treated in the same manner as in Example A-1 (3) and (4) to give the title compound (A-10, 113 mg) as a colorless solid.

$^1$H NMR (600 MHz, DMSO-d6) δ=6.68-6.52(m, 1H), 4.92-4.75(m, 1H), 4.62-4.49(m, 1H), 2.70-2.52(m, 1H), 2.19-1.89(m, 4H), 1.89-1.78(m, 2H), 1.70-1.58(m, 2H), 1.53-1.12(m, 7H).

MS m/z; 374([M+H]$^+$)

Example A-11

Synthesis of (1S,2S,3S,5R,6S)-2-amino-6-((1-(((cyclooctyloxy)carbonyl)oxy)ethoxy)carbonyl)-3-fluorobicyclo[3.1.0]hexane-2-carboxylic acid (A-11)

(1) 1-Chloroethyl cyclooctyl carbonate (A-11-1)

To a solution of cyclooctanol (1.79 g) in chloroform (40 mL), pyridine (1.13 mL) was added, and then the reaction solution was cooled to −60° C. To the reaction solution, 1-chloroethyl carbonochloridate (1.53 mL) was added at the same temperature over 10 minutes. The reaction solution was thereafter heated to room temperature and stirred at the same temperature for 3 hours. Chloroform was added to the reaction solution and the organic layer was washed three times with brine and then dried over magnesium sulfate. The insoluble was filtered and the filtrate was concentrated under reduced pressure to give 1-chloroethyl cyclooctyl carbonate (A-11-1, 3.70 g) as a colorless oil.

$^1$H NMR (600 MHz, CHLOROFORM-d) δ=6.48-6.37(m, 1H), 4.96-4.81(m, 1H), 1.97-1.66(m, 7H), 1.64-1.42(m, 7H).

(2) (1S,2S,3S,5R,6S)-2-Amino-6-((1-(((cyclooctyloxy)carbonyl)oxy)ethoxy)carbonyl)-3-fluorobicyclo[3.1.0]hexane-2-carboxylic acid (A-11)

(1S,2S,3S,5R,6S)-3'-((Allyloxy)carbonyl)-3-fluoro-5'-oxospiro[bicyclo[3.1.0]hexan-2,4'-oxazolidine]-6-carboxylic acid (A-1-2, 380 mg) and 1-chloroethyl cyclooctyl carbonate (A-11-1, 745 mg) were treated in the same manner as in Example A-1 (3) and (4) to give the title compound (A-11, 93 mg) as a colorless solid.

$^1$H NMR (600 MHz, DMSO-d6) δ=6.64-6.53(m, 1H), 4.92-4.76(m, 2H), 4.76-4.66(m, 1H), 2.68-2.53(m, 1H), 2.17-2.00(m, 2H), 2.00-1.89(m, 2H), 1.85-1.57(m, 6H), 1.57-1.36(m, 11H).

MS m/z; 402([M+H])$^+$

Example A-12

Synthesis of (1S,2S,3S,5R,6S)-2-amino-6-((1-((((4,4-dimethylcyclohexyl)oxy)carbonyl)oxy)ethoxy)carbonyl)-3-fluorobicyclo[3.1.0]hexane-2-carboxylic acid (A-12)

(1) 1-Chloroethyl(4,4-dimethylcyclohexyl)carbonate (A-12-1)

1-Chloroethyl carbonochloridate (1.19 mL) and 4,4-dimethyl-1-cyclohexanol (2.00 g) were treated in the same manner as in Example A-11 (1) to give 1-chloroethyl(4,4-dimethylcyclohexyl)carbonate (A-12-1, 4.37 g) as a colorless oil.

$^1$H NMR (200 MHz, CHLOROFORM-d) δ=6.49-6.36(m, 1H), 4.68(dddd, J=4.4, 4.4, 8.8, 8.8 Hz, 1H), 1.94-1.38(m, 9H), 1.35-1.16(m, 2H), 0.94(s, 3H), 0.92(s, 3H).

(2) (1S,2S,3S,5R,6S)-2-Amino-6-((1-((((4,4-dimethylcyclohexyl)oxy)carbonyl)oxy)ethoxy)carbonyl)-3-fluorobicyclo[3.1.0]hexane-2-carboxylic acid (A-12)

(1S,2S,3S,5R,6S)-3'-((Allyloxy)carbonyl)-3-fluoro-5'-oxospiro[bicyclo[3.1.0]hexan-2,4'-oxazolidine]-6-carboxylic acid (A-1-2, 300 mg) and 1-chloroethyl(4,4-dimethylcyclohexyl)carbonate (A-12-1, 588 mg) were treated in the same manner as in Example A-1 (3) and (4) to give the title compound (A-12, 70 mg) as a colorless solid.

$^1$H NMR (600 MHz, DMSO-d6) δ=6.64-6.55(m, 1H), 4.89-4.73(m, 1H), 4.60-4.50(m, 1H), 2.67-2.51(m, 1H), 2.15-1.99(m, 2H), 1.99-1.89(m, 2H), 1.78-1.70(m, 2H), 1.61-1.50(m, 2H), 1.47-1.41(m, 3H), 1.40-1.32(m, 2H), 1.28-1.18(m, 2H), 0.94-0.84 (m, 6H).

MS m/z; 402([M+H]$^+$)

Example A-13

Synthesis of (1S,2S,3S,5R,6S)-6-(((((adamantan-1-yloxy)carbonyl)oxy)methoxy)carbonyl)-2-amino-3-fluorobicyclo[3.1.0]hexane-2-carboxylic acid (A-13)

(1S,2S,3S,5R,6S)-3'-((Allyloxy)carbonyl)-3-fluoro-5'-oxospiro[bicyclo[3.1.0]hexan-2,4'-oxazolidine]-6-carboxylic acid (A-1-2, 500 mg) and adamantan-1-yl(chloromethyl)carbonate (1.02 g) were treated in the same manner as in Example A-1 (3) and (4) to give the title compound (A-13, 120 mg) as a pale yellow solid.

$^1$H NMR (600 MHz, DMSO-d6) δ=5.67-5.60(m, 2H), 4.94-4.77(m, 1H), 2.67-2.54(m, 1H), 2.21-1.94(m, 13H), 1.62(br s, 6H).

MS m/z; 412([M+H]$^+$)

Example A-14

Synthesis of (1S,2S,3S,5R,6S)-6-((1-(((adamantan-1-yloxy)carbonyl)oxy)ethoxy)carbonyl)-2-amino-3-fluorobicyclo[3.1.0]hexane-2-carboxylic acid (A-14)

(1S,2S,3S,5R,6S)-3'-((Allyloxy)carbonyl)-3-fluoro-5'-oxospiro[bicyclo[3.1.0]hexan-2,4'-oxazolidine]-6-carboxylic acid (A-1-2, 500 mg) and adamantan-1-yl(1-chloroethyl)carbonate (1.08 g) were treated in the same manner as in Example A-1 (3) and (4) to give the title compound (A-14, 164 mg) as a pale yellow solid.

$^1$H NMR (600 MHz, DMSO-d6) δ=6.60-6.48(m, 1H), 4.92-4.72(m, 1H), 2.69-2.42(m, 1H), 2.20-1.86(m, 13H), 1.61(br s, 6H), 1.41(dd, J=1.7, 5.4 Hz, 3H).

MS m/z; 426([M+H])$^+$

Example A-15

Synthesis of (1S,2S,3S,5R,6S)-2-amino-3-fluoro-6-((1-((isopropyloxycarbonyl)oxy)ethoxy)carbonyl)bicyclo[3.1.0]hexane-2-carboxylic acid trifluoroacetate (A-15)

(1) (1S,2S,3S,5R,6S)-3'-Allyl 6-(1-((isopropyloxycarbonyl)oxy)ethyl) 3-fluoro-5'-oxospiro[bicyclo[3.1.0]hexan-2,4'-oxazolidine]-3',6-dicarboxylate (A-15-1)

(1S,2S,3S,5R,6S)-3'-((Allyloxy)carbonyl)-3-fluoro-5'-oxospiro[bicyclo[3.1.0]hexan-2,4'-oxazolidine]-6-carboxylic acid (A-1-2, 400 mg) and 1-chloroethyl isopropyl carbonate (204 mg) were treated in the same manner as in Example A-1 (3) to give (1S,2S,3S,5R,6S)-3'-allyl 6-(1-((isopropyloxycarbonyl)oxy)ethyl) 3-fluoro-5'-oxospiro[bicyclo[3.1.0]hexan-2,4'-oxazolidine]-3',6-dicarboxylate (A-15-1, 95 mg) as a colorless oil.

$^1$H NMR (600 MHz, CHLOROFORM-d) δ=6.79-6.70(m, 1H), 6.02-5.90(m, 1H), 5.63-5.56(m, 1H), 5.38-5.30(m, 1H), 5.27(m, 2H), 4.94-4.84(m, 1H), 4.78-4.57(m, 3H), 2.63-2.47(m, 2H), 2.38-2.20(m, 2H), 2.13-2.05(m, 1H), 1.52(m, 3H), 1.33-1.29(m, 6H).

MS m/z; 452([M+Na])$^+$ (2) (1S,2S,3S,5R,6S)-2-Amino-3-fluoro-6-((1-((isopropyloxycarbonyl)oxy)ethoxy)carbonyl)bicyclo[3.1.0]hexane-2-carboxylic acid trifluoroacetate (A-15)

(1S,2S,3S,5R,6S)-3'-Allyl 6-(1-((isopropyloxycarbonyl)oxy)ethyl) 3-fluoro-5'-oxospiro[bicyclo[3.1.0]hexan-2,4'- oxazolidine]-3',6-dicarboxylate (A-15-1, 95 mg) was treated in the same manner as in Example A-1 (4) to give a solid containing (1S,2S,3S,5R,6S)-2-amino-3-fluoro-6-((1-((isopropyloxycarbonyl)oxy)ethoxy)carbonyl)bicyclo[3.1.0]hexane-2-carboxylic acid. To the obtained solid, dimethyl sulfoxide was added, and the solution was purified by reverse-phase column chromatography (mobile phase: 0.1% TFA MeCN/H$_2$O=10/90-90/10; v/v). The fraction was neutralized with a saturated aqueous sodium bicarbonate solution, extracted with chloroform and filtered through Phase Separator. The filtrate was concentrated under reduced pressure to give the title compound (A-15, 65 mg) as a colorless solid.

$^1$H NMR (600 MHz, DMSO-d6) δ=6.66-6.58(m, 1H), 5.14-5.01(m, 1H), 4.82-4.75(m, 1H), 2.65-2.51(m, 1H), 2.33-2.05(m, 4H), 1.48-1.41(m, 3H), 1.26-1.20(m, 6H).

MS m/z; 334([M+H])$^+$

Example A-16

Synthesis of (1S,2S,3S,5R,6S)-2-amino-3-fluoro-6-(((5-methyl-2-oxo-1,3-dioxol-4-yl)methoxy)carbonyl)bicyclo[3.1.0]hexane-2-carboxylic acid (A-16)

(1S,2S,3S,5R,6S)-3'-((Allyloxy)carbonyl)-3-fluoro-5'-oxospiro[bicyclo[3.1.0]hexan-2,4'-oxazolidine]-6-carboxylic acid (A-1-2, 660 mg) and 4-(bromomethyl)-5-methyl-1,3-dioxol-2-one (639 mg) were treated in the same manner as in Example A-1 (3) and (4) to give the title compound (A-16, 188 mg) as a pale yellow solid.

$^1$H NMR (600 MHz, DMSO-d6) δ=4.96(s, 2H), 4.93-4.78 (m, 1H), 2.68-2.52(m, J=14.9 Hz, 1H), 2.19-2.01(m, 5H), 2.01-1.89(m, 2H).

MS m/z; 316([M+H]$^+$)

Example A-17

Synthesis of (1S,2S,3S,5R,6S)-2-amino-3-fluorobicyclo[3.1.0]hexane-2,6-dicarboxylic acid 6-(3-phthalidyl) ester hydrochloride (A-17)

(1) (1S,2S,3S,5R,6S)-3'-Allyl 6-(3-oxo-1,3-dihydroisobenzofuran-1-yl) 3-fluoro-5'-oxospiro[bicyclo[3.1.0]hexan-2,4'-oxazolidine]-3',6-dicarboxylate (A-17-1)

(1S,2S,3S,5R,6S)-3'-((Allyloxy)carbonyl)-3-fluoro-5'-oxospiro[bicyclo[3.1.0]hexan-2,4'-oxazolidine]-6-carboxylic acid (A-1-2, 640 mg) and 3-bromophthalide (456 mg) were treated in the same manner as in Example A-1 (3) to give (1S,2S,3S,5R,6S)-3'-allyl 6-(3-oxo-1,3-dihydroisobenzofuran-1-yl) 3-fluoro-5'-oxospiro[bicyclo[3.1.0]hexan-2,4'-oxazolidine]-3',6-dicarboxylate (A-17-1, 380 mg) as a pale yellow amorphous.

$^1$H NMR (600 MHz, CHLOROFORM-d) δ=7.98-7.89(m, J=7.4 Hz, 1H), 7.83-7.55(m, 3H), 7.46-7.40(m, 1H), 5.92-5.82(m, 1H), 5.65-5.58(m, 1H), 5.30-5.25(m, 1H), 5.25-5.19 (m, 1H), 5.18-5.10(m, 1H), 4.77-4.54 (m, 3H), 2.74-2.65(m, 1H), 2.64-2.50(m, 1H), 2.39-2.28(m, 2H), 2.21-2.16(m, 1H).

MS m/z; 454([M+Na]$^+$)

(2) (1S,2S,3S,5R,6S)-2-Amino-3-fluorobicyclo[3.1.0]hexane-2,6-dicarboxylic acid 6-(3-phthalidyl) ester hydrochloride (A-17)

(1S,2S,3S,5R,6S)-3'-Allyl 6-(3-oxo-1,3-dihydroisobenzofuran-1-yl) 3-fluoro-5'-oxospiro[bicyclo[3.1.0]hexan-2,4'-oxazolidine]-3',6-dicarboxylate (A-17-1, 380 mg) was treated in the same manner as in Example A-8 (2) to give the title compound (A-17, 120 mg) as a colorless solid.

$^1$H NMR (600 MHz, DMSO-d6) δ=7.98-7.73(m, 4H), 7.53-7.47(m, 1H), 5.18-5.03(m, 1H), 2.67-2.51(m, 1H), 2.40-2.24(m, 3H), 2.21-2.15(m, 1H).

MS m/z; 336([M+H]$^+$)

Example A-18

Synthesis of (1S,2S,3S,5R,6S)-2-amino-3-fluoro-6-(((S)-1-(((((1R,2S,5R)-2-isopropyl-5-methylcyclohexyl)oxy)carbonyl)oxy)ethoxy)carbonyl)bicyclo[3.1.0]hexane-2-carboxylic acid (A-18)

(1) (1S,2S,3S,5R,6S)-6-Carboxyl-2,2'-diethyl-3-fluoro-5'-oxospiro[bicyclo[3.1.0]hexan-2,4'-oxazaborolidin]-3'-ium-8-uide (A-18-1)

To (1S,2S,3S,5R,6S)-2-amino-3-fluorobicyclo[3.1.0]hexane-2,6-dicarboxylic acid (IV) (70.0 g), a 1 mol/L triethylborane-tetrahydrofuran solution (362 mL) was added dropwise over 20 minutes while cooling on ice, and the mixture was stirred on ice for 4 hours. The reaction solution was added dropwise to heptane (4200 mL) over 1 hour and the mixture was stirred at room temperature for 30 minutes. The resulting solid was collected by filtration and washed with heptane (140 mL) to give (1S,2S,3S,5R,6S)-6-carboxyl-2,2'-diethyl-3-fluoro-5'-oxospiro[bicyclo[3.1.0]hexan-2,4'-oxazaborolidin]-3'-ium-8-uide (A-18-1, 89.68 g) as a colorless solid.

$^1$H NMR (600 MHz, DMSO-d6) δ=6.89-6.80 (m, 1H), 6.15-6.04 (m, 1H), 4.95-4.81 (m, 1H), 3.33 (s, 1H), 2.53-2.37 (m, 1H), 2.25-2.15 (m, 1H), 2.06-2.02 (m, 1H), 2.00-1.93 (m, 1H), 1.82-1.76 (m, 1H), 0.77-0.69 (m, 6H), 0.35-0.22 (m, 4H).

MS m/z; 272([M+H]$^+$)

(2) (S)-1-Chloroethyl((1R,2S,5R)-2-isopropyl-5-methylcyclohexyl)carbonate (A-18-2-1) and (R)-1-chloroethyl((1R,2S,5R)-2-isopropyl-5-methylcyclohexyl)carbonate (A-18-2-2)

A solution of 1-chloroethyl((1R,2S,5R)-2-isopropyl-5-methylcyclohexyl)carbonate (146 g) in heptane (146 mL) was stirred at −25° C. for 1.5 hours. The resulting solid was collected by filtration to give a colorless solid containing (S)-1-chloroethyl((1R,2S,5R)-2-isopropyl-5-methylcyclohexyl)carbonate. A solution of the obtained colorless solid (46.8 g) containing (S)-1-chloroethyl((1R,2S,5R)-2-isopropyl-5-methylcyclohexyl)carbonate in heptane (94 mL) was stirred at −40° C. for 1.5 hours. The resulting solid was collected by filtration to give (S)-1-chloroethyl((1R,2S,5R)-2-isopropyl-5-methylcyclohexyl)carbonate (A-18-2-1, 37.87 g) as a colorless solid. Further, 1-chloroethyl((1R,2S,5R)-2-isopropyl-5-methylcyclohexyl)carbonate (300 mg) was separated by chiral column chromatography (CHIRALCEL OD, hexane) to give (S)-1-chloroethyl((1R,2S,5R)-2-isopropyl-5-methylcyclohexyl)carbonate (A-18-2-1, 117 mg) as a colorless solid and (R)-1-chloroethyl((1R,2S,5R)-2-isopropyl-5-methylcyclohexyl)carbonate (A-18-2-2, 129 mg) as a colorless oil. The absolute configuration of the obtained compound (A-18-2-1) was determined by X-ray structure analysis.

Spectrum of Compound (A-18-2-1): $^1$H NMR (600 MHz, CHLOROFORM-d) δ=6.43(q, J=5.8 Hz, 1H), 4.58(dt, J=4.5, 10.9 Hz, 1H), 2.15-2.10(m, 1H), 2.00-1.90(m, 1H), 1.83(d, J=2.8 Hz, 3H), 1.72-1.66(m, 2H), 1.52-1.41(m, 2H), 1.12-1.02(m, 2H), 0.94-0.86(m, 7H), 0.79(d, J=7.0 Hz, 3H).

Spectrum of Compound (A-18-2-2): $^1$H NMR (600 MHz, CHLOROFORM-d) δ=6.43(q, J=5.8 Hz, 1H), 4.60(dt, J=4.1, 10.9 Hz, 1H), 2.10-2.05(m, 1H), 1.98-1.91(m, 1H), 1.83(d, J=5.8 Hz, 3H), 1.72-1.67(m, 2H), 1.53-1.40(m, 2H), 1.11-1.03(m, 2H), 0.94-0.86(m, 7H), 0.81(d, J=7.0 Hz, 3H).

(3) (1S,2S,3S,5R,6S)-2,2'-Diethyl-3-fluoro-6-(((S)-1-(((((1R,2S,5R)-2-isopropyl-5-methylcyclohexyl)oxy)carbonyl)oxy)ethoxy)carbonyl)-5'-oxospiro[bicyclo[3.1.0]hexan-2,4'-oxazaborolidin]-3'-ium-8-uide (A-18-3)

To a solution of (1S,2S,3S,5R,6S)-6-carboxyl-2,2'-diethyl-3-fluoro-5'-oxospiro[bicyclo[3.1.0]hexan-2,4'-oxazaborolidin]-3'-ium-8-uide obtained in Step (1) (A-18-1, 25.0 g) in dimethyl sulfoxide (475 mL), potassium carbonate (13.38 g) was added, and the mixture was stirred at room temperature for 30 minutes. To the reaction mixture, (S)-1-chloroethyl((1R,2S,5R)-2-isopropyl-5-methylcyclohexyl) carbonate obtained in Step (2) (A-18-2-1, 29.08 g) and 18-crown-6 (25.60 g) were added while well washing with dimethyl sulfoxide (25 mL), and the mixture was stirred at room temperature for 4.5 hours. The reaction mixture was diluted with ethyl acetate (750 mL) while cooling on ice and the ice-cooled reaction mixture was added to a solution of a mixture of a saturated aqueous ammonium chloride solution (250 mL) and water (250 mL) over 20 minutes. Ethyl acetate (250 mL) was used to wash the reaction vessel and added to the mixture. The combined reaction mixture was separated and then heptane (500 mL) was added to the organic layer obtained. The resulting organic layer was washed once with brine and then dried over anhydrous sodium sulfate. The insoluble was filtered off and then the solution containing (1S,2S,3S,5R,6S)-2,2'-diethyl-3-fluoro-6-(((S)-1-(((((1R,2S,5R)-2-isopropyl-5-methylcyclohexyl)oxy)carbonyl)oxy)ethoxy)carbonyl)-5'-oxospiro[bicyclo[3.1.0]hexan-2,4'-oxazaborolidin]-3'-ium-8-uide (A-18-3) was used for the next reaction without concentration and purification of the filtrate.

$^1$H NMR (600 MHz, DMSO-d6) δ=6.94-6.85(m, 1H), 6.64-6.54(m, 1H), 6.19-6.09(m, 1H), 4.99-4.84(m, 1H), 4.51-4.43(m, 1H), 2.49-2.39(m, 1H), 2.24-2.15(m, 1H), 2.14-2.09(m, 1H), 2.08-2.02(m, 1H), 1.98-1.92(m, 1H), 1.83-1.72(m, 2H), 1.67-1.58(m, 2H), 1.50-1.42(m, 4H), 1.39-1.30(m, 1H), 1.08-0.98(m, 2H), 0.91-0.84(m, 7H), 0.78-0.67(m, 9H), 0.37-0.21(m, 4H).

MS m/z; 520([M+Na]$^+$)

(4) (1S,2S,3S,5R,6S)-2-Amino-3-fluoro-6-(((S)-1-(((((1R,2S,5R)-2-isopropyl-5-methylcyclohexyl)oxy)carbonyl)oxy)ethoxy)carbonyl)bicyclo[3.1.0]hexane-2-carboxylic acid benzenesulfonate (A-18-4)

To the solution containing (1S,2S,3S,5R,6S)-2,2'-diethyl-3-fluoro-6-(((S)-1-(((((1R,2S,5R)-2-isopropyl-5-methylcyclohexyl)oxy)carbonyl)oxy)ethoxy)carbonyl)-5'-oxospiro[bicyclo[3.1.0]hexan-2,4'-oxazaborolidin]-3'-ium-8-uide (A-18-3) obtained in Step (3), benzenesulfonic acid monohydrate (19.50 g) was added, and the mixture was stirred at room temperature for 18 hours. The resulting solid was collected by filtration and washed with a solvent mixture of ethyl acetate and heptane (50 mL and 25 mL, respectively) to give (1S,2S,3S,5R,6S)-2-amino-3-fluoro-6-(((S)-1-(((((1R,2S,5R)-2-isopropyl-5-methylcyclohexyl)oxy)carbonyl)oxy)ethoxy)carbonyl)bicyclo[3.1.0]hexane-2-carboxylic acid benzenesulfonate (A-18-4, 33.0 g) as a colorless solid. The absolute configuration of the obtained compound (A-18-4) was determined by X-ray structure analysis.

$^1$H NMR (600 MHz, DMSO-d6) δ=7.62-7.56(m, 2H), 7.34-7.27(m, 3H), 6.61-6.57(m, 1H), 5.17-5.05(m, 1H), 4.50-4.44(m, 1H), 2.65-2.51(m, 1H), 2.29-2.18(m, 2H), 2.15-2.10(m, 1H), 2.10-2.06(m, 1H), 1.97-1.92(m, 1H), 1.83-1.74(m, 1H), 1.67-1.59(m, 2H), 1.50-1.43(m, 4H), 1.38-1.31(m, 1H), 1.09-0.98(m, 2H), 0.91-0.81(m, 7H), 0.75 (d, J=7.0 Hz, 3H).

MS m/z; 428([M−H]$^−$)

$[α]_D^{24}$ −5.8 (c 1.02, EtOH)

Melting point: 178° C. (decomposition temp.)

(5) (1S,2S,3S,5R,6S)-2-Amino-3-fluoro-6-(((S)-1-(((((1R,2S,5R)-2-isopropyl-5-methylcyclohexyl)oxy)carbonyl)oxy)ethoxy)carbonyl)bicyclo[3.1.0]hexane-2-carboxylic acid (A-18)

To a suspension of (1S,2S,3S,5R,6S)-2-amino-3-fluoro-6-(((S)-1-(((((1R,2S,5R)-2-isopropyl-5-methylcyclohexyl)oxy)carbonyl)oxy)ethoxy)carbonyl)bicyclo[3.1.0]hexane-2-carboxylic acid benzenesulfonate obtained in Step (4) (A-18-4, 33.0 g) in acetone (125 mL), water (25 mL) was added for dissolution. The resulting solution was added dropwise to water (1225 mL) over 30 minutes and the mixture was stirred at room temperature for 2 hours. The resulting solid was collected by filtration and washed with water (50 ml) to give the title compound (A-18, 24.08 g) as a colorless solid.

$^1$H NMR (600 MHz, DMSO-d6) δ=6.61-6.55(m, 1H), 4.90-4.77(m, 1H), 4.50-4.43(m, 1H), 2.67-2.54(m, 1H), 2.11-2.00(m, 2H), 1.97-1.89(m, 3H), 1.83-1.75(m, 1H), 1.66-1.59(m, 2H), 1.51-1.41(m, 4H), 1.38-1.31(m, 1H), 1.09-0.97(m, 2H), 0.91-0.80(m, 7H), 0.75(d, J=7.0 Hz, 3H).

MS m/z; 428([M−H]$^−$)

Melting point: 175° C. (decomposition temp.)

(6) (1S,2S,3S,5R,6S)-2-Amino-3-fluoro-6-(((S)-1-(((((1R,2S,5R)-2-isopropyl-5-methylcyclohexyl)oxy)carbonyl)oxy)ethoxy)carbonyl)bicyclo[3.1.0]hexane-2-carboxylic acid methanesulfonate (A-18-6)

(1S,2S,3S,5R,6S)-2,2'-Diethyl-3-fluoro-6-(((S)-1-(((((1R,2S,5R)-2-isopropyl-5-methylcyclohexyl)oxy)carbonyl)oxy)ethoxy)carbonyl)-5'-oxospiro[bicyclo[3.1.0]hexan-2,4'-oxazaborolidin]-3'-ium-8-uide (A-18-3) obtained in Step (3) and methanesulfonic acid were treated in the same manner as in Example A-18 (4) to give (1S,2S,3S,5R,6S)-2-amino-3-fluoro-6-(((S)-1-(((((1R,2S,5R)-2-isopropyl-5-methylcyclohexyl)oxy)carbonyl)oxy)ethoxy)carbonyl)bicyclo[3.1.0]hexane-2-carboxylic acid methanesulfonate (A-18-6) as a colorless solid.

Melting point: 160° C. (decomposition temp.)

(7) (1S,2S,3S,5R,6S)-2-Amino-3-fluoro-6-(((S)-1-(((((1R,2S,5R)-2-isopropyl-5-methylcyclohexyl)oxy)carbonyl)oxy)ethoxy)carbonyl)bicyclo[3.1.0]hexane-2-carboxylic acid ethanesulfonate (A-18-7)

(1S,2S,3S,5R,6S)-2,2'-Diethyl-3-fluoro-6-(S)-1-(((((1R,2S,5R)-2-isopropyl-5-methylcyclohexyl)oxy)carbonyl)oxy)ethoxy)carbonyl)-5'-oxospiro[bicyclo[3.1.0]hexan-2,4'-oxazaborolidin]-3'-ium-8-uide (A-18-3) obtained in Step (3) and ethanesulfonic acid were treated in the same manner as in Example A-18 (4) to give (1S,2S,3S,5R,6S)-2-amino-3-fluoro-6-(((S)-1-(((((1R,2S,5R)-2-isopropyl-5-methylcyclohexyl)oxy)carbonyl)oxy)ethoxy)carbonyl)bicyclo[3.1.0] hexane-2-carboxylic acid ethanesulfonate (A-18-7) as a colorless solid.

Melting point: 195° C. (decomposition temp.)

(8) (1S,2S,3S,5R,6S)-2-Amino-3-fluoro-6-(((S)-1-(((((1R,2 S,5R)-2-isopropyl-5-methylcyclohexyl) oxy)carbonyl)oxy)ethoxy)carbonyl)bicyclo[3.1.0] hexane-2-carboxylic acid p-toluenesulfonate (A-18-8)

(1S,2S,3S,5R,6S)-2,2'-Diethyl-3-fluoro-6-(((S)-1-(((((1R,2S,5R)-2-isopropyl-5-methylcyclohexyl)oxy)carbonyl)oxy)ethoxy)carbonyl)-5'-oxospiro[bicyclo[3.1.0]hexan-2,4'-oxazaborolidin]-3'-ium-8-uide (A-18-3) obtained in Step (3) and p-toluenesulfonic acid monohydrate were treated in the same manner as in Example A-18 (4) to give (1S,2 S,3S,5R,6S)-2-amino-3-fluoro-6-(((S)-1-(((((1R,2S,5R)-2-isopropyl-5-methylcyclohexyl)oxy)carbonyl)oxy) ethoxy)carbonyl)bicyclo[3.1.0]hexane-2-carboxylic acid p-toluenesulfonate (A-18-8) as a colorless solid.

Melting point: 175° C. (decomposition temp.)

(9) (1S,2S,3S,5R,6S)-2-Amino-3-fluoro-6-(((S)-1-(((((1R,2S,5R)-2-isopropyl-5-methylcyclohexyl)oxy) carbonyl)oxy)ethoxy)carbonyl)bicyclo[3.1.0]hexane-2-carboxylic acid (−)-10-camphorsulfonate (A-18-9)

(1S,2S,3S,5R,6S)-2,2'-Diethyl-3-fluoro-6-(((S)-1-(((((1R,2S,5R)-2-isopropyl-5-methylcyclohexyl)oxy)carbonyl)oxy)ethoxy)carbonyl)-5'-oxospiro[bicyclo[3.1.0]hexan-2,4'-oxazaborolidin]-3'-ium-8-uide (A-18-3) obtained in Step (3) and (−)-10-camphorsulfonic acid were treated in the same manner as in Example A-18 (4) to give (1S,2S,3S,5R,6S)-2-amino-3-fluoro-6-(((S)-1-(((((1R,2S,5R)-2-isopropyl-5-methylcyclohexyl)oxy)carbonyl)oxy)ethoxy)carbonyl)bicyclo[3.1.0]hexane-2-carboxlic acid (-)-10-camphorsulfonate (A-18-9) as a colorless solid.

Melting point: 174° C. (decomposition temp.)

Example A-19

Synthesis of (1S,2S,3S,5R,6S)-2-amino-3-fluoro-6-(((R)-1-(((((1R,2S,5R)-2-isopropyl-5-methylcyclohexyl)oxy)carbonyl)oxy)ethoxy)carbonyl)bicyclo[3.1.0]hexane-2-carboxylic acid (A-19)

(1S,2S,3S,5R,6S)-6-Carboxyl-2,2'-diethyl-3-fluoro-5'-oxospiro[bicyclo[3.1.0]hexan-2,4'-oxazaborolidin]-3'-ium-8-uide (A-18-1, 33 mg) and (R)-1-chloroethyl((1R,2S,5R)-2-isopropyl-5-methylcyclohexyl)carbonate (A-18-2-2, 51 mg) were treated in the same manner as in Example A-18 (3) to (5) to give the title compound (A-19, 7.0 mg) as a colorless solid.

$^1$H NMR (600 MHz, DMSO-d6) δ=6.60(m, 1H), 4.89-4.71(m, 1H), 4.44(dt, J=4.1, 10.9 Hz, 1H), 2.56-2.40(m, 1H), 2.11-2.01(m, 2H), 1.98-1.93(m, 1H), 1.91(br s, 2H), 1.85-1.77(m, 1H), 1.90-1.60(m, 2H), 1.49-1.42(m, 4H), 1.39-1.31(m, 1H), 1.08-0.98(m, 2H), 0.91-0.83(m, 7H), 0.74 (d, J=7.0 Hz, 3H).

MS m/z; 428([M−H]$^-$)

Example A-20

Synthesis of (1S,2S,3S,5R,6S)-6-(((S)-1-((adamantane-1-carbonyl)oxy)ethoxy)carbonyl)-2-amino-3-fluorobicyclo[3.1.0]hexane-2-carboxylic acid (A-20)

(1) (S)-1-Chloroethyl adamantane-1-carboxylate (A-20-1-1) and (R)-1-chloroethyl adamantane-1-carboxylate (A-20-1-2)

1-Chloroethyl adamantane-1-carboxylate (A-2-1, 600 mg) was separated by chiral column chromatography (CHIRALPAK AD-H, hexane/ethanol=95/5) to give (S)-1-chloroethyl adamantane-1-carboxylate (A-20-1-1, 230 mg) eluted first as a colorless solid and (R)-1-chloroethyl adamantane-1-carboxylate (A-20-1-2, 200 mg) eluted second as a colorless solid. The absolute configuration of the obtained compound (A-20-1-2) was determined by X-ray structure analysis.

Spectrum of Compound (A-20-1-1): $^1$H NMR (600 MHz, CHLOROFORM-d) δ=6.54(q, J=5.8 Hz, 1H), 2.03(br s, 4H), 1.97-1.63(m, 14H).
$[α]_D^{22}$ 112.7 (c 1.11, EtOH)

Spectrum of Compound (A-20-1-2): $^1$H NMR (600 MHz, CHLOROFORM-d) δ=6.54(q, J=5.8 Hz, 1H), 2.03(br s, 4H), 1.97-1.63(m, 14H).
$[α]_D^{23}$ −111.7 (c 1.09, EtOH)

(2) (1S,2S,3S,5R,6S)-6-(((S)-1-((Adamantane-1-carbonyl)oxy)ethoxy)carbonyl)-2-amino-3-fluorobicyclo[3.1.0]hexane-2-carboxylic acid (A-20)

(1S,2S,3S,5R,6S)-6-Carboxyl-2,2'-diethyl-3-fluoro-5'-oxospiro[bicyclo[3.1.0]hexan-2,4'-oxazaborolidin]-3'-ium-8-uide (A-18-1, 1.85 g) and (S)-1-chloroethyl adamantane-1-carboxylate (A-20-1-1, 1.10 g) were treated in the same manner as in Example A-18 (3) to (5) to give the title compound (A-20, 636 mg) as a colorless solid.

$^1$H NMR (600 MHz, DMSO-d6) δ=6.70-6.65(m, 1H), 4.88-4.75(m, 1H), 2.66-2.51(m, 1H), 2.14-2.05(m, 1H), 2.02-1.95(m, 4H), 1.95-1.90(m, 2H), 1.79-1.76(m, 6H), 1.71-1.62(m, 6H), 1.42-1.38(m, 3H).

MS m/z; 408([M−H]$^-$)
$[α]_D^{25}$ 42.9 (c 0.57, MeOH)

(3) (1S,2S,3S,5R,6S)-6-(((S)-1-((Adamantane-1-carbonyl)oxy)ethoxy)carbonyl)-2-amino-3-fluorobicyclo[3.1.0]hexane-2-carboxylic acid methanesulfonate (A-20-3)

In the same manner as in Example A-18 (6), (1S,2S,3S,5R,6S)-6-(((S)-1-((adamantane-1-carbonyl)oxy)ethoxy)carbonyl)-2-amino-3-fluorobicyclo[3.1.0]hexane-2-carboxylic acid methanesulfonate (A-20-3) was obtained as a colorless solid.

Melting point: 154° C. (decomposition temp.)

(4) (1S,2S,3S,5R,6S)-6-(((S)-1-((Adamantane-1-carbonyl)oxy)ethoxy)carbonyl)-2-amino-3-fluorobicyclo[3.1.0]hexane-2-carboxylic acid ethanesulfonate (A-20-4)

In the same manner as in Example A-18 (7), (1S,2S,3S,5R,6S)-6-(((S)-1-((adamantane-1-carbonyl)oxy)ethoxy)carbonyl)-2-amino-3-fluorobicyclo[3.1.0]hexane-2-carboxylic acid ethanesulfonate (A-20-4) was obtained as a colorless solid.

Melting point: 171° C. (decomposition temp.)

(5) (1S,2S,3S,5R,6S)-6-(((S)-1-((Adamantane-1-carbonyl)oxy)ethoxy)carbonyl)-2-amino-3-fluorobicyclo[3.1.0]hexane-2-carboxylic acid benzenesulfonate (A-20-5)

In the same manner as in Example A-18 (4), (1S,2S,3S,5R,6S)-6-(((S)-1-((adamantane-1-carbonyl)oxy)ethoxy)carbonyl)-2-amino-3-fluorobicyclo[3.1.0]hexane-2-carboxylic acid benzenesulfonate (A-20-5) was obtained as a colorless solid.

Melting point: 147° C. (decomposition temp.)

(6) (1S,2S,3S,5R,6S)-6-(((S)-1-((Adamantane-1-carbonyl)oxy)ethoxy)carbonyl)-2-amino-3-fluorobicyclo[3.1.0]hexane-2-carboxylic acid p-toluenesulfonate (A-20-6)

In the same manner as in Example A-18 (8), (1S,2S,3S,5R,6S)-6-(((S)-1-((adamantane-1-carbonyl)oxy)ethoxy)carbonyl)-2-amino-3-fluorobicyclo[3.1.0]hexane-2-carboxylic acid p-toluenesulfonate (A-20-6) was obtained as a colorless solid.

Melting point: 146° C. (decomposition temp.)

Example A-21

Synthesis of (1S,2S,3S,5R,6S)-6-(((R)-1-((adamantane-1-carbonyl)oxy)ethoxy)carbonyl)-2-amino-3-fluorobicyclo[3.1.0]hexane-2-carboxylic acid (A-21)

(1) (1S,2S,3S,5R,6S)-6-(((R)-1-((Adamantane-1-carbonyl)oxy)ethoxy)carbonyl)-2,2-diethyl-3-fluoro-5'-oxospiro[bicyclo[3.1.0]hexan-2,4'-oxazaborolidin]-3'-ium-8-uide (A-21-1)

(1S,2S,3S,5R,6S)-6-Carboxyl-2,2'-diethyl-3-fluoro-5'-oxospiro[bicyclo[3.1.0]hexan-2,4'-oxazaborolidin]-3'-ium-8-uide (A-18-1, 1.45 g) and (R)-1-chloroethyl adamantane-1-carboxylate (A-20-1-2, 2.08 g) were treated in the same manner as in Example A-18 (3) to give a solution containing (1S,2S,3S,5R,6S)-6-(((R)-1-((adamantane-1-carbonyl)oxy)ethoxy)carbonyl)-2,2'-diethyl-3-fluoro-5'-oxospiro[bicyclo[3.1.0]hexan-2,4'-oxazaborolidin]-3'-ium-8-uide (A-21-1), which was used for the next reaction.

(2) (1S,2S,3S,5R,6S)-6-(((R)-1-((Adamantane-1-carbonyl)oxy)ethoxy)carbonyl)-2-amino-3-fluorobicyclo[3.1.0]hexane-2-carboxylic acid hydrochloride (A-21-2)

To the obtained solution containing (1S,2S,3S,5R,6S)-6-(((R)-1-((adamantane-1-carbonyl)oxy)ethoxy)carbonyl)-2,2'-diethyl-3-fluoro-5'-oxospiro[bicyclo[3.1.0]hexan-2,4'-oxazaborolidin]-3'-ium-8-uide (A-21-1), a 4 mol/L hydrogen chloride-ethyl acetate solution (2.7 mL) was added at room temperature, and the mixture was stirred at room temperature for 7 hours. The resulting solid was collected by filtration and washed with a solvent mixture of ethyl acetate and heptane (10 mL and 10 mL, respectively) to give (1S,2S,3S,5R,6S)-6-(((R)-1-((adamantane-1-carbonyl)oxy)ethoxy)carbonyl)-2-amino-3-fluorobicyclo[3.1.0]hexane-2-carboxylic acid hydrochloride (A-21-2, 1.20 g) as a colorless solid.

$^1$H NMR (600 MHz, DMSO-d6) δ=6.72-6.68(m, 1H), 5.14-5.02(m, 1H), 2.61-2.51(m, 1H), 2.32-2.20(m, 2H), 2.13-2.04(m, 2H), 1.98(br s, 3H), 1.80-1.76(m, 6H), 1.71-1.62(m, 6H), 1.42(d, J=5.4 Hz, 3H).

MS m/z; 410([M+H]$^+$)

Melting point: 164° C. (decomposition temp.)

(3) (1S,2S,3S,5R,6S)-6-(((R)-1-((Adamantane-1-carbonyl)oxy)ethoxy)carbonyl)-2-amino-3-fluorobicyclo[3.1.0]hexane-2-carboxylic acid (A-21)

(1S,2S,3S,5R,6S)-6-(((R)-1-((Adamantane-1-carbonyl)oxy)ethoxy)carbonyl)-2-amino-3-fluorobicyclo[3.1.0]hexane-2-carboxylic acid hydrochloride (A-21-2, 2.20 g) was treated in the same manner as in Example A-18 (5) to give the title compound (A-21, 1.36 g) as a colorless solid.

$^1$H NMR (600 MHz, DMSO-d6) δ=6.68(q, J=5.6 Hz, 1H), 4.90-4.74(m, 1H), 2.66-2.52(m, 1H), 2.12-2.04(m, 1H), 2.01 (dd, J=2.9, 6.6 Hz, 1H), 1.97(br s, 3H), 1.96-1.90(m, 1H), 1.88(m, 1H), 1.78(d, J=2.5 Hz, 6H), 1.71-1.61(m, 6H), 1.40(d, J=5.4 Hz, 3H).

MS m/z; 410([M+H]$^+$)

$[α]_D^{24}$ 24.0 (c 0.53, MeOH)

Example B-1

Synthesis of (1S,2S,3S,5R,6S)-2-amino-2-((1-(((cyclohexyloxy)carbonyl)oxy)ethoxy)carbonyl)-3-fluorobicyclo[3.1.0]hexane-6-carboxylic acid (B-1)

(1) (1S,2S,3S,5R,6S)-6-((Allyloxy)carbonyl) 2-(((allyloxy)carbonyl)amino)-3-fluorobicyclo[3.1.0]hexane-2-carboxylic acid (B-1-1)

A solution of a mixture of (1S,2S,3S,5R,6S)-2-(((allyloxy)carbonyl)amino)-3-fluorobicyclo[3.1.0]hexane-2,6-dicarboxylic acid (A-1-1, 1.41 g), allyl alcohol (336 μL), N,N-diisopropylethylamine (837 μL) and N,N-dimethylaminopyridine (60 mg) in chloroform (30 mL) was cooled to 0° C. To this solution, 1-ethyl-3-(3-dimethylaminopropyl)carbodiimide hydrochloride (837 mg) was added, and then the mixture was heated to room temperature and stirred for 2 days. To the reaction solution, chloroform was added, and the organic layer was washed twice with 0.25 mol/L hydrochloric acid, once with water, and once with brine, sequentially. After the organic layer was dried over anhydrous magnesium sulfate, the insoluble was filtered and the filtrate was concentrated under reduced pressure to give (1S,2S,3S,5R,6S)-6-((allyloxy)carbonyl) 2-(((allyloxy)carbonyl)amino)-3-fluorobicyclo[3.1.0]hexane-2-carboxylic acid (B-1-1, 1.30 g) as a colorless amorphous.

(2) (1S,2S,3S,5R,6S)-2-Amino-2-((1-(((cyclohexyloxy)carbonyl)oxy)ethoxy)carbonyl)-3-fluorobicyclo[3.1.0]hexane-6-carboxylic acid (B-1)

(1S,2S,3S,5R,6S)-6-((Allyloxy)carbonyl) 2-(((allyloxy)carbonyl)amino)-3-fluorobicyclo[3.1.0]hexane-2-carboxylic acid (B-1-1, 701 mg) and 1-chloroethyl cyclohexyl carbonate (664 mg) were treated in the same manner as in Example A-8 (1), (2) to give the title compound (B-1, 115 mg) as a yellow solid.

$^1$H NMR (600 MHz, DMSO-d6) δ=6.79-6.64(m, 1H), 5.26-4.93(m, 1H), 4.64-4.51(m, 1H), 2.38-2.13(m, 2H), 2.13-1.94(m, 2H), 1.91-1.80(m, 2H), 1.73-1.58(m, 2H), 1.53 (dd, J=5.4, 8.3 Hz, 7H), 1.38-1.17(m, 3H).

MS m/z; 374([M+H]$^+$)

Example B-2

Synthesis of (1S,2S,3S,5R,6S)-2-amino-3-fluoro-2-((5-methyl-2-oxo-1,3-dioxol-4-yl)methoxy)carbonyl)bicyclo[3.1.0]hexane-6-carboxylic acid (B-2)

(1S,2S,3S,5R,6S)-6-((Allyloxy)carbonyl) 2-(((allyloxy)carbonyl)amino)-3-fluorobicyclo[3.1.0]hexane-2-carboxylic acid (B-1-1, 650 mg) and 4-(bromomethyl)-5-methyl-1,3-dioxol-2-one (384 mg) were treated in the same manner as in Example A-1 (3) and (4) to give the title compound (B-2, 262 mg) as a pale yellow solid.

$^1$H NMR (600 MHz, DMSO-d6) δ=5.05(s, 2H), 4.84-4.68 (m, 1H), 2.42-2.27(m, 1H), 2.18(s, 3H), 2.16-2.07(m, 1H), 2.07-1.99(m, 1H), 1.83-1.76(m, 1H), 1.76-1.70(m, 3H).

MS m/z; 316([M+H])$^+$

Example C-1

Synthesis of (1S,2S,3S,5R,6S)-bis((1-(((cyclohexyloxy)carbonyl)oxy)ethyl) 2-amino-3-fluorobicyclo[3.1.0]hexane-2,6-dicarboxylate (C-1)

(1S,2S,3S,5R,6S)-2-(((Allyloxy)carbonyl)amino)-3-fluorobicyclo[3.1.0]hexane-2,6-dicarboxylic acid (A-1-1, 573 mg) and 1-chloroethyl cyclohexyl carbonate (905 mg) were treated in the same manner as in Example A-1 (3) and (4) to give the title compound (C-1, 124 mg) as a yellow oil.

$^1$H NMR (600 MHz, CHLOROFORM-d) δ=6.84-6.75(m, 1H), 6.75-6.69(m, 1H), 4.85-4.55(m, 3H), 2.55-2.37(m, 1H), 2.37-2.20(m, 2H), 2.10-1.88(m, 6H), 1.79-1.70(m, 4H), 1.66-1.42(m, 13H), 1.42-1.30(m, 4H), 1.30-1.20(m, 2H).

MS m/z; 544([M+H]$^+$)

Example C-2

Synthesis of (1S,2S,3S,5R,6S)-bis((5-methyl-2-oxo-1,3-dioxol-4-yl)methyl) 2-amino-3-fluorobicyclo[3.1.0]hexane-2,6-dicarboxylate (C-2)

(1S,2S,3S,5R,6S)-2-(((Allyloxy)carbonyl)amino)-3-fluorobicyclo[3.1.0]hexane-2,6-dicarboxylic acid (A-1-1, 660 mg) and 4-(bromomethyl)-5-methyl-1,3-dioxol-2-one (639 mg) were treated in the same manner as in Example A-1 (3) and (4) to give the title compound (C-2, 207 mg) as a pale yellow oil.

$^1$H NMR (600 MHz, CHLOROFORM-d) δ=4.95(d, J=8.3 Hz, 2H), 4.82(s, 2H), 4.80-4.65(m, 1H), 2.56-2.40(m, 1H), 2.38-2.25(m, 2H), 2.20(s, 3H), 2.17(s, 3H), 2.07-1.98(m, 2H), 1.87-1.77(m, 1H).

MS m/z; 428([M+H]$^+$)

The structural formulas of Examples A-1 to A-21, B-1, B-2, C-1, C-2 and Reference Example 1 are shown in Tables 1-1 to 1-6.

TABLE 1-1

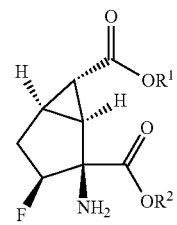

| Compound No. | R1 | R2 | Salt |
|---|---|---|---|
| Ex. A-1 | 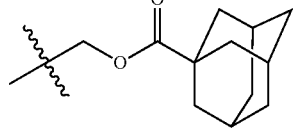 | H | |
| Ex. A-2 | 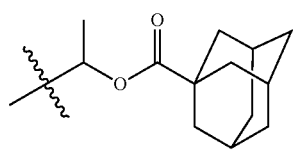 | H | |
| Ex. A-3 | 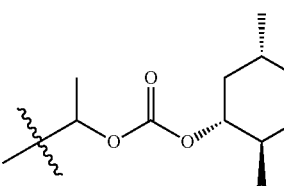 | H | |
| Ex. A-4 | 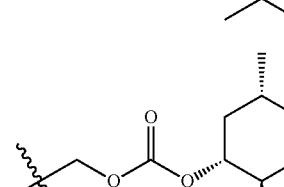 | H | |
| Ex. A-5 | 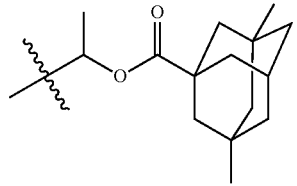 [SMILES: *C(C)OC(=O)C12CC3CC(C)(CC(C)(C3)C1)C2] | H | |
| Ex. A-6 | 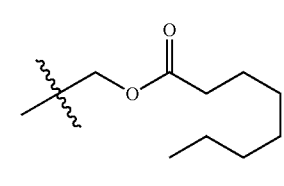 [SMILES: *COC(=O)CCCCCCC] | H | |
| Ex. A-7 | 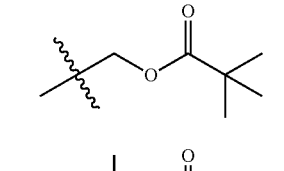 | H | |
| Ex. A-8 | 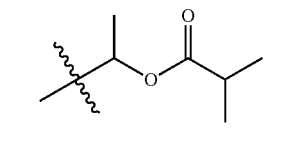 [SMILES: *C(C)OC(=O)C(C)C] | H | HCl |

TABLE 1-1-continued

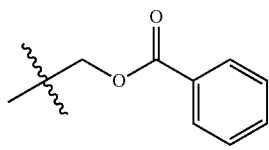 [SMILES: *COC(=O)c1ccccc1]

| Compound No. | R1 | R2 | Salt |
|---|---|---|---|
| Ex. A-9 | [benzoate -CH2-OC(O)-C6H5] | H | |

TABLE 1-2

| Compound No. | R1 | R2 | Salt |
|---|---|---|---|
| Ex. A-10 | [-CH(CH3)-O-C(O)-O-cyclohexyl] | H | |
| Ex. A-11 | [-CH(CH3)-O-C(O)-O-cyclooctyl] | H | |
| Ex. A-12 | [-CH(CH3)-O-C(O)-O-(4,4-dimethylcyclohexyl)] | H | |
| Ex. A-13 | [-CH2-O-C(O)-O-adamantyl] | H | |
| Ex. A-14 | [-CH(CH3)-O-C(O)-O-adamantyl] | H | |
| Ex. A-15 | [-CH(CH3)-O-C(O)-O-iPr] | H | $CF_3CO_2H$ |
| Ex. A-16 | [(5-methyl-2-oxo-1,3-dioxol-4-yl)methyl] | H | |

TABLE 1-2-continued

| Compound No. | R1 | R2 | Salt |
|---|---|---|---|
| Ex. A-17 | [1-(3-oxo-1,3-dihydroisobenzofuran-1-yl)] | H | HCl |

TABLE 1-3

| Compound No. | R1 | R2 | Salt |
|---|---|---|---|
| Ex. A-18 | [(R)-1-((menthyloxycarbonyl)oxy)ethyl] | H | |
| Ex. A-18-4 | [(R)-1-((menthyloxycarbonyl)oxy)ethyl] | H | $C_6H_5SO_3H$ |
| Ex. A-19 | [(S)-1-((menthyloxycarbonyl)oxy)ethyl] | H | |
| Ex. A-20 | [(R)-1-(adamantane-1-carbonyloxy)ethyl] | H | |
| Ex. A-21 | [(S)-1-(adamantane-1-carbonyloxy)ethyl] | H | |

TABLE 1-4

| Compound No. | R1 | R2 | Salt |
|---|---|---|---|
| Ex. A-18-6 | [menthyl carbonate structure] | H | CH$_3$SO$_3$H |
| Ex. A-18-7 | [menthyl carbonate structure] | H | C$_2$H$_5$SO$_3$H |
| Ex. A-18-8 | [menthyl carbonate structure] | H | p-toluene-sulfonic acid |
| Ex. A-18-9 | [menthyl carbonate structure] | H | (−)-10-camphor-sulfonic acid |

TABLE 1-5

| Compound No. | R1 | R2 | Salt |
|---|---|---|---|
| Ex. A-20-3 | [adamantane carboxylate structure] | H | CH$_3$SO$_3$H |
| Ex. A-20-4 | [adamantane carboxylate structure] | H | C$_2$H$_5$SO$_3$H |
| Ex. A-20-5 | [adamantane carboxylate structure] | H | C$_6$H$_5$SO$_3$H |
| Ex. A-20-6 | [adamantane carboxylate structure] | H | p-toluene-sulfonic acid |
| Ex. A-21-2 | [adamantane carboxylate structure] | H | HCl |

TABLE 1-6

| Compound No. | R1 | R2 | Salt |
|---|---|---|---|
| Ex. B-1 | H | [cyclohexyl carbonate structure] | HCl |
| Ex. B-2 | H | [4,5-dimethyl-1,3-dioxol-2-one methyl structure] | |
| Ex. C-1 | | [two cyclohexyl carbonate structures] | |

TABLE 1-6-continued

| Compound No. | R1 | R2 | Salt |
| --- | --- | --- | --- |
| Ex. C-2 | (structure) | (structure) | |
| Ref. Ex. 1 | Et | H | |

Example D-1

Synthesis of (1S,2S,3S,5R,6S)-2-((S)-2-amino-4-(methylthio)butanamide)-3-fluorobicyclo[3.1.0]hexane-2,6-dicarboxylic acid hydrochloride (D-1)

(1) (1S,2S,3S,5R,6S)-Dimethyl 2-amino-3-fluorobicyclo[3.1.0]hexane-2,6-dicarboxylate (D-1-1)

Thionyl chloride (3.59 mL) was added dropwise to methanol (40 mL) at −20° C. and the mixture was stirred at the same temperature for 30 minutes. (1S,2S,3S,5R,6S)-2-Amino-3-fluorobicyclo[3.1.0]hexane-2,6-dicarboxylic acid (IV, 2.00 g) was thereafter added and the mixture was heated at reflux for 4 hours. The reaction mixture was allowed to cool and then concentrated under reduced pressure. To the reaction mixture, a saturated aqueous sodium bicarbonate solution was added, and the mixture was extracted twice with chloroform. After the organic layer was dried over anhydrous sodium sulfate, the insoluble was filtered and the filtrate was concentrated under reduced pressure to give (1S,2 S,3S,5R,6S)-dimethyl 2-amino-3-fluorobicyclo[3.1.0]hexane-2,6-dicarboxylate (D-1-1, 2.03 g) as a yellow oil.

$^1$H NMR (600 MHz, CHLOROFORM-d) δ=4.86-4.71(m, 1H), 3.81(s, 3H), 3.67(s, 3H), 2.57-2.42(m, 1H), 2.33-2.23 (m, 2H), 2.05-1.96(m, 2H).

MS m/z; 232([M+H]$^+$)

(2) (1S,2S,3S,5R,6S)-Dimethyl 2-((S)-2-((tert-butoxycarbonyl)amino)-4-(methylthio)butanamide)-3-fluorobicyclo[3.1.0]hexane-2,6-dicarboxylate (D-1-2)

To a suspension of (S)-2-((tert-butoxycarbonyl)amino)-4-(methylthio)butanoic acid (600 mg) in chloroform (6 mL), N-methylmorpholine (0.265 mL) was added, isobutyl chloroformate (0.312 mL) was added dropwise at −20° C., and the mixture was stirred at the same temperature for 15 minutes. To the reaction mixture, a solution of (1S,2S,3S,5R,6S)-dimethyl 2-amino-3-fluorobicyclo[3.1.0]hexane-2,6-dicarboxylate (D-1-1, 464 mg) in chloroform (4 mL) was added dropwise at −20° C., and then the mixture was stirred at room temperature for 40 minutes. To the reaction mixture, a saturated aqueous sodium bicarbonate solution was added, and the mixture was extracted three times with chloroform. The combined organic layer was washed once with brine and then dried over anhydrous sodium sulfate. The insoluble was filtered off, the filtrate was concentrated under reduced pressure, and the resulting residue was purified by silica gel column chromatography (silica gel cartridge, hexane:ethyl acetate=100:0-0:100) to give (1S,2S,3S,5R,6S)-dimethyl 2-((S)-2-((tert-butoxycarbonyl)amino)-4-(methylthio)butanamide)-3-fluorobicyclo[3.1.0]hexane-2,6-dicarboxylate (D-1-2, 895 mg) as a colorless amorphous.

$^1$H NMR (600 MHz, CHLOROFORM-d) δ=5.37-5.20(m, 1H), 4.36-4.28(m, 1H), 3.76(s, 3H), 3.69(s, 3H), 2.64-2.51 (m, 2H), 2.38-2.25(m, 2H), 2.12(s, 4H), 2.00(br s, 2H), 1.95-1.88(m, 1H), 1.60-1.51(m, 1H), 1.46(s, 9H), 1.26(s, 2H).

MS m/z; 485([M+Na]$^+$)

(3) (1S,2S,3S,5R,6S)-2-((S)-2-((tert-Butoxycarbonyl)amino)-4-(methylthio)butanamide)-3-fluorobicyclo[3.1.0]hexane-2,6-dicarboxylic acid (D-1-3)

To a solution of (1S,2S,3S,5R,6S)-dimethyl 2-((S)-2-((tert-butoxycarbonyl)amino)-4-(methylthio)butanamide)-3-fluorobicyclo[3.1.0]hexane-2,6-dicarboxylate (D-1-2, 895 mg) in tetrahydrofuran (10 mL), a 2 mol/L aqueous sodium hydroxide solution (2.92 mL) was added at room temperature, and the mixture was stirred at the same temperature for 6 hours. The reaction mixture was washed with tert-butyl methyl ether, then acidified with 1 mol/L hydrochloric acid at 0° C., and extracted three times with ethyl acetate. The combined organic layer was dried over anhydrous sodium sulfate. The insoluble was filtered off and the filtrate was concentrated under reduced pressure to give (1S,2S,3S,5R, 6S)-2-((S)-2-((tert-butoxycarbonyl)amino)-4-(methylthio) butanamide)-3-fluorobicyclo[3.1.0]hexane-2,6-dicarboxylic acid (D-1-3, 795 mg) as a colorless amorphous.

$^1$H NMR (600 MHz, CHLOROFORM-d) δ=5.43-5.22(m, 1H), 4.40-4.30(m, 1H), 2.60-2.46(m, 2H), 2.40-2.19(m, 1H), 2.18-2.06(m, 4H), 2.02-1.90(m, 1H), 1.45(br s, 9H), 1.26(t, J=7.0 Hz, 2H).

MS m/z; 433([M−H]$^−$)

(4) (1S,2S,3S,5R,6S)-2-((S)-2-Amino-4-(methylthio)butanamide)-3-fluorobicyclo[3.1.0]hexane-2,6-dicarboxylic acid hydrochloride (D-1)

To a suspension of (1S,2S,3S,5R,6S)-2-((S)-2-((tert-butoxycarbonyl)amino)-4-(methylthio)butanamide)-3-fluorobicyclo[3.1.0]hexane-2,6-dicarboxylic acid (D-1-3, 795 mg) in ethyl acetate (5 mL), a 4 mol/L hydrogen chloride-ethyl acetate solution (11.0 mL) was added at 0° C., and the mixture was stirred at room temperature for 4 hours. The resulting solid was thereafter collected by filtration and dried to give the title compound (D-1, 543 mg) as a white solid.

$^1$H NMR (600 MHz, DEUTERIUM OXIDE) δ=5.30-5.14 (m, 1H), 4.25-4.13(m, 1H), 2.73-2.50(m, 3H), 2.50-2.42(m, 1H), 2.39-2.26(m, 1H), 2.26-2.16(m, 2H), 2.16-2.09(m, 4H), 1.95-1.84(m, 2H).

MS m/z; 335([M+H]$^+$)

Example D-2

Synthesis of (1S,2S,3S,5R,6S)-2-((S)-2-aminopropanamide)-3-fluorobicyclo[3.1.0]hexane-2,6-dicarboxylic acid hydrochloride (D-2)

(1S,2S,3S,5R,6S)-Dimethyl 2-amino-3-fluorobicyclo[3.1.0]hexane-2,6-dicarboxylate (D-1-1, 1.27 g) and (S)-2-((tert-butoxycarbonyl)amino)propanoic acid (1.10 g) were treated in the same manner as in Example D-1 (2), (3) and (4) to give the title compound (D-2, 1.50 g) as a colorless solid.
$^1$H NMR (600 MHz, DMSO-d6) δ=9.12(s, 1H), 5.36-5.12 (m, 1H), 3.97-3.82(m, 1H), 2.63-2.52(m, 1H), 2.25-2.11(m, 1H), 2.11-2.02(m, 1H), 1.89-1.82(m, 1H), 1.76-1.69(m, 1H), 1.40(d, J=7.0 Hz, 3H).
MS m/z; 275([M+H]$^+$)

Example D-3

Synthesis of (1S,2S,3S,5R,6S)-2-(2-aminoacetamide)-3-fluorobicyclo[3.1.0]hexane-2,6-dicarboxylic acid hydrochloride (D-3)

(1S,2 S,3S,5R,6S)-Dimethyl 2-amino-3-fluorobicyclo[3.1.0]hexane-2,6-dicarboxylate (D-1-1, 500 mg) and 2-((tert-butoxycarbonyl)amino)acetic acid (455 mg) were treated in the same manner as in Example D-1 (2), (3) and (4) to give the title compound (D-3, 300 mg) as a colorless solid.
$^1$H NMR (600 MHz, DMSO-d6) δ=9.18(s, 1H), 8.21-8.04 (m, 1H), 5.35-5.12(m, 1H), 3.62(s, 2H), 2.58-2.39(m, 1H), 2.24-2.11(m, 1H), 2.11-2.03(m, 1H), 1.87(br s, 1H), 1.77-1.69(m, 1H).
MS m/z; 261([M+H]$^+$)

Example D-4

Synthesis of (1S,2S,3S,5R,6S)-2-((S)-2-amino-4-methylbutanamide)-3-fluorobicyclo[3.1.0]hexane-2,6-dicarboxylic acid hydrochloride (D-4)

(1S,2S,3S,5R,6S)-Dimethyl 2-amino-3-fluorobicyclo[3.1.0]hexane-2,6-dicarboxylate (D-1-1, 500 mg) and (S)-2-((tert-butoxycarbonyl)amino) 3-methylbutanoic acid (564 mg) were treated in the same manner as in Example D-1 (2), (3) and (4) to give the title compound (D-4, 133 mg) as a colorless solid.
$^1$H NMR (600 MHz, DMSO-d6) δ=9.09(s, 1H), 5.32-5.13 (m, 1H), 3.74(d, J=4.1 Hz, 2H), 2.65-2.35(m, 1H), 2.31-2.12(m, 2H), 2.12-2.03(m, 1H), 1.93-1.82(m, 1H), 1.80-1.70 (m, 1H), 1.05-0.90(m, 6H).
MS m/z; 303([M+H]$^+$)

Example D-5

Synthesis of (1S,2S,3S,5R,6S)-2-((S)-2,6-diaminohexanamide)-3-fluorobicyclo[3.1.0]hexane-2,6-dicarboxylic acid hydrochloride (D-5)

(1S,2S,3S,5R,6S)-Dimethyl 2-amino-3-fluorobicyclo[3.1.0]hexane-2,6-dicarboxylate (D-1-1, 200 mg) and (S)-2,6-bis((tert-butoxycarbonyl)amino)hexanoic acid (360 mg) were treated in the same manner as in Example D-1 (2), (3) and (4) to give the title compound (D-5, 281 mg) as a colorless solid.
$^1$H NMR (600 MHz, DMSO-d6) δ=9.21(s, 1H), 8.27(br s, 1H), 8.03(br s, 1H), 5.32-5.13(m, 1H), 3.95-3.85(m, 1H), 2.81-2.70(m, 2H), 2.62-2.40(m, 1H), 2.27-2.10(m, 1H), 2.07 (dd, J=2.7, 6.4 Hz, 1H), 1.95-1.69(m, 4H), 1.66-1.51(m, 2H), 1.47-1.36(m, 2H), 1.17(t, J=7.2 Hz, 2H).
MS m/z; 332([M+H]$^+$)

Example D-6

Synthesis of (1S,2S,3S,5R,6S)-2-((2S,3S)-2-amino-3-methylpentanamide)-3-fluorobicyclo[3.1.0]hexane-2,6-dicarboxylic acid hydrochloride (D-6)

(1S,2S,3S,5R,6S)-Dimethyl 2-amino-3-fluorobicyclo[3.1.0]hexane-2,6-dicarboxylate (D-1-1, 500 mg) and (2S,3S)-2-((tert-butoxycarbonyl)amino)-3-methylpentanoic acid (600 mg) were treated in the same manner as in Example D-1 (2), (3) and (4) to give the title compound (D-6, 662 mg) as a colorless solid.
$^1$H NMR (600 MHz, METHANOL-d4) δ=5.40-5.21(m, 1H), 3.84(d, J=4.5 Hz, 1H), 2.75-2.53(m, 1H), 2.37-2.17(m, 2H), 2.08-1.86(m, 3H), 1.76-1.57(m, 1H), 1.32-1.17 (m, 1H), 1.10(d, J=7.0 Hz, 3H), 1.04-0.93(m, 3H).
MS m/z; 317([M+H])$^+$

Example D-7

Synthesis of (1S,2S,3S,5R,6S)-2-((S)-2-amino-4-methylpentanamide)-3-fluorobicyclo[3.1.0]hexane-2,6-dicarboxylic acid hydrochloride (D-7)

(1S,2S,3S,5R,6S)-Dimethyl 2-amino-3-fluorobicyclo[3.1.0]hexane-2,6-dicarboxylate (D-1-1, 300 mg) and (S)-2-((tert-butoxycarbonyl)amino)-4-methylpentanoic acid (360 mg) were treated in the same manner as in Example D-1 (2), (3) and (4) to give the title compound (D-7, 240 mg) as a colorless solid.
$^1$H NMR (600 MHz, METHANOL-d4) δ=5.42-5.23(m, 1H), 4.01-3.91(m, 1H), 2.74-2.56(m, 1H), 2.34-2.19(m, 2H), 2.00-1.89(m, 2H), 1.86-1.75(m, 2H), 1.73-1.63(m, 1H), 1.03 (d, J=6.2 Hz, 3H), 1.01(d, J=6.2 Hz, 3H).
MS m/z; 317([M+H]$^+$)

Example D-8

Synthesis of (1S,2S,3S,5R,6S)-2-((S)-2-((S)-2-aminopropanamide)propanamide)-3-fluorobicyclo[3.1.0]hexane-2,6-dicarboxylic acid hydrochloride (D-8)

(1S,2S,3S,5R,6S)-Dimethyl 2-amino-3-fluorobicyclo[3.1.0]hexane-2,6-dicarboxylate (D-1-1, 300 mg) and (S)-2-((S)-2-(tert-butoxycarbonyl)propanamide)propanoic acid (405 mg) were treated in the same manner as in Example D-1 (2), (3) and (4) to give the title compound (D-8, 452 mg) as a colorless solid.
$^1$H NMR (600 MHz, METHANOL-d4) δ=5.37-5.20(m, 1H), 4.57(d, J=7.0 Hz, 1H), 3.91(d, J=7.0 Hz, 1H), 2.70-2.54(m, 1H), 2.31-2.18(m, 2H), 1.97-1.86(m, 2H), 1.48(d, J=7.0 Hz, 3H), 1.39(d, J=7.0 Hz, 3H).
MS m/z; 346([M+H])$^+$

Example D-9

Synthesis of (1S,2S,3S,5R,6S)-2-((S)-2-amino-3-phenylpropanamide)-3-fluorobicyclo[3.1.0]hexane-2,6-dicarboxylic acid hydrochloride (D-9)

(1S,2S,3S,5R,6S)-Dimethyl 2-amino-3-fluorobicyclo[3.1.0]hexane-2,6-dicarboxylate (D-1-1, 150 mg) and (S)-

2-((S)-2-(tert-butoxycarbonyl)-3-phenylpropanoic acid (207 mg) were treated in the same manner as in Example D-1 (2), (3) and (4) to give the title compound (D-9, 205 mg) as a colorless solid.

$^1$H NMR (600 MHz, METHANOL-d4) δ=7.43-7.28(m, 5H), 5.41-5.25(m, 1H), 4.24-4.15 (m, 1H), 3.46-3.37(m, 1H), 3.05-2.95(m, 1H), 2.73-2.58(m, 1H), 2.38-2.21(m, 2H), 2.04-1.92(m, 2H).

MS m/z; 351([M+H]$^+$)

Example D-10

Synthesis of (1S,2S,3S,5R,6S)-3-fluoro-2-((S)-pyrrolidine-2-(carboxyamide))bicyclo[3.1.0]hexane-2,6-dicarboxylic acid hydrochloride (D-10)

(1S,2S,3S,5R,6S)-Dimethyl 2-amino-3-fluorobicyclo[3.1.0]hexane-2,6-dicarboxylate (D-1-1, 150 mg) and (S)-1-(tert-butoxycarbonyl)pyrrolidine-2-carboxylic acid (168 mg) were treated in the same manner as in Example D-1 (2), (3) and (4) to give the title compound (D-10, 182 mg) as a colorless solid.

$^1$H NMR (600 MHz, METHANOL-d4) δ=5.40-5.23(m, 1H), 4.32(dd, J=6.6, 8.7 Hz, 1H), 3.46-3.37(m, 1H), 3.34-3.25(m, 1H), 2.73-2.59(m, 1H), 2.51-2.41(m, 1H), 2.33-2.22 (m, 2H), 2.21-2.13(m, 1H), 2.11-2.00(m, 2H), 2.00-1.95(m, 1H), 1.94-1.89(m, 1H).

MS m/z; 301([M+H]$^+$)

Example D-11

Synthesis of (1S,2S,3S,5R,6S)-2-((R)-2-amino-4-(methylthio)butanamide)-3-fluorobicyclo[3.1.0]hexane-2,6-dicarboxylic acid hydrochloride (D-11)

(1S,2S,3S,5R,6S)-Dimethyl 2-amino-3-fluorobicyclo[3.1.0]hexane-2,6-dicarboxylate (D-1-1, 200 mg) and (R)-2-((tert-butoxycarbonyl)amino)-4-(methylthio)butanoic acid (258 mg) were treated in the same manner as in Example D-1 (2), (3) and (4) to give the title compound (D-11, 54.0 mg) as a colorless solid.

$^1$H NMR (600 MHz, DMSO-d6) δ=9.28(s, 1H), 5.35-5.12 (m, 1H), 4.01-3.93(m, 1H), 2.66-2.36(m, 3H), 2.29-2.10(m, 2H), 2.08-1.82(m, 6H), 1.73-1.64(m, 1H).

MS m/z; 335([M+H]$^+$)

Example D-12

Synthesis of (1S,2S,3S,5R,6S)-2-((R)-2-aminopropanamide)-3-fluorobicyclo[3.1.0]hexane-2,6-dicarboxylic acid hydrochloride (D-12)

(1S,2S,3S,5R,6S)-Dimethyl 2-amino-3-fluorobicyclo[3.1.0]hexane-2,6-dicarboxylate (D-1-1, 200 mg) and (R)-2-((tert-butoxycarbonyl)amino)propanoic acid (196 mg) were treated in the same manner as in Example D-1 (2), (3) and (4) to give the title compound (D-12, 128 mg) as a colorless solid.

$^1$H NMR (600 MHz, DMSO-d6) δ=9.15(s, 1H), 5.34-5.11 (m, 1H), 3.98-3.85(m, 1H), 2.56-2.40(m, 1H), 2.23-2.05(m, 2H), 1.91-1.83(m, 1H), 1.75-1.65(m, 1H), 1.35(d, J=7.0 Hz, 3H).

MS m/z; 275([M+H]$^+$)

Example D-13

Synthesis of (1S,2S,3S,5R,6S)-2-((1-(((cyclohexyloxy)carbonyl)oxy)ethoxy)carbonyl)amino-3-fluorobicyclo[3.1.0]hexane-2,6-dicarboxylic acid (D-13)

(1) (1S,2S,3S,5R,6S)-2-((tert-Butoxycarbonyl)amino)-3-fluorobicyclo[3.1.0]hexane-2,6-dicarboxylic acid (D-13-1)

(1S,2S,3S,5R,6S)-2-Amino-3-fluorobicyclo[3.1.0] hexane-2,6-dicarboxylic acid (IV, 1.00 g) and di-tert-butoxycarbonyl (4.30 g) were treated in the same manner as in Example A-1 (1) to give (1S,2 S,3S,5R,6S)-2-((tert-butoxycarbonyl)amino)-3-fluorobicyclo[3.1.0]hexane-2,6-dicarboxylic acid (D-13-1, 1.30 g) as a colorless amorphous.

(2) (1S,2S,3S,5R,6S)-Diallyl 2-((tert-butoxycarbonyl)amino)-3-fluorobicyclo[3.1.0]hexane-2,6-dicarboxylate (D-13-2)

To a solution of (1S,2S,3S,5R,6S)-2-((tert-butoxycarbonyl)amino)-3-fluorobicyclo[3.1.0]hexane-2,6-dicarboxylic acid (D-13-1, 1.30 g) in N,N-dimethylformamide (25 mL), allyl bromide (1.09 mL) and potassium carbonate (1.18 g) were added at room temperature, and the mixture was stirred at the same temperature for 18 hours. To the reaction solution, water was added, and the mixture was extracted three times with ethyl acetate. The combined organic layer was washed three times with 5% saline and once with brine, sequentially. After the organic layer was dried over anhydrous sodium sulfate, the insoluble was filtered, the filtrate was concentrated under reduced pressure, and the resulting residue was purified by silica gel column chromatography (silica gel cartridge, hexane:ethyl acetate=100:0-60:40) to give (1S,2S,3S,5R,6S)-diallyl 2-((tert-butoxycarbonyl) amino)-3-fluorobicyclo[3.1.0]hexane-2,6-dicarboxylate (D-13-2, 1.49 g) as a colorless oil.

(3) (1S,2S,3S,5R,6S)-Diallyl 2-amino-3-fluorobicyclo[3.1.0]hexane-2,6-dicarboxylate (D-13-3)

To (1S,2S,3S,5R,6S)-diallyl 2-((tert-butoxycarbonyl) amino)-3-fluorobicyclo[3.1.0]hexane-2,6-dicarboxylate (D-13-2, 1.49 g), a 4 mol/L hydrogen chloride-ethyl acetate solution (24 mL) was added at 0° C., and the mixture was stirred at room temperature for 18 hours. The reaction solution was thereafter concentrated under reduced pressure, a saturated aqueous sodium bicarbonate solution was added, and the mixture was extracted three times with ethyl acetate. After the combined organic layer was washed once with brine and dried over anhydrous sodium sulfate, the insoluble was filtered off and the filtrate was concentrated under reduced pressure to give (1S,2S,3S,5R,6S)-diallyl 2-amino-3-fluorobicyclo[3.1.0]hexane-2,6-dicarboxylate (D-13-3, 949 mg).

(4) (1S,2S,3S,5R,6S)-Diallyl 2-((1-(((cyclohexyloxy)carbonyl)oxy)ethoxy)carbonyl)amino-3-fluorobicyclo[3.1.0]hexane-2,6-dicarboxylate (D-13-4)

To a solution of (1S,2S,3S,5R,6S)-diallyl 2-amino-3-fluorobicyclo[3.1.0]hexane-2,6-dicarboxylate (D-13-3, 880 mg) in N,N-dimethylformamide (20 mL), cesium carbonate (4.05 g) and cyclohexyl (1-iodoethyl)carbonate (2.23 g) were added at room temperature, and the mixture was stirred at the same temperature for 2 hours while carbon dioxide was being injected into the mixture. This injection was thereafter stopped and the mixture was stirred at the same temperature for 18 hours. To the reaction solution, water was added, and the mixture was extracted three times with ethyl acetate. After the combined organic layer was washed three times with 5% saline and once with brine, sequentially, and dried over anhydrous sodium sulfate, the insoluble was filtered off, the filtrate was concentrated under reduced pressure, and the resulting residue was purified by silica gel column chromatography (silica gel cartridge, hexane:ethyl acetate=100:0-50:50) to give (1S,2S,3S,5R,6S)-diallyl 2-((1-(((cyclohexyloxy)carbonyl)oxy)ethoxy)carbonyl) amino-3-fluorobicyclo[3.1.0]hexane-2,6-dicarboxylate (D-13-4, 840 mg) as a yellow oil.

(5) (1S,2S,3S,5R,6S)-2-((1-(((Cyclohexyloxy)carbonyl)oxy)ethoxy)carbonyl)amino-3-fluorobicyclo[3.1.0]hexane-2,6-dicarboxylic acid (D-13)

(1S,2S,3S,5R,6S)-Diallyl 2-((1-(((cyclohexyloxy)carbonyl)oxy)ethoxy)carbonyl)amino-3-fluorobicyclo[3.1.0]hexane-2,6-dicarboxylate (D-13-4, 958 mg) was treated in the same manner as in Example A-1 (4) to give the title compound (D-13, 537 mg) as a colorless amorphous.
$^1$H NMR (600 MHz, CHLOROFORM-d) δ=6.79-6.62(m, 1H), 5.85(br s, 1H), 5.36-5.14(m, 1H), 4.73-4.55(m, 1H), 2.69-2.46(m, 1H), 2.45-2.26(m, 1H), 2.20-1.84(m, 4H), 1.80-1.68(m, 2H), 1.59-1.42(m, 5H), 1.41-1.18(m, 6H).
MS m/z; 440([M+Na]$^+$)

Example D-14

Synthesis of (1S,2S,3S,5R,6S)-3-fluoro-2-((1-(isobutyloxy)ethoxy)carbonyl)aminobicyclo[3.1.0]hexane-2,6-dicarboxylic acid (D-14)

(1S,2S,3S,5R,6S)-Diallyl 2-amino-3-fluorobicyclo[3.1.0]hexane-2,6-dicarboxylate (D-13-3, 800 mg) and 1-iodoethyl isobutyrate (1.37 g) were treated in the same manner as in Example D-13 (4) and (5) to give (1S,2S,3S,5R,6S)-3-fluoro-2-((1-(isobutyloxy)ethoxy)carbonyl)aminobicyclo[3.1.0]hexane-2,6-dicarboxylic acid (D-14, 87 mg) as a colorless amorphous.
$^1$H NMR (600 MHz, DMSO-d6) δ=8.51(br s, 1H), 6.69-6.49(m, 1H), 5.25-4.98(m, 1H), 2.49-2.36(m, 1H), 2.22-2.06 (m, 1H), 2.05-1.90(m, 1H), 1.79(br s, 1H), 1.75-1.62(m, 1H), 1.45-1.34(m, 3H), 1.05(m, 6H).
MS m/z; 384([M+Na]$^+$)

Example D-15

Synthesis of (1S,2S,3S,5R,6S)-3-fluoro-2-((((5-methyl-2-oxo-1,3-dioxol-4-yl)methoxy)carbonyl)amino)bicyclo[3.1.0]hexane-2,6-dicarboxylic acid (D-15)

(1) (1S,2S,3S,5R,6S)-Diallyl 3-fluoro-2-((((5-methyl-2-oxo-1,3-dioxol-4-yl)methoxy)carbonyl)amino)bicyclo[3.1.0]hexane-2,6-dicarboxylate (D-15-1)

To a solution of triphosgene (35 mg) in chloroform (4 mL), 4-(hydroxymethyl)-5-methyl-1,3-dioxol-2-one (45.9 mg) and a solution of N,N-diisopropylethylamine (0.18 mL) in tetrahydrofuran (4 mL) were added at room temperature. After the mixture was stirred at the same temperature for 30 minutes, a solution of (1S,2S,3S,5R,6S)-diallyl 2-amino-3-fluorobicyclo[3.1.0]hexane-2,6-dicarboxylate (D-13-3, 100 mg) in chloroform (4 mL) was added to the reaction mixture, and the mixture was stirred at the same temperature for 3 hours. To the reaction mixture, ethyl acetate was added, and the organic layer was washed once with water and once with brine, sequentially. After the organic layer was dried over anhydrous sodium sulfate, the insoluble was filtered, the filtrate was concentrated under reduced pressure, and the resulting residue was purified by silica gel column chromatography (silica gel cartridge, hexane:ethyl acetate=90:10-70:30) to give (1S,2S,3S,5R,6S)-diallyl 3-fluoro-2-((((5-methyl-2-oxo-1,3-dioxol-4-yl)methoxy)carbonyl)amino) bicyclo[3.1.0]hexane-2,6-dicarboxylate (D-15-1, 60.0 mg) as a colorless amorphous.

(2) (1S,2S,3S,5R,6S)-3-Fluoro-2-((((5-methyl-2-oxo-1,3-dioxol-4-yl)methoxy)carbonyl)amino)bicyclo[3.1.0]hexane-2,6-dicarboxylic acid (D-15)

(1S,2S,3S,5R,6S)-Diallyl 3-fluoro-2-((((5-methyl-2-oxo-1,3-dioxol-4-yl)methoxy)carbonyl)amino)bicyclo[3.1.0]hexane-2,6-dicarboxylate (D-15-1, 1.25 g) was treated in the same manner as in Example A-1 (4) to give the title compound (D-15, 94 mg) as a colorless solid.
$^1$H NMR (600 MHz, DMSO-d6) δ=5.25-5.07(m, 1H), 4.88(s, 2H), 2.55-2.44(m, 1H), 2.21-2.07(m, 4H), 2.02-1.94 (m, 1H), 1.83-1.75(m, 1H), 1.72-1.65(m, 1H).
MS m/z; 382([M+Na]$^+$)

Example D-16

Synthesis of (1S,2S,3S,5R,6S)-3-fluoro-6-((1-(isobutyloxy)ethoxy)carbonyl)-2-(((1-(isobutyloxy)ethoxy)carbonyl)amino)bicyclo[3.1.0]hexane-2-carboxylic acid (D-16)

(1S,2S,3S,5R,6S)-2-Amino-3-fluoro-6-((1-(isobutyloxy)ethoxy)carbonyl)bicyclo[3.1.0]hexane-2-carboxylic acid hydrochloride (A-8, 152 mg) and 1-iodoethyl isobutyrate (208 mg) were treated in the same manner as in Example D-13 (4) and (5) to give the title compound (D-16, 108 mg) as a colorless amorphous.
$^1$H NMR (600 MHz, DMSO-d6) δ=8.68-8.51(m, 1H), 6.76-6.65(m, 2H), 6.65-6.57(m, 2H), 5.23-5.05(m, 1H), 2.61-2.39(m, 3H), 2.27-2.13(m, 1H), 2.11-1.97(m, 1H), 1.95-1.82(m, 1H), 1.81-1.69(m, 1H), 1.46-1.35(m, 6H), 1.13-0.98(m, 12H).
MS m/z; 498([M+Na])$^+$ Example D-17

Synthesis of (1S,2S,3S,5R,6S)-3-fluoro-6-(((5-methyl-2-oxo-1,3-dioxol-4-yl)methoxy)carbonyl)-2-(((((5-methyl-2-oxo-1,3-dioxol-4-yl)methoxy)carbonyl)amino)bicyclo[3.1.0]hexane-2-carboxylic acid (D-17)

(1S,2S,3S,5R,6S)-2-Amino-3-fluoro-6-(((5-methyl-2-oxo-1,3-dioxol-4-yl)methoxy)carbonyl)bicyclo[3.1.0]hexane-2-carboxylic acid (A-16, 340 mg) and 4-(hydroxymethyl)-5-methyl-1,3-dioxol-2-one (154 mg) were treated in the same manner as in Example D-15 (1) to give the title compound (D-17, 53.0 mg) as a colorless solid.
$^1$H NMR (600 MHz, DMSO-d6) δ=5.25-5.09(m, 1H), 4.99-4.86(m, 4H), 2.56-2.43(m, 1H), 2.23-2.10(m, 7H), 2.08-2.01(m, 1H), 1.95-1.87(m, 1H), 1.81-1.73(m, 1H).

MS m/z; 494([M+Na]$^+$)

Examples D-1 to D-17 are shown in Tables 2-1 and 2-2.

TABLE 2-1

| Compound No. | R1 | R3 | Salt |
|---|---|---|---|
| Ex. D-1 | H | (methionine side chain structure) | HCl |
| Ex. D-2 | H | (alanine side chain structure) | HCl |
| Ex. D-3 | H | (glycine side chain structure) | HCl |
| Ex. D-4 | H | (valine side chain structure) | HCl |
| Ex. D-5 | H | (lysine side chain structure) | 2HCl |
| Ex. D-6 | H | (isoleucine side chain structure) | HCl |
| Ex. D-7 | H | (leucine side chain structure) | HCl |
| Ex. D-8 | H | (Ala-Ala dipeptide structure) | HCl |
| Ex. D-9 | H | (phenylalanine side chain structure) | HCl |
| Ex. D-10 | H | (proline structure) | HCl |

TABLE 2-2

| Compound No. | R1 | R3 | Salt |
|---|---|---|---|
| Ex. D-11 | H | (methionine side chain structure) | HCl |
| Ex. D-12 | H | (alanine side chain structure) | HCl |

TABLE 2-2-continued

| Compound No. | R1 | R3 | Salt |
|---|---|---|---|
| Ex. D-13 | H | 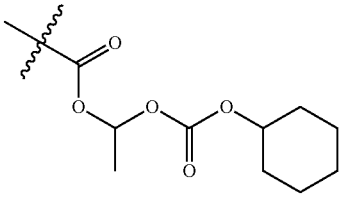 [SMILES: *C(=O)OC(C)OC(=O)OC1CCCCC1] | |
| Ex. D-14 | H | 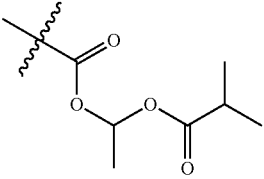 [SMILES: *C(=O)OC(C)OC(=O)C(C)C] | |
| Ex. D-15 | H | 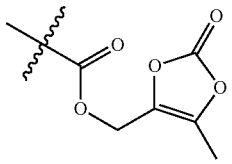 [SMILES: *C(=O)OCc1oc(=O)oc1C] | |
| Ex. D-16 | 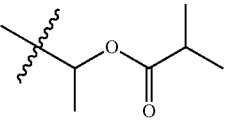 [SMILES: *C(C)OC(=O)C(C)C] | 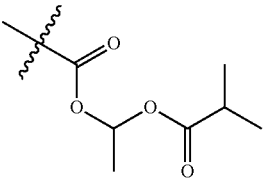 [SMILES: *C(=O)OC(C)OC(=O)C(C)C] | |
| Ex. D-17 | 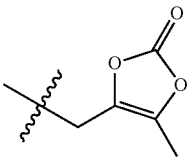 [SMILES: *Cc1oc(=O)oc1C] | 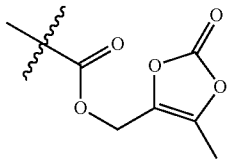 [SMILES: *C(=O)OCc1oc(=O)oc1C] | |

Test 1: Solution Stability Test

Inventive Compounds (I) were tested for their stability in solutions simulating the gastric and small intestine's digestive fluids identified below.

The percent residues of Inventive Compounds (I) in a hydrochloric acid solution (pH 1.2) and 20 mM phosphate buffer (pH 6.5) were measured in accordance with the following test method.

A test compound was dissolved in a hydrochloric acid solution (pH 1.2) containing hydrochloric acid and sodium chloride or a 20 mM phosphate buffer (pH 6.5) containing disodium hydrogenphosphate, sodium dihydrogenphosphate and sodium chloride to prepare a solution with a concentration of about 50 μg/mL (near the solubility if undissolved). The solution was incubated at 37° C. for an hour and the compound's concentration before and after the incubation was quantified by high-performance liquid chromatography to calculate the percent residue of the compound.

The percent residues of representative compounds in the hydrochloric acid solution (pH 1.2) and the 20 mM phosphate buffer (pH 6.5) are shown in the following Table 3.

TABLE 3

| Compound No. | Compound's percent residue (%) | |
|---|---|---|
| | pH 1.2 | pH 6.5 |
| Ex. A-1 | 100 | 99 |
| Ex. A-2 | 101 | 101 |
| Ex. A-3 | 100 | 100 |
| Ex. A-4 | 99 | 98 |
| Ex. A-7 | 100 | 99 |
| Ex. A-8 | 100 | 101 |
| Ex. A-10 | 100 | 97 |
| Ex. A-13 | 93 | 93 |
| Ex. A-14 | 95 | 97 |
| Ex. A-15 | 102 | 101 |
| Ex. A-16 | 99 | 98 |
| Ex. A-17 | 99 | 97 |
| Ex. D-1 | 103 | 102 |
| Ex. D-2 | 100 | 103 |
| Ex. D-3 | 100 | 102 |
| Ex. D-4 | 101 | 100 |
| Ex. D-6 | 101 | 101 |
| Ex. D-7 | 99 | 102 |

As demonstrated above, Inventive Compounds were highly stable in the solutions simulating the gastric and small intestine's digestive fluids, so it could be assumed that they would exist as a stable prodrug form in the digestive tract.

Test 2: Test for Generation of Compound (IV) in Hepatic Microsomes

A test to determine the percent generation of Compound (IV) in human and monkey hepatic microsomes was conducted for Inventive Compounds (I) in accordance with the following method. As a control for comparison, an ethyl ester form of Compound (IV) (Reference Example 1) was used.

A test compound was incubated (37° C.×15 min) in a 0.250 M phosphate buffer (pH 7.4) containing 69 mM KCl, together with a human hepatic microsome (Ms) fraction (Xenotech/H630B/lot, 0810472) or a monkey Ms fraction (BD Biosciences/452413/lot, 94518) in the presence of a NADPH generation system (0.16 mM NADP+, 2.4 mM $MgCl_2$, 1.5 mM glucose-6-phosphate). The final concentrations of the test compound and hepatic Ms protein were adjusted to 3 μM and 1 mg protein/mL, respectively. To the incubated reaction mixture, 2 volumes of DMSO was added, followed by stirring and centrifugation at 3000 rpm (4° C.×10 min) The resulting supernatant was subjected to analysis by a liquid chromatography-tandem mass spectrometry (LC-MS/MS) system. The lower quantitation limit was 0.3 μM for both the test compound and Compound (IV).

The data for percent generation of Compound (IV) in human and monkey hepatic microsomes are shown in the following Table 4 with respect to representative compounds.

TABLE 4

| Compound No. | Percent generation (%) of Compound IV in hepatic microsomes | |
|---|---|---|
| | human | monkey |
| Ex. A-1 | 100 | 90 |
| Ex. A-2 | 100 | 82 |
| Ex. A-3 | 101 | 78 |
| Ex. A-4 | 94 | 72 |
| Ex. A-5 | 72 | NT |
| Ex. A-6 | 90 | NT |
| Ex. A-7 | 19 | NT |
| Ex. A-8 | 36 | 38 |
| Ex. A-9 | 56 | NT |
| Ex. A-10 | 69 | 97 |
| Ex. A-11 | 93 | NT |
| Ex. A-12 | 94 | NT |
| Ex. A-13 | 86 | 75 |
| Ex. A-14 | 51 | NT |
| Ex. A-15 | 22 | NT |
| Ex. A-16 | 29 | 46 |
| Ex. A-17 | 86 | 80 |
| Ex. A-18 | 84 | NT |
| Ex. A-18-4 | NT | 75 |
| Ex. A-19 | 87 | NT |
| Ex. A-21 | 87 | 93 |
| Ref. Ex. 1 | <10 | NT |

NT: Not Tested

The compound of Reference Example 1 was converted by the human hepatic microsome to Compound (IV) at a very low level, approximately 100% remaining unchanged (Reference Example 1). On the other hand, Invention Compounds were converted to Compound (IV) at high levels and the conversion proceeded in both the human and monkey hepatic microsomes, thus permitting assumption of the conversion from the prodrugs to their parent compound.

Test 3: Test for Generation of Compound (IV) in Sera

A test to determine the percent generation of Compound (IV) in human and monkey sera was conducted for Inventive Compounds (I) in accordance with the following method. As a control for comparison, An ethyl ester form of Compound (IV) (Reference Example 1) was used.

A test compound was added to human or monkey serum to give a concentration of 3 μM and the mixture was incubated at 37° C. for a specified period of time. Subsequently, to 50 μL of each incubated sample, 200 μL of a liquid acetonitrile/methanol mixture containing an internal standard substance was added, followed by stirring and centrifugation (4° C.×10 min). The resulting supernatant was subjected to LC-MS/MS analysis. The lower quantitation limit was 0.03 μM for both the test compound and Compound (IV).

The data for percent generation of Compound (IV) in human and monkey sera are shown in the following Table 5 with respect to representative compounds.

TABLE 5

| Compound No. | Percent generation (%) of Compound IV in sera | |
|---|---|---|
| | human | monkey |
| Ex. A-16 | 75 | 80 |
| Ex. A-17 | 37 | NT |
| Ref. Ex. 1 | <5 | NT |

NT: Not Tested

The compound of Reference Example 1 was converted by the human serum to Compound (IV) at a very low level. On the other hand, Invention Compounds were converted to Compound (IV) at high levels and the conversion proceeded in both the human and monkey sera, thus permitting assumption of the conversion from the prodrugs to their parent compound.

Test 4: Test for Determining the Percent Generation of Compound (IV) in Human Small Intestine S9

A test to determine the percent generation of Compound (IV) in human intestine S9 was conducted for Inventive Compounds (I) in accordance with the following method.

Inventive Compounds were incubated (37° C.×1 hr) in a 0.1 M phosphate buffer (pH 7.4) together with a human intestine S9 fraction (Xenotech, LLC/CP710571/Lot, 710571) in the presence of $Mg^{2+}$ (5 mM), $Ca^{2+}$ (5 mM) and $Zn^{2+}$ (0.1 mM). The final concentrations of each Inventive Compound and the small intestine S9 protein were adjusted to 3 μM and 1 mg protein/mL, respectively. To the incubated reaction mixture, 3 volumes of DMSO was added, followed by stirring and centrifugation at 3000 rpm (4° C.×10 min). The resulting supernatant was subjected to analysis by a liquid chromatography-tandem mass spectrometry (LC-MS/MS) system. The lower quantitation limit was 0.3 μM for both Inventive Compounds (I) and Compound (IV).

The LC-MS/MS system used in the measurement was equipped with Waters XBridge Amide (3.5 μm, 50 mm×4.6 mm I.D.), Waters Atlantis T3 (3 μm, 50 mm×4.6 mm I.D.), or Shimadzu Shim-pack XR-ODS (2.2 μm, 30 mm×3.0 mm I.D.) as a separation column. The mobile phase was a 0.1% formic acid/acetonitrile solution or a 0.1% formic acid/methanol solution (flow rate: 0.7-1.3 mL/min) and the analyte was eluted in a linear gradient mode. MS/MS detection of Inventive Compounds (I) and Compound (IV)

was performed using an API4000 or Triple quad 5500 system with TurbolonSpray interface (both being products of AB SCIEX) in either a positive or negative ion detection mode. The percent generation of Compound (IV) in human small intestine S9 is shown in the following Table 6 with respect to Inventive Compounds.

TABLE 6

| Compound No. | Percent generation (%) of Compound IV in human small intestine S9 |
|---|---|
| Ex. D-1 | 20.9 |
| Ex. D-2 | 17.8 |
| Ex. D-3 | <10 |
| Ex. D-4 | <10 |
| Ex. D-5 | 25.9 |
| Ex. D-6 | <10 |
| Ex. D-7 | 11.7 |
| Ex. D-8 | 11.7 |
| Ex. D-9 | <10 |
| Ex. D-10 | <10 |
| Ex. D-11 | <10 |

As it turned out, conversion of the tested Inventive Compounds (I) to Compound (IV) proceeded in human small intestine S9.

Test 5: Measurement of Plasma Concentrations of Compound (IV) in Monkey

A test to measure the plasma concentration of Compound (IV) upon oral administration of Compound (IV) and Inventive Compounds (I) was conducted in accordance with the following method.

Compound (IV) or Inventive Compounds (I) was orally administered to male cynomolgus monkeys (fed condition) at a dose of 4.92 µmol/kg (vehicle: 0.5% methyl cellulose (MC) solution; administered at a dose of 5 mL/kg).

Two and 4 hours after the oral administration, approximately 0.7 mL of blood was taken from the cephalic vein (anticoagulant: EDTA-2K). The plasma recovered by centrifugation (3000 rpm, 4° C.×10 min) was stored frozen at −80° C. until use for analysis. In the case of analysis, 50 µL of the plasma sample was thawed under cooling with ice and after adding 200 µL of a liquid acetonitrile/methanol mixture containing an internal standard substance, the resulting mixture was stirred and centrifuged (4° C.×10 min); the resulting supernatant was subjected to LC-MS/MS analysis. The lower quantitation limits of Inventive Compounds (I) and Compound (IV) were 1 ng/mL and 3 ng/mL, respectively.

The data for the plasma concentration of Compound (IV) after oral administration of representative compounds are shown in the following Table 7.

TABLE 7

| | Concentration (ng/mL) of Compound IV in monkey plasma | |
|---|---|---|
| Compound No. | After 2 hr | After 4 hr |
| Compound IV | 8.15 | 18.8 |
| Ex. A-1 | 197 | 270 |
| Ex. A-2 | 305 | 302 |
| Ex. A-3 | 277 | 271 |
| Ex. A-10 | 94.9 | 119 |
| Ex. A-16 | 55.4 | 52.0 |
| Ex. A-18-4 | 309 | 412 |
| Ex. A-21 | 364 | 387 |
| Ex. D-1 | 141 | 128 |

As shown in the foregoing, the orally administered Inventive Compounds (I) recorded outstanding improvements in the plasma concentration of Compound (IV) over the orally administered Compound (IV).

Industrial Applicability

It has been revealed that Inventive Compounds are very useful as prodrugs of Compound (IV) which has a strong action on group 2 metabotropic glutamate receptors. Hence, Inventive Compounds or pharmaceutically acceptable salts thereof can be used as agents for treatment or prevention of conditions that are controlled by group 2 metabotropic glutamate receptor agonists, such as schizophrenia, anxiety disorder and its related conditions, depression, bipolar disorder, epilepsy and other neuropsychiatric conditions, and drug dependence, cognitive disorders, Alzheimer's disease, Huntington's chorea, Parkinson's disease, movement disorders associated with muscular rigidity, cerebral ischemia, cerebral insufficiency, spinal cord disorders, cephalopathy and other neurological conditions.

The invention claimed is:

1. A compound represented by formula (I):

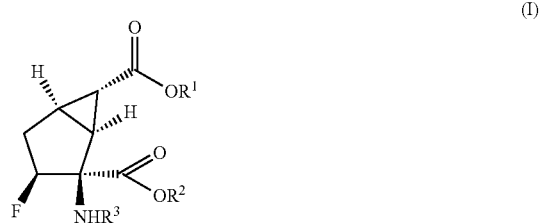

(I)

wherein $R^1$ and $R^2$, which may be the same or different, are each a hydrogen atom, —$(CR^4R^{4'})$—O—CO—$R^5$, —$(CR^6R^{6'})$—O—CO—O—$R^7$, (IIa) or (IIb):

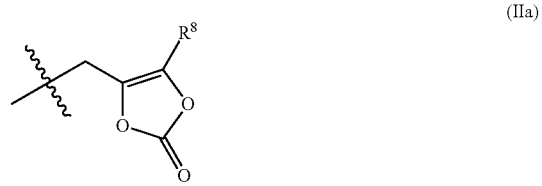

(IIa)

(IIb)

$R^3$ is a hydrogen atom, —CO—O—$(CR^9R^{9\prime})$—O—CO—$R^{10}$, —CO—O—$(CR^9R^{9\prime})$—O—CO—O—$R^{11}$, or (III):

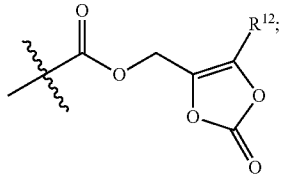
(III)

wherein $R^4$ and $R^{4\prime}$, which may be the same or different, are each a hydrogen atom or a $C_{1-6}$ alkyl group;

$R^5$ is a $C_{1-10}$ alkyl group, a $C_{3-8}$ cycloalkyl group optionally substituted with one to three $C_{1-6}$ alkyl groups, an adamantyl group optionally substituted with one to three $C_{1-6}$ alkyl groups, or a phenyl group optionally substituted with one to three groups selected from a halogen atom and a $C_{1-6}$ alkyl group;

$R^6$ and $R^{6\prime}$, which may be the same or different, are each a hydrogen atom or a $C_{1-6}$ alkyl group;

$R^7$ is a $C_{1-10}$ alkyl group, a $C_{3-8}$ cycloalkyl group optionally substituted with one to three $C_{1-6}$ alkyl groups, an adamantyl group optionally substituted with one to three $C_{1-6}$ alkyl groups, or an aryl group optionally substituted with one to three groups selected from a halogen atom and a $C_{1-6}$ alkyl group;

$R^8$ is a $C_{1-6}$ alkyl group or a phenyl group;

$R^9$ and $R^{9\prime}$, which may be the same or different, are each a hydrogen atom or a $C_{1-6}$ alkyl group;

$R^{10}$ is a $C_{1-10}$ alkyl group, a $C_{3-8}$ cycloalkyl group optionally substituted with one to three $C_{1-6}$ alkyl groups, an adamantyl group optionally substituted with one to three $C_{1-6}$ alkyl groups, or a phenyl group optionally substituted with one to three groups selected from a halogen atom and a $C_{1-6}$ alkyl group;

$R^{11}$ is a $C_{1-10}$ alkyl group, a $C_{3-8}$ cycloalkyl group substituted with one to three $C_{1-6}$ alkyl groups, an adamantyl group optionally substituted with one to three $C_{1-6}$ alkyl groups, or an aryl group optionally substituted with one to three groups selected from a halogen atom and a $C_{1-6}$ alkyl group; and $R^{12}$ is a $C_{1-6}$ alkyl group or a phenyl group, provided that compounds in which $R^1$, $R^2$ and $R^3$ are each a hydrogen atom is excluded, or a pharmaceutically acceptable salt thereof.

2. The compound according to claim 1, wherein $R^3$ is a hydrogen atom, or a pharmaceutically acceptable salt thereof.

3. The compound according to claim 2, wherein $R^1$ is —$(CR^4R^{4\prime})$—O—CO—$R^5$, —$(CR^6R^{6\prime})$—O—CO—O—$R^7$, (IIa) or (IIb):

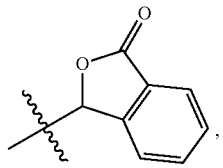
(IIa)

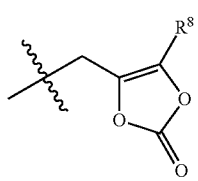
(IIb)

or a pharmaceutically acceptable salt thereof.

4. The compound according to claim 3, wherein $R^1$ is —$(CR^4R^{4\prime})$—O—CO—$R^5$ or —$(CR^6R^{6\prime})$—O—CO—O—$R^7$, or a pharmaceutically acceptable salt thereof.

5. The compound according to claim 4, wherein $R^1$ is —$(CR^4R^{4\prime})$—O—CO—$R^5$ or —$(CR^6R^{6\prime})$—O—CO—O—$R^7$, wherein $R^5$ is an adamantyl group optionally substituted with one to three methyl groups; $R^7$ is a $C_{3-8}$ cycloalkyl group substituted with one to three $C_{1-6}$ alkyl groups or is an adamantyl group optionally substituted with one to three $C_{1-6}$ alkyl groups, or a pharmaceutically acceptable salt thereof.

6. The compound according to claim 2, wherein $R^2$ is a hydrogen atom, or a pharmaceutically acceptable salt thereof.

7. The compound according to claim 1 which is selected from the group consisting of the following or a pharmaceutically acceptable salt thereof:

(1S,2S,3S,5R,6S)-6-(((adamantane-1-carbonyl)oxy)methoxy)carbonyl-2-amino-3-fluorobicyclo[3.1.0]hexane-2-carboxylic acid, (1S,2S,3S,5R,6S)-6-(1-((adamantane-1-carbonyl)oxy)ethoxy)carbonyl-2-amino-3-fluorobicyclo[3.1.0]hexane-2-carboxylic acid, (1S,2S,3S,5R,6S)-2-amino-3-fluoro-6-((1-(((((1R,2S,5R)-2-isopropyl-5-methylcyclohexyl)oxy)carbonyl)oxy)ethoxy)carbonyl)bicyclo[3.1.0]hexane-2-carboxylic acid, (1S,2S,3S,5R,6S)-2-amino-3-fluoro-6-(((((((1R,2S,5R)-2-isopropyl-5-methylcyclohexyl)oxy)carbonyl)oxy)methoxy)carbonyl)bicyclo[3.1.0]hexane-2-carboxylic acid, (1S,2S,3S,5R,6S)-2-amino-6-(1-((3,5-dimethyladamantane-1-carbonyl)oxy) ethoxy)carbonyl-3-fluorobicyclo[3.1.0]hexane-2-carboxylic acid, (1S,2S,3S,5R,6S)-2-amino-3-fluoro-6-(((octanoyloxy)methoxy)carbonyl) bicyclo[3.1.0]hexane-2-carboxylic acid, (1S,2S,3S,5R,6S)-2-amino-6-(((benzoyloxy)methoxy)carbonyl)-3-fluorobicyclo[3.1.0]hexane-2-carboxylic acid, (1S,2S,3S,5R,6S)-2-amino-6-((1-(((cyclohexyloxy)carbonyl)oxy)ethoxy) carbonyl)-3-fluorobicyclo[3.1.0]hexane-2-carboxylic acid, (1S,2S,3S,5R,6S)-2-amino-6-((1-(((cyclooctyloxy)carbonyl)oxy)ethoxy) carbonyl)-3-fluorobicyclo[3.1.0]hexane-2-carboxylic acid, (1S,2S,3S,5R,6S)-2-amino-6-((1-((((4,4-dimethylcyclohexyl)oxy)carbonyl)oxy)ethoxy)carbonyl)-3-fluorobicyclo[3.1.0]hexane-2-carboxylic acid, (1S,2S,3S,5R,6S)-6-(((((adamantan-1-yloxy)carbonyl)oxy)methoxy)carbonyl)-2-amino -3-fluorobicyclo[3.1.0]hexane-2-carboxylic acid, (1S,2S,3S,5R,6S)-6-((1-(((adamantan-1-yloxy)carbonyl)oxy)ethoxy)carbonyl)-2-amino -3-fluorobicyclo[3.1.0]hexane-2-carboxylic acid, (1S,2S,3S,5R,6S)-2-amino-3-fluoro-6-(((5-methyl-2-oxo-1,3-dioxo-4-yl) methoxy)carbonyl)bicyclo[3.1.0]hexane-2-carboxylic acid, (1S,2S,3S,5R,6S)-2-amino-3-fluorobicyclo[3.1.0]hexane-2,6-dicarboxylic acid 6-(3-phthalidyl) ester, (1S,2S,3S,5R,6S)-2-amino-3-fluoro-6-(((S)-1-(((((1R,2S,5R)-2-isopropyl-5-methylcyclohexyl)oxy)carbonyl)oxy)ethoxy)carbonyl)bicyclo[3.1.0]hexane-2-carboxylic acid, (1S,2S,3S,5R,6S)-2-amino-3-fluoro-6-(((R)-1-(((((1R,2S,5R)-2-isopropyl-5-methylcyclohexyl)oxy)carbonyl)oxy)ethoxy)carbonyl)bicyclo[3.1.0]hexane-2-carboxylic acid, (1S,2S,3S,5R,6S)-6-(((S)-1-((adamantane-1-carbonyl)oxy)ethoxy)carbonyl)-2-amino-3-fluorobicyclo[3.1.0]hexane-2-carboxylic acid, and (1S,2S,3S,5R,6S)-6-(((R)-1-((adamantane-1-carbonyl)oxy)ethoxy)carbonyl)-2-amino-3-fluorobicyclo[3.1.0]hexane-2-carboxylic acid.

8. The compound according to claim 1 which is (1S,2S,3S,5R,6S)-6-(((adamantane-1-carbonyl)oxy)methoxy)carbonyl-2-amino-3-fluorobicyclo[3.1.0]hexane-2-carboxylic acid or a pharmaceutically acceptable salt thereof.

9. The compound according to claim 1 which is (1S,2S,3S,5R,6S)-6-(1-((adamantane-1-carbonyl)oxy)ethoxy)carbonyl-2-amino-3-fluorobicyclo[3.1.0]hexane-2-carboxylic acid or a pharmaceutically acceptable salt thereof.

10. The compound according to claim 1 which is (1S,2S,3S,5R,6S)-2-amino-3-fluoro-6-((1-(((((1R,2S,5R)-2-isopropyl-5-methylcyclohexyl)oxy)carbonyl)oxy)ethoxy)carbonyl)bicyclo[3.1.0]hexane-2-carboxylic acid or a pharmaceutically acceptable salt thereof.

11. The compound according to claim 1 which is (1S,2S,3S,5R,6S)-2-amino-6-((1-(((cyclohexyloxy)carbonyl)oxy)ethoxy)carbonyl)-3-fluorobicyclo[3.1.0]hexane-2-carboxylic acid or a pharmaceutically acceptable salt thereof.

12. The compound according to claim 1 which is (1S,2S,3S,5R,6S)-2-amino-3-fluoro-6-(((S)-1-(((((1R,2S,5R)-2-isopropyl-5-methylcyclohexyl)oxy)carbonyl)oxy)ethoxy)carbonyl)bicyclo[3.1.0]hexane-2-carboxylic acid or a pharmaceutically acceptable salt thereof.

13. The compound according to claim 1 which is (1S,2S,3S,5R,6S)-2-amino-3-fluoro-6-(((R)-1-(((((1R,2S,5R)-2-isopropyl-5-methylcyclohexyl)oxy)carbonyl)oxy)ethoxy)carbonyl)bicyclo[3.1.0]hexane-2-carboxylic acid or a pharmaceutically acceptable salt thereof.

14. The compound according to claim 1 which is (1S,2S,3S,5R,6S)-6-(((R)-1-((adamantane-1-carbonyl)oxy)ethoxy)carbonyl)-2-amino-3-fluorobicyclo[3.1.0]hexane-2-carboxylic acid or a pharmaceutically acceptable salt thereof.

15. A drug formulation comprising the compound according to claim 1 or a pharmaceutically acceptable salt thereof and a pharmaceutically acceptable carrier, excipient or diluent.

16. A method of treating a disease selected from the group consisting of schizophrenia, anxiety disorder, depression, bipolar disorder, epilepsy, developmental disorders, sleep disorders, drug dependence, cognitive disorders, Alzheimer's disease, Huntington's chorea, Parkinson's disease, movement disorders associated with muscular rigidity, cerebral ischemia, cerebral insufficiency, spinal cord disorders, cephalopathy, which comprises administering the compound according to claim 1 or a pharmaceutically acceptable salt thereof to a patient.

* * * * *